(12) United States Patent
Chen et al.

(10) Patent No.: US 11,059,805 B2
(45) Date of Patent: *Jul. 13, 2021

(54) ALKYNYL-SUBSTITUTED HETEROCYCLIC COMPOUND, PREPARATION METHOD THEREFOR AND MEDICAL USE THEREOF

(71) Applicant: BEIJING INNOCARE PHARMA TECH CO., LTD., Beijing (CN)

(72) Inventors: Xiangyang Chen, Beijing (CN); Yingxiang Gao, Nanjing (CN); Norman Xianglong Kong, Nanjing (CN)

(73) Assignee: Beijing Innocare Pharma Tech Co., Ltd., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/925,738

(22) Filed: Jul. 10, 2020

(65) Prior Publication Data

US 2020/0339541 A1 Oct. 29, 2020

Related U.S. Application Data

(63) Continuation of application No. 16/353,806, filed on Mar. 14, 2019, now Pat. No. 10,710,981, which is a (Continued)

(30) Foreign Application Priority Data

Sep. 19, 2016 (CN) .......................... 201610833890.3

(51) Int. Cl.
| | |
|---|---|
| *C07D 401/14* | (2006.01) |
| *C07D 403/04* | (2006.01) |
| *A61P 35/00* | (2006.01) |
| *A61K 31/454* | (2006.01) |
| *A61K 31/415* | (2006.01) |
| *C07D 401/04* | (2006.01) |
| *C07D 231/14* | (2006.01) |
| *C07D 231/44* | (2006.01) |
| *C07D 405/14* | (2006.01) |
| *C07D 403/06* | (2006.01) |
| *A61K 31/4155* | (2006.01) |
| *C07D 401/06* | (2006.01) |

(52) U.S. Cl.
CPC .......... *C07D 401/14* (2013.01); *A61K 31/415* (2013.01); *A61K 31/4155* (2013.01); *A61K 31/454* (2013.01); *A61P 35/00* (2018.01); *C07D 231/14* (2013.01); *C07D 231/44* (2013.01); *C07D 401/04* (2013.01); *C07D 401/06* (2013.01); *C07D 403/04* (2013.01); *C07D 403/06* (2013.01); *C07D 405/14* (2013.01)

(58) Field of Classification Search
CPC .. C07D 231/44; C07D 403/03; A61K 31/415; A61P 35/00
See application file for complete search history.

(56) References Cited

U.S. PATENT DOCUMENTS

| 7,541,373 B2 | 6/2009 | Polisetti et al. |
| 8,410,286 B2 | 4/2013 | Bjergarde et al. |
| (Continued) | | |

FOREIGN PATENT DOCUMENTS

| CN | 1508130 A | 6/2004 |
| CN | 1678311 A | 10/2005 |
| (Continued) | | |

OTHER PUBLICATIONS

"Supplementary European Search Report", dated Jan. 15, 2020 issued in EP 17849992.
An, Ying, et al., "Design aAnd synthesis of novel benzoxazole analogs as Aurora B kinase inhibitors", Bioorganic & Medicinal Chemistry Letters, vol. 26, No. 13, May 7, 2016, pp. 3067-3072., May 7, 2016, pp. 3067-3072.
(Continued)

*Primary Examiner* — Kamal A Saeed
(74) *Attorney, Agent, or Firm* — Perkins Coie LLP; Viola T. Kung

(57) ABSTRACT

The present invention relates to an alkynyl-substituted heterocyclic compound acting as an FGFR inhibitor, a preparation method therefor and a medical use thereof. In particular, the present invention relates to a compound as shown in general formula (I) and a pharmaceutically acceptable salt thereof; a pharmaceutical composition including the compound or a pharmaceutically acceptable salt thereof; a method for treating and/or preventing FGFR-associated diseases, particularly tumors, by using the compound or a pharmaceutically acceptable salt thereof; and a preparation method for the compound or a pharmaceutically acceptable salt thereof. The present invention also relates to the use of the compound or a pharmaceutically acceptable salt thereof, or the pharmaceutical composition including the compound or a pharmaceutically acceptable salt thereof in the preparation of a drug for treating and/or preventing FGFR-associated diseases, particularly tumors, wherein the definition of each substituent group in general formula (I) is the same as that in the description.

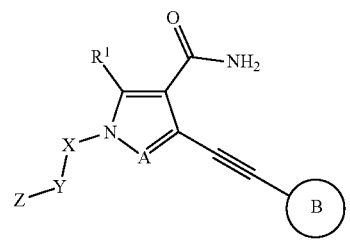

6 Claims, 1 Drawing Sheet

Related U.S. Application Data continuation-in-part of application No. PCT/CN2017/072570, filed on Jan. 25, 2017.

(56) References Cited

U.S. PATENT DOCUMENTS

| | | |
|---|---|---|
| 9,266,883 B2 | 2/2016 | Buschmann et al. |
| 2008/0182844 A1 | 7/2008 | Bjergarde et al. |
| 2009/0291984 A1 | 11/2009 | Bjergarde et al. |
| 2012/0270918 A1 | 10/2012 | Abecassis et al. |

FOREIGN PATENT DOCUMENTS

| | | |
|---|---|---|
| CN | 101304998 A | 11/2008 |
| CN | 101553473 A | 10/2009 |
| CN | 102471280 A | 5/2012 |
| EP | 3023100 A1 | 5/2016 |
| WO | 2006009741 A1 | 1/2006 |
| WO | 2007059341 A3 | 11/2007 |
| WO | 2008075068 A2 | 6/2008 |
| WO | 2013014039 A1 | 1/2013 |
| WO | 2013024427 A1 | 2/2013 |
| WO | 2016151499 A1 | 9/2016 |

OTHER PUBLICATIONS

Clayden, Jonathan, et al., "N,N'-Diarylureas: A New Family of Atropisomers Exhibiting Highly Diastereoselective Reactivity", . Org. Chem., vol. 73, No. 12, Apr. 10, 2008, pp. 4415-4423., Apr. 10, 2008, pp. 4415-4423.

Kim, Ki-Hyun, et al., "Conformational Switching on Platinum (II) Coordination Plane Triggered by Oxalate Anion", Bull. Korean Chem. Soc., vol. 32, No. 9, Dec. 31, 2011, pp. 3497-3450., Dec. 31, 2011, pp. 3497-3450.

Li, Gaoquan, et al., "Synthesis and biological evaluation of 1-(2,4,5-trisubstituted phenyl)-3-(5-cyanopyrazin-2-yl) ureas as potent Chk1 kinase inhibitors", Bioorganic & Medicinal Chemistry Letters, vol. 16, No. 8, Jan. 30, 2006, pp. 2293-2295., Jan. 2006, pp. 2293-2295.

Lu, Tsan-Wen, et al., "Molecular Switch Based on Very Weak Association between BPX26C6 and Two Recognition Units", Organic Letters, vol. 15, No. 22, Oct. 30, 2013, pp. 5742-5745., Oct. 30, 2013, pp. 5742-5745.

Nagamatsu, Kentaro, et al., "Reactions of 2-Triphenylphosphoimino-L-Azaazulenes with Aryl Isocyanates and Aryl Isothiocyanates", Heterocycles, vol. 67, No. 1, Dec. 31, 2006, pp. 337-351., Dec. 31, 2006, pp. 337-351.

Yang, Zhao, et al., "Identification of inhibitors for vascular endothelial growth factor receptor by using dynamic combinatorial chemistry", Bioorganic & Medicinal Chemistry Letters, vol. 26, No. 7, Jan. 22, 2016, pp. 1671-1674, Jan. 22, 2016, pp. 1671-1674.

International Search Report dated Jul. 28, 2017 issued in PCT/CN2017/088038.

ALKYNYL-SUBSTITUTED HETEROCYCLIC COMPOUND, PREPARATION METHOD THEREFOR AND MEDICAL USE THEREOF

This application is a continuation of U.S. application Ser. No. 16/353,806, filed Mar. 14, 2019, which is a continuation-in-part of PCT/CN2017/072570, filed Jan. 25, 2017; which claims the priority of CN201610833890.3, filed Sep. 19, 2016. The contents of the above-identified applications are incorporated herein by reference in its entirety.

TECHNICAL FIELD

The present invention relates to a new alkynyl-substituted heterocyclic compound acting as an FGFR inhibitor or a pharmaceutically acceptable salt thereof; a pharmaceutical composition including the compound or a pharmaceutically acceptable salt thereof; a preparation method for the alkynyl-substituted heterocyclic compound or a pharmaceutically acceptable salt thereof; the use of the alkynyl-substituted heterocyclic compound or a pharmaceutically acceptable salt thereof, or the pharmaceutical composition including the alkynyl-substituted heterocyclic compound or a pharmaceutically acceptable salt thereof in the preparation of a drug for treating and/or preventing FGFR-associated diseases, particularly tumors; and a method for treating and/or preventing FGFR-associated diseases, particularly tumors, by using the compound or the composition.

BACKGROUND ART

Fibroblast Growth Factor Receptor (FGFR) is a type of receptor tyrosine kinase (RTK) structurally composed of an extra-membrane ligand binding domain, a single transmembrane domain, and an intra-membrane tyrosine kinase. It mainly includes four subtypes, FGFR1, FGFR2, FGFR3 and FGFR4. It and its ligand, Fibroblast Growth Factor (FGF) play an important regulatory role in cell signaling. As an extracellular stimulatory signal, FGF binds to the extracellular domain of FGFR, causing phosphorylation of its intra-membrane tyrosine kinase, thereby activating a series of downstream signaling pathways that regulate cell proliferation, differentiation and metastasis.

A variety of tumors are closely related to FGF/FGFR expression and activation, such as non-small cell lung cancer, breast cancer, gastric cancer, liver cancer, bladder cancer, endometrial cancer, prostate cancer, cervical cancer, colon cancer, esophageal cancer, myeloma and melanoma, and so on (Clin. Cancer Res. 2012, 18, 1855). Studies have shown that FGFR1 amplification accounts for 20% of non-small cell lung cancer, FGFR2 amplification accounts for about 5% of gastric cancer, FGFR3 mutation accounts for about 70% of non-invasive bladder cancer, and FGFR4 is amplified in liver cancer (PloS One 2012, 7, e36713). Therefore, the development of inhibitors targeting FGFR has become a hot topic in anti-tumor drug research (Drug Disc. Today 2014, 19, 51).

There are currently some non-FGFR-specific drugs on the market, such as sunitinib from Pfizer, lenvatinib from Eisai, and nintedanib from Boehringer Ingelheim, but there is no FGFR-specific inhibitor currently available. Specific FGFR inhibitors that enter the clinics include HMPL-453, BGJ-398, LY-2874455, AZ-4547, JNJ-42756493, TAS-120, ARQ-087, and BLU-554.

The development of FGFR inhibitors has attracted the attention of many biopharmaceutical companies, yet new compounds still need to be developed due to their promise in the treatment of various malignant tumors. Through continuous efforts by the inventors, the present invention has designed a compound having a structure represented by the general formula (I), and it has been found that a compound having such a structure exhibits an excellent function and effect.

DESCRIPTION OF THE INVENTION

Figure 1:
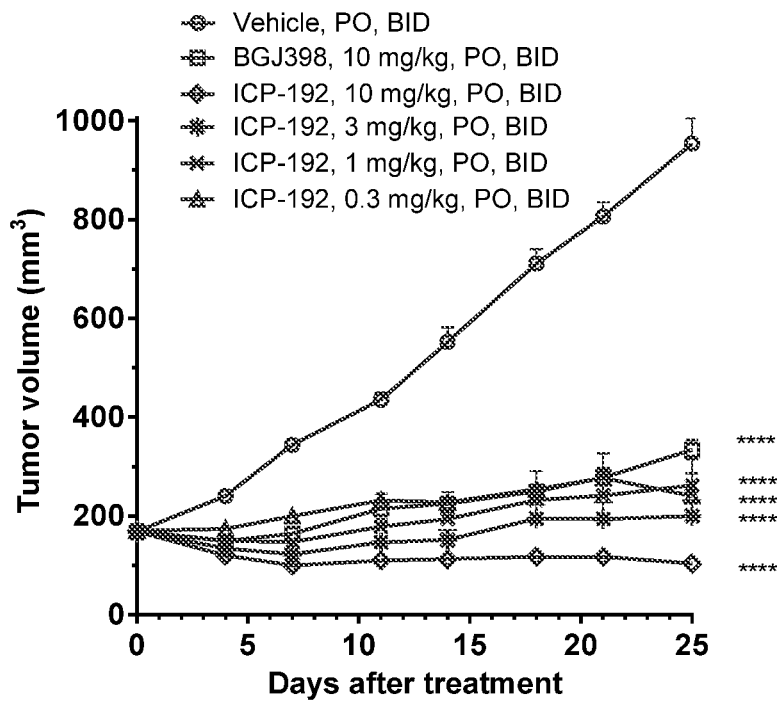
FIG. 1 shows the tumor growth curves after administering compound 21 to female BALB/c nude mice bearing SNU-16 xenograft established tumors. Data points represent group means and error bars represent standard errors of the mean (SEM). **** indicates P<0.0001 vs. the vehicle group.

The present invention provides a compound represented by the general formula (I) as an FGFR inhibitor, a prodrug thereof, a stable isotope derivative thereof, a pharmaceutically acceptable salt thereof, an isomer thereof, or a mixture thereof:

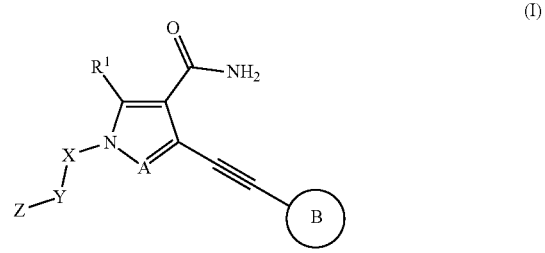

(I)

wherein:

A is N or $CR^2$;

Ring B is a benzene ring or a 5-6 membered heteroaryl ring, wherein the benzene ring and the heteroaryl ring are optionally substituted by one or more $G^1$;

$R^1$ is independently selected from H, halogen, cyano, $C_{1-6}$ alkyl or —$NHR^3$;

$R^2$ is independently selected from H, halogen, cyano, $C_{1-6}$ alkyl, wherein alkyl is optionally substituted by halogen, cyano, hydroxy or —$OC_{1-6}$ alkyl;

$R^3$ is independently selected from H, $C_{1-6}$ alkyl, $C_{3-6}$ cycloalkyl or 3-6 membered heterocyclyl, wherein the alkyl, cycloalkyl and heterocyclyl are optionally substituted by halogen, cyanide, —OR4, —$NR^5R^6$, $C_{1-6}$ alkyl, $C_{3-6}$ cycloalkyl or 3-6 membered heterocyclyl;

X is absent or is $C_{1-6}$ alkylene;

Y is absent or is selected from $C_{3-8}$ cycloalkylene, 3-8 membered heterocyclylene, arylene or heteroarylene, wherein cycloalkylene, heterocyclylen, the arylene and the heteroarylene are optionally substituted by one or more $G^2$;

Z is independently selected from cyano, —NR⁷CN,

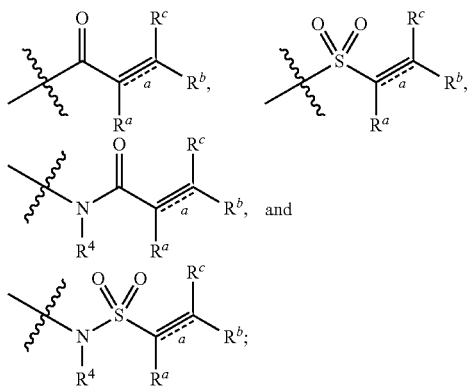

bond a is a double bond or a triple bond;

in the case where the bond a is a double bond, $R^a$, $R^b$ and R are each independently selected from H, cyano, halogen, $C_{1-6}$ alkyl, $C_{3-6}$ cycloalkyl and 3-6 membered heterocyclyl, wherein the alkyl, the cycloalkyl and the heterocyclyl are optionally substituted by one or more $G^3$.

$R^a$ and $R^b$ or $R^b$ and $R^c$ optionally together with the carbon atom to which they are linked form an optional 3-6 membered ring containing a hetero atom;

in the case where the bond a is a triple bond, $R^a$ and $R^c$ are absent, R is independently selected from H, cyano, halogen, $C_{1-6}$ alkyl, $C_{3-6}$ cycloalkyl and 3-6 membered heterocyclyl, wherein the alkyl, the cycloalkyl and the heterocyclyl are optionally substituted by one or more $G^4$;

$R^4$ is independently selected from H, $C_{1-6}$ alkyl, $C_{3-6}$ cycloalkyl or 3-6 membered heterocyclyl, wherein the alkyl, the cycloalkyl and the heterocyclyl are optionally substituted by one or more $G^5$;

$G^1$, $G^2$, $G^3$, $G^4$ and $G^5$ are each independently selected from the group consisting of halogen, cyano, $C_{1-6}$ alkyl, $C_{2-6}$ alkenyl, $C_{2-6}$ alkynyl, $C_{3-8}$ cycloalkyl, 3-8 membered heterocyclyl, $C_{6-10}$ aryl, 5-10 membered heteroaryl, —OR⁸, —OC(O)NR⁸R⁹, —C(O)OR$^B$, —C(O)NR⁸R⁹, —C(O)R⁸, —NR⁸R⁹, —NR⁸C(O)R⁹, —NR⁸C(O)NR⁹R¹⁰, —S(O)$_m$R⁸ and —NR⁸S(O)$_m$R⁹, wherein the alkyl, the alkenyl, the alkynyl, the cycloalkyl, the heterocyclyl, the aryl and the heteroaryl are optionally substituted by one or more substituent groups selected from the group consisting of halogen, cyano, $C_{1-6}$ alkyl, $C_{3-8}$ cycloalkyl, 3-8 membered heterocyclyl, —OR¹¹, —OC(O)NR¹¹R¹², —C(O)OR¹¹, —C(O)NR¹¹R¹², —C(O)R¹¹, —NR¹¹R¹², NR¹¹C(O)R¹², NR¹¹C(O)NR¹²R¹³, S(O)$_m$R¹¹ and —NR¹¹S(O)$_m$R¹²;

$R^4$, $R^5$, $R^6$, $R^8$, $R^9$, $R^1$, $R^{11}$, $R^1$, and $R^{13}$ are each independently selected from the group consisting of H, $C_{1-6}$ alkyl, a $C_{3-8}$ cycloalky, 3-8 membered monocyclic heterocyclyl, monocyclic heteroaryl and phenyl; and m is 1 or 2.

One embodiment of the present invention relates to the compound represented by the general formula (I) as mentioned above, a prodrug thereof, a stable isotope derivative thereof, a pharmaceutically acceptable salt thereof, an isomer thereof, or a mixture thereof, wherein A is N or CH, and preferably N.

Another embodiment of the present invention relates to the compound represented by the general formula (I) as mentioned above, a prodrug thereof, a stable isotope derivative thereof, a pharmaceutically acceptable salt thereof, an isomer thereof, or a mixture thereof, wherein ring B is a benzene ring.

In one aspect, the present invention provides a compound represented by the general formula (II), a prodrug thereof, a stable isotope derivative thereof, a pharmaceutically acceptable salt thereof, an isomer thereof, or a mixture thereof:

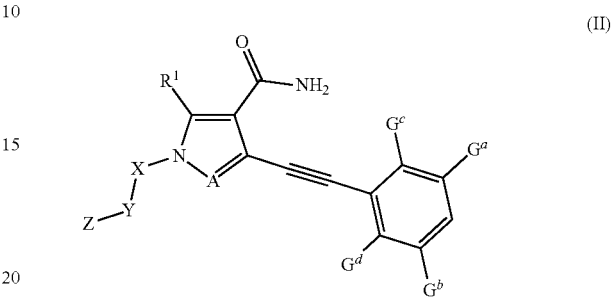

(II)

wherein, $G^a$, $G^b$, $G^c$, and $G^d$ are each independently selected from the group consisting of H, halogen, cyano, $C_{1-6}$ alkyl, $C_{3-8}$ cycloalkyl, 3-8 membered heterocyclyl, —OR⁸, —NR⁸R⁹ and —C(O)NR⁸R⁹, wherein the alkyl, the cycloalkyl and the heterocyclyl are optionally substituted by one or more substituent groups selected from the group consisting of halogen, cyano, $C_{1-6}$ alkyl, $C_{3-8}$ cycloalkyl, 3-8 membered heterocyclyl, —OR¹¹ and —NR¹¹R¹², where A, $R^1$, $R^8$, $R^9$, $R^{11}$, $R^{12}$, X, Y, Z are as defined above.

Another embodiment of the present invention relates to the compound represented by the general formula (I) as mentioned above, a prodrug thereof, a stable isotope derivative thereof, a pharmaceutically acceptable salt thereof, an isomer thereof, or a mixture thereof, which is a compound as shown in general formula (III) below, a prodrug thereof, a stable isotope derivative thereof, a pharmaceutically acceptable salt thereof, an isomer thereof, or a mixture thereof:

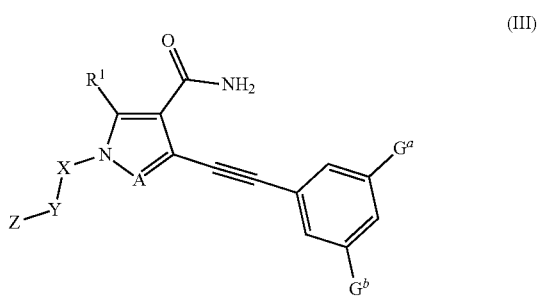

(III)

wherein, $G^a$ and $G^b$ are each independently selected from the group consisting of H, halogen, cyano, $C_{1-6}$ alkyl, $C_{3-8}$ cycloalkyl, 3-8 membered heterocyclyl, —OR⁸, —NR⁸R⁹ and —C(O)NR⁸R⁹, wherein the alkyl, the cycloalkyl and the heterocyclyl are optionally substituted by one or more substituent groups selected from the group consisting of halogen, cyano, $C_{1-6}$ alkyl, $C_{3-8}$ cycloalkyl, 3-8 membered heterocyclyl, —OR¹¹ and —NR¹¹R¹², wherein A, $R^1$, $R^8$, $R^9$, $R^{11}$, $R^{12}$, X, Y, Z are as defined above.

Another embodiment of the present invention relates to the compound represented by the general formula (I) as mentioned above, a prodrug thereof, a stable isotope derivative thereof, a pharmaceutically acceptable salt thereof, an isomer thereof, or a mixture thereof, wherein $R^1$ is independently selected from H, —$NH_2$ and —$NHC_{1-6}$ alkyl.

In one embodiment of the present invention, $R^1$ can be H, or —$NH_2$.

In one embodiment of the present invention, $G^a$, $G^b$, $G^c$, and $G^d$ are each independently selected from —$OC_{1-2}$ alkyl and halogen.

In one embodiment of the present invention, $R^1$ is independently selected from H, —$NH_2$ and —$NHR^3$; and $R^3$ is independently selected from $C_{1-6}$ alkyl, $C_{3-6}$ cycloalkyl or 3-6 membered heterocyclyl, wherein the alkyl, the cycloalkyl and the heterocyclyl is substituted by halogen, cyano, —$OR^4$, —$NR^5R^6$, $C_{1-6}$ alkyl, $C_{3-6}$ cycloalkyl or 3-6 membered heterocyclyl.

Another embodiment of the present invention relates to the compounds as shown in the general formula (I), (II) and (III), a prodrug thereof, a stable isotope derivative thereof, a pharmaceutically acceptable salt thereof, an isomer thereof, or a mixture thereof, wherein, X is absent or is $C_{1-6}$ alkylene;

Y is absent or is $C_{3-8}$ cycloalkylene or 3-8 membered heterocyclylene,

Z is independently selected from cyano, —$NR^7CN$,

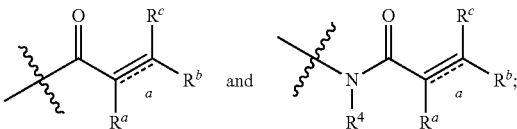

bond a is a double bond or a triple bond;

in the case where the bond a is a double bond, $R^a$, $R^b$ and $R^c$ are each independently selected from H, cyano, halogen, $C_{1-6}$ alkyl, $C_{3-6}$ cycloalkyl and 3-6 membered heterocyclyl, wherein the alkyl, the cycloalkyl and the heterocyclyl are optionally substituted by one or more substituent groups selected from the group consisting of halogen, cyano, $C_{1-6}$ alkyl, $C_{3-6}$ cycloalkyl, 3-6 membered heterocyclyl, —$OR^8$ and —$NR^8R^9$;

in the case where the bond a is a triple bond, $R^a$ and $R^c$ are absent, R is independently selected from H, cyano, halogen, $C_{1-6}$ alkyl, $C_{3-6}$ cycloalkyl and 3-6 membered heterocyclyl, wherein the alkyl, the cycloalkyl and the heterocyclyl are optionally substituted by one or more substituent groups selected form the group consisting of halogen, cyano, $C_{1-6}$ alkyl, $C_{3-6}$ cycloalkyl, 3-6 membered heterocyclyl, —$OR^8$ and —$NR^8R^9$;

$R^4$, $R^8$ and $R^9$ are each independently selected from H and $C_{1-6}$alkyl.

Another embodiment of the present invention relates to the compound represented by the general formula (I) as mentioned above, wherein the compound is selected from:

| Compound no. | Compound structure and chemical name |
| --- | --- |
| 1 | 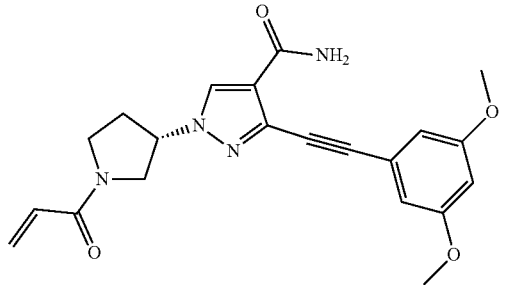 [SMILES: C=CC(=O)N1CC[C@H](n2cc(C(N)=O)c(C#Cc3cc(OC)cc(OC)c3)n2)C1]<br>(S)-1-(1-acryloylpyrrolidin-3-yl)-3-((3,5-dimethoxyphenyl)ethynyl)-1H-pyrazole-4-carboxamide |
| 2 | 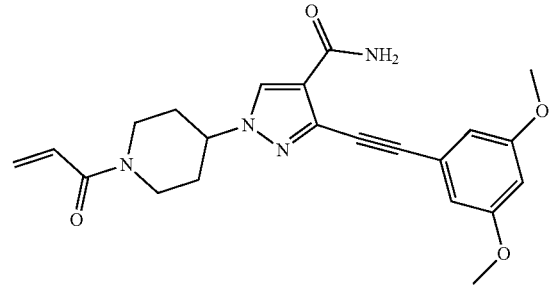 [SMILES: C=CC(=O)N1CCC(n2cc(C(N)=O)c(C#Cc3cc(OC)cc(OC)c3)n2)CC1]<br>1-(1-acryloylpiperidin-4-yl)-3-((3,5-dimethoxyphenyl)ethynyl)-1H-pyrazole-4-carboxamide |

| Compound no. | Compound structure and chemical name |
|---|---|
| 3 | 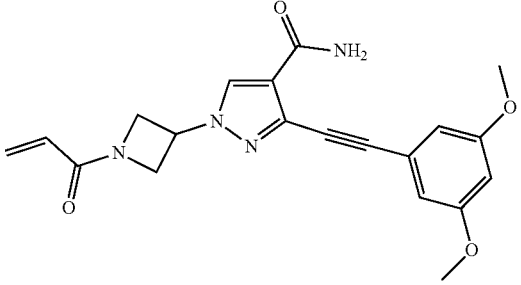 [SMILES: C=CC(=O)N1CC(n2cc(C(N)=O)c(C#Cc3cc(OC)cc(OC)c3)n2)C1]<br>1-(1-acryloylazetidin-3-yl)-3-((3,5-dimethoxyphenyl)ethynyl)-1H-pyrazole-4-carboxamide |
| 4 | 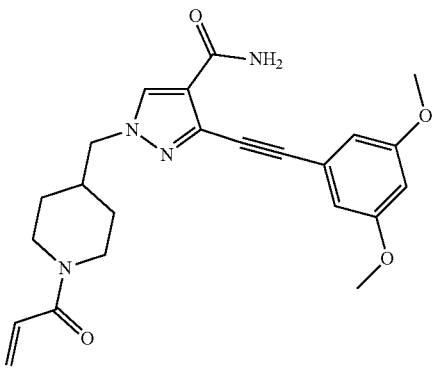 [SMILES: C=CC(=O)N1CCC(Cn2cc(C(N)=O)c(C#Cc3cc(OC)cc(OC)c3)n2)CC1]<br>1-((1-acryloylpiperidin-4-yl)methyl)-3-((3,5-dimethoxyphenyl)ethynyl)-1H-pyrazole-4-carboxamide |
| 5 | 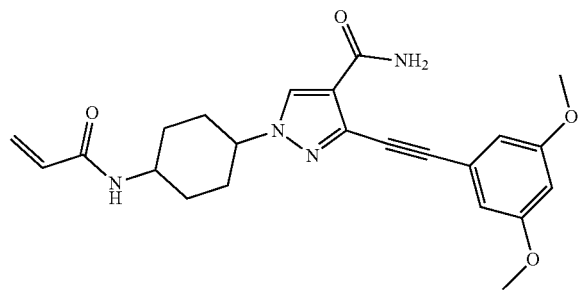 [SMILES: C=CC(=O)NC1CCC(n2cc(C(N)=O)c(C#Cc3cc(OC)cc(OC)c3)n2)CC1]<br>1-(4-acryloylaminocyclohexyl)-3-((3,5-dimethoxyphenyl)ethynyl)-1H-pyrazole-4-carboxamide |
| 6 | 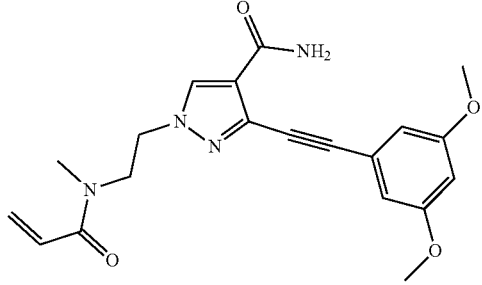 [SMILES: C=CC(=O)N(C)CCn1cc(C(N)=O)c(C#Cc2cc(OC)cc(OC)c2)n1]<br>3-((3,5-dimethoxyphenyl)ethynyl)-1-(2-(N-methylacryloylamino)ethyl)-1H-pyrazole-4-carboxamide |

-continued

| Compound no. | Compound structure and chemical name |
|---|---|
| 7 | 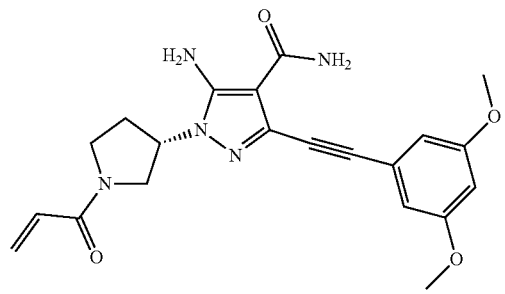 [SMILES: C=CC(=O)N1CC[C@H](n2nc(C#Cc3cc(OC)cc(OC)c3)c(C(N)=O)c2N)C1]<br>(S)-1-(1-acryloylpyrrolidin-3-yl)-5-amino-3-((3,5-dimethoxyphenyl)ethynyl)-1H-pyrazole-4-methyl Amide |
| 8 | 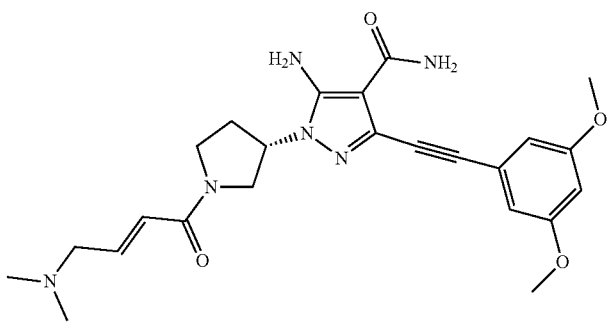 [SMILES: COc1cc(C#Cc2nn([C@H]3CCN(C(=O)/C=C/CN(C)C)C3)c(N)c2C(N)=O)cc(OC)c1]<br>(S,E)-5-amino-3-((3,5-dimethoxyphenyl)ethynyl)-1-(1-(4-(dimethylamino)but-2-enoyl)pyrrolidin-3-yl)-1H-pyrazole-4-carboxamide |
| 9 | 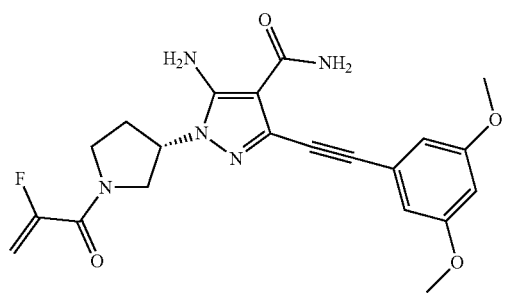 [SMILES: C=C(F)C(=O)N1CC[C@H](n2nc(C#Cc3cc(OC)cc(OC)c3)c(C(N)=O)c2N)C1]<br>(S)-5-amino-3-((3,5-dimethoxyphenyl)ethynyl)-1-(1-(2-fluoroacryloyl)pyrrolidin-3-yl)-1H-pyrazole-4-carboxamide |
| 10 | 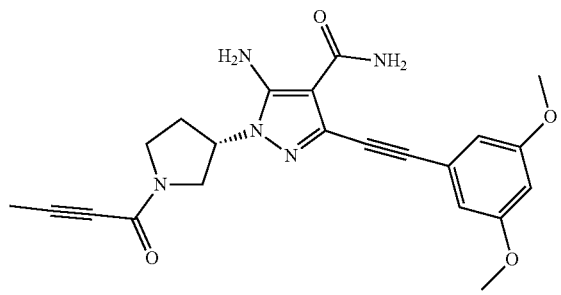 [SMILES: CC#CC(=O)N1CC[C@H](n2nc(C#Cc3cc(OC)cc(OC)c3)c(C(N)=O)c2N)C1]<br>(S)-5-amino-1-(1-(but-2-ynyl)pyrrolidin-3-yl)-3-((3,5-dimethoxyphenyl)ethynyl)-1H-pyrazole-4-carboxamide |

-continued

| Compound no. | Compound structure and chemical name |
|---|---|
| 11 | 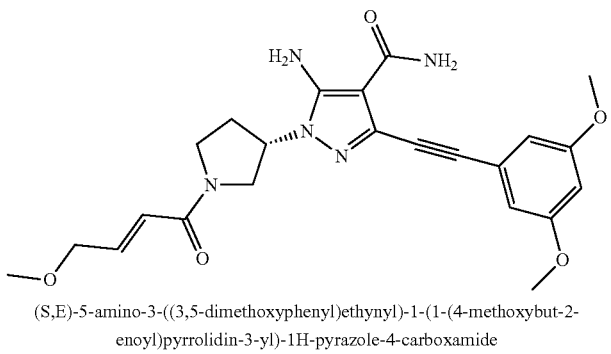
(S,E)-5-amino-3-((3,5-dimethoxyphenyl)ethynyl)-1-(1-(4-methoxybut-2-enoyl)pyrrolidin-3-yl)-1H-pyrazole-4-carboxamide |
| 12 | 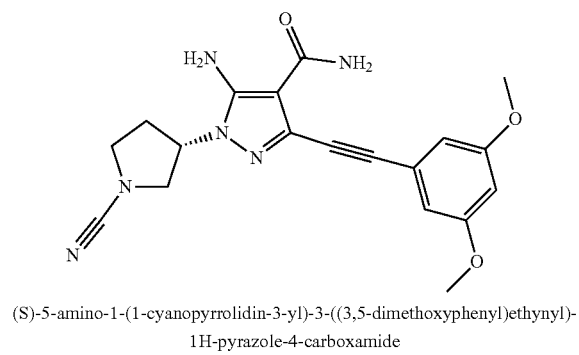
(S)-5-amino-1-(1-cyanopyrrolidin-3-yl)-3-((3,5-dimethoxyphenyl)ethynyl)-1H-pyrazole-4-carboxamide |
| 13 | 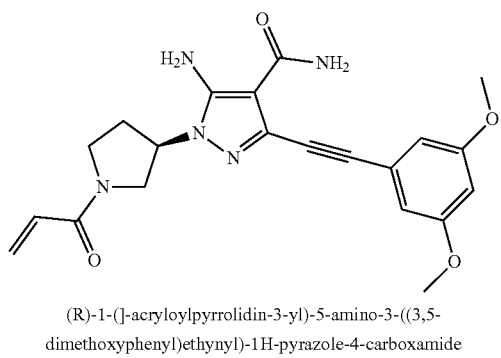
(R)-1-(]-acryloylpyrrolidin-3-yl)-5-amino-3-((3,5-dimethoxyphenyl)ethynyl)-1H-pyrazole-4-carboxamide |
| 14 | 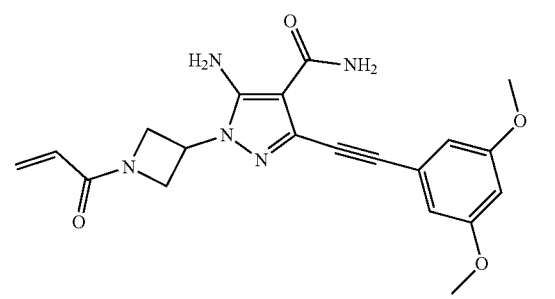 [SMILES: C=CC(=O)N1CC(n2nc(C#Cc3cc(OC)cc(OC)c3)c(C(N)=O)c2N)C1]
1-(1-acryloylazetidin-3-yl)-5-amino-3-((3,5-dimethoxyphenyl)ethynyl)-1H-pyrazole-4-carboxamide |

| Compound no. | Compound structure and chemical name |
|---|---|
| 15 | 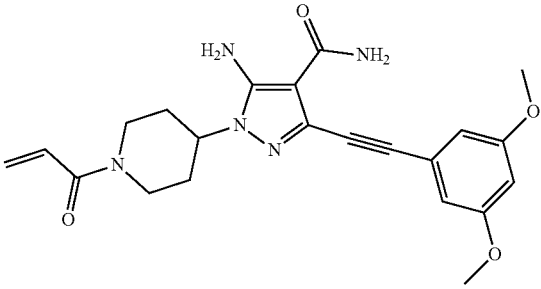 [SMILES: C=CC(=O)N1CCC(n2nc(C#Cc3cc(OC)cc(OC)c3)c(C(N)=O)c2N)CC1]<br>1-(1-acryloylpiperidin-4-yl)-5-amino-3-((3,5-dimethoxyphenyl)ethynyl)-1H-pyrazole-4-carboxamide |
| 16 | 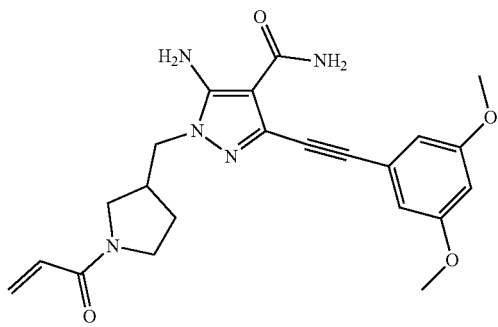 [SMILES: C=CC(=O)N1CCC(Cn2nc(C#Cc3cc(OC)cc(OC)c3)c(C(N)=O)c2N)C1]<br>1-((1-acryloylpyrrolidin-3-yl)methyl)-5-amino-3-((3,5-dimethoxyphenyl)ethynyl)-1H-pyrazole-4-carboxamide |
| 17 | 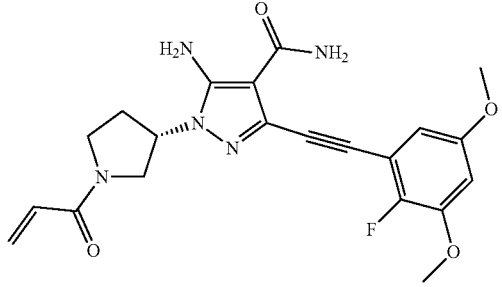 [SMILES: C=CC(=O)N1CC[C@H](n2nc(C#Cc3cc(OC)cc(OC)c3F)c(C(N)=O)c2N)C1]<br>(S)-1-(1-acryloylpyrrolidin-3-yl)-5-amino-3-((2-fluoro-3,5-dimethoxyphenyl)ethynyl)-1H-pyrazole-4-carboxamide |
| 18 | 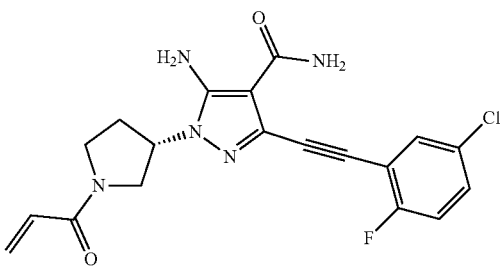 [SMILES: C=CC(=O)N1CC[C@H](n2nc(C#Cc3cc(Cl)ccc3F)c(C(N)=O)c2N)C1]<br>(S)-1-(1-acryloylpyrrolidin-3-yl)-5-amino-3-((5-chloro-2-fluorophenyl)ethynyl)-1H-pyrazole-4-carboxamide |

| Compound no. | Compound structure and chemical name |
| --- | --- |
| 19 | 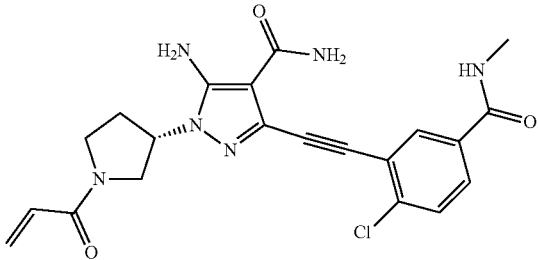 [SMILES: C=CC(=O)N1CC[C@H](n2nc(C#Cc3cc(C(=O)NC)ccc3Cl)c(C(N)=O)c2N)C1]
(S)-1-(1-acryloylpyrrolidin-3-yl)-5-amino-3-((2-chloro-5-(methylcarbamoyl)phenyl)ethynyl)-1H-pyrazole-4-carboxamide |
| 20 | 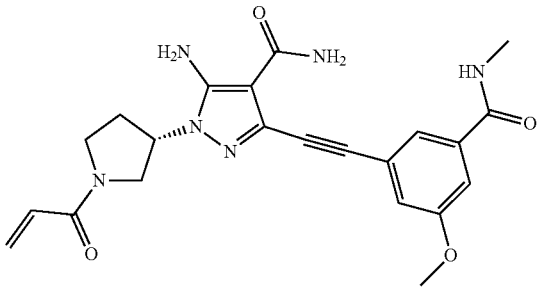 [SMILES: C=CC(=O)N1CC[C@H](n2nc(C#Cc3cc(OC)cc(C(=O)NC)c3)c(C(N)=O)c2N)C1]
(S)-1-(1-acryloylpyrrolidin-3-yl)-5-amino-3-((3-methoxy-5-(methylcarbamoyl)phenyl)ethynyl)-1H-pyrazole-4-carboxamide |
| 21 | 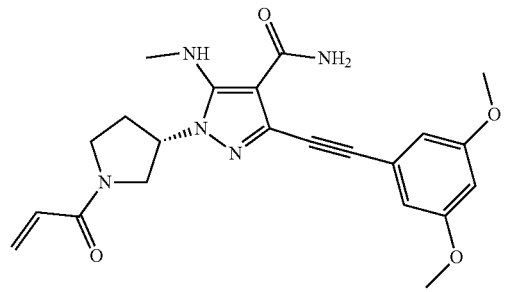 [SMILES: C=CC(=O)N1CC[C@H](n2nc(C#Cc3cc(OC)cc(OC)c3)c(C(N)=O)c2NC)C1]
(S)-1-(1-acryloylpyrrolidin-3-yl)-3-((3,5-dimethoxyphenyl)ethynyl)-5-(methylamino)-1H-pyrazole-4-carboxamide |
| 22 | 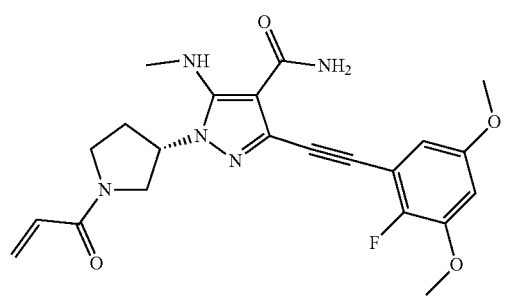 [SMILES: C=CC(=O)N1CC[C@H](n2nc(C#Cc3cc(OC)cc(OC)c3F)c(C(N)=O)c2NC)C1]
(S)-1-(1-acryloylpyrrolidin-3-yl)-3-((2-fluoro-3,5-dimethoxyphenyl)ethynyl)-5-(methylamino)-1H-pyrazole-4-carboxamide |

| Compound no. | Compound structure and chemical name |
|---|---|
| 23 | 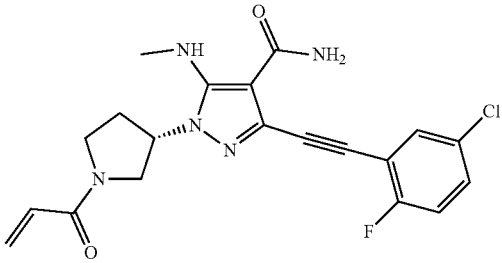 [SMILES: C=CC(=O)N1CC[C@H](n2nc(C#Cc3cc(Cl)ccc3F)c(C(N)=O)c2NC)C1]<br>(S)-1-(1-acryloylpyrrolidin-3-yl)-3-((5-chloro-2-fluorophenyl)ethynyl)-5-(methylamino)-1H-pyrazole-4-carboxamide |
| 24 | 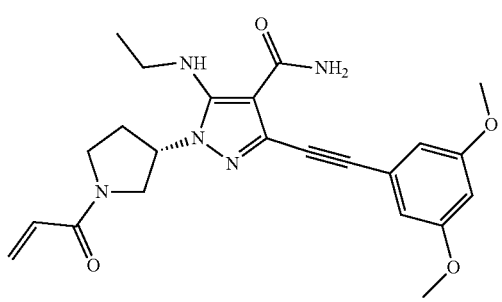 [SMILES: C=CC(=O)N1CC[C@H](n2nc(C#Cc3cc(OC)cc(OC)c3)c(C(N)=O)c2NCC)C1]<br>(S)-1-(1-acryloylpyrrolidin-3-yl)-3-((3,5-dimethoxyphenyl)ethynyl)-5-(ethylamino)-1H-pyrazole-4-carboxamide |
| 25 | 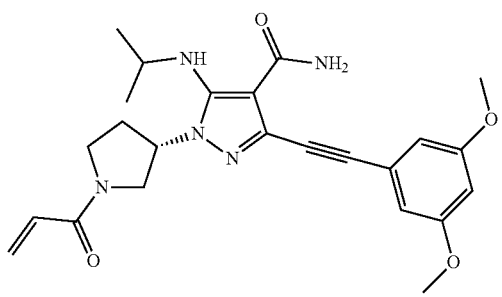 [SMILES: C=CC(=O)N1CC[C@H](n2nc(C#Cc3cc(OC)cc(OC)c3)c(C(N)=O)c2NC(C)C)C1]<br>(S)-1-(1-acryloylpyrrolidin-3-yl)-3-((3,5-dimethoxyphenyl)ethynyl)-5-(isopropylamino)-1H-pyrazole-4-carboxamide |
| 26 | 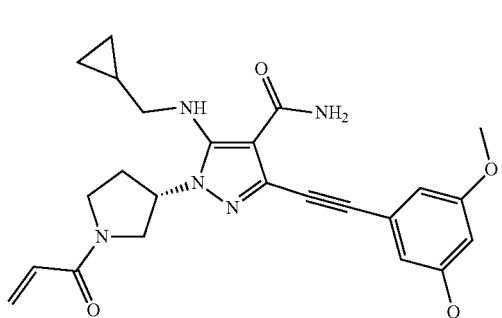<br>(S)-1-(1-acryloylpyrrolidin-3-yl)-5-((cyclopropylmethyl)amino)-3-((3,5-dimethoxyphenyl)ethynyl)-1H-pyrazole-4-carboxamide |

-continued

| Compound no. | Compound structure and chemical name |
|---|---|
| 27 | 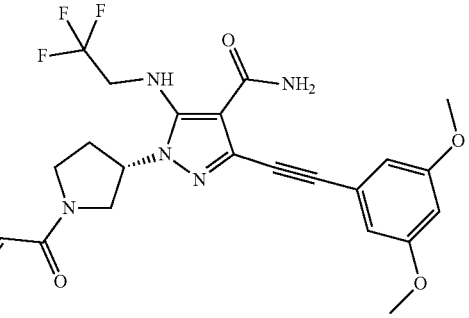<br>(S)-1-(1-acryloylpyrrolidin-3-yl)-3-((3,5-dimethoxyphenyl)ethynyl)-5-((2,2,2-trifluoroethyl)amino)-1H-pyrazole-4-carboxamide |
| 28 | 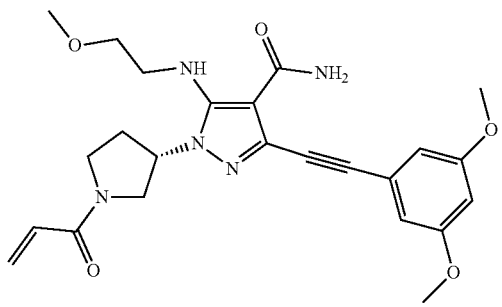 [SMILES: C=CC(=O)N1CC[C@H](n2nc(C#Cc3cc(OC)cc(OC)c3)c(C(N)=O)c2NCCOC)C1]<br>(S)-1-(1-acryloylpyrrolidin-3-yl)-3-((3,5-dimethoxyphenyl)ethynyl)-5-((2-methoxyethyl)amino)-1H-pyrazole-4-carboxamide |
| 29 | 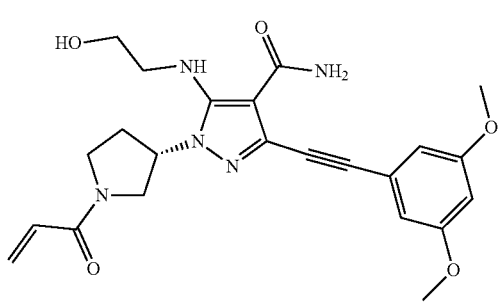 [SMILES: C=CC(=O)N1CC[C@H](n2nc(C#Cc3cc(OC)cc(OC)c3)c(C(N)=O)c2NCCO)C1]<br>(S)-1-(1-acryloylpyrrolidin-3-yl)-3-((3,5-dimethoxyphenyl)ethynyl)-5-((2-hydroxyethyl)amino)-1H-pyrazole-4-carboxamide |
| 30 | 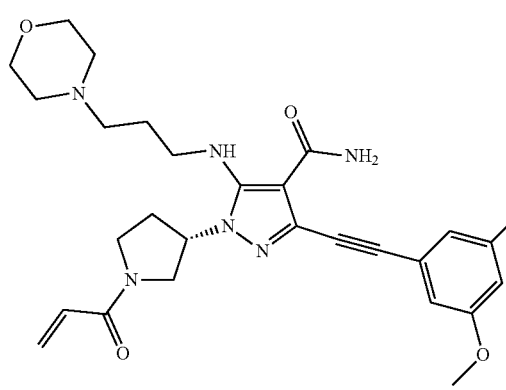<br>(S)-1-(1-acryloylpyrrolidin-3-yl)-3-((3,5-dimethoxyphenyl)ethynyl)-5-((3-morpholinopropyl)amino)-1H-pyrazole-4-carboxamide |

| Compound no. | Compound structure and chemical name |
|---|---|
| 31 | 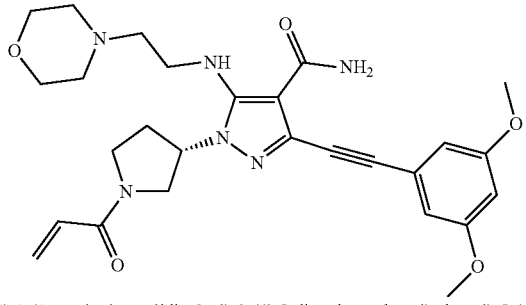<br>(S)-1-(1-acryloylpyrrolidin-3-yl)-3-((3,5-dimethoxyphenyl)ethynyl)-5-((2-morpholinoethyl)amino)-1H-pyrazole-4-carboxamide |
| 32 | 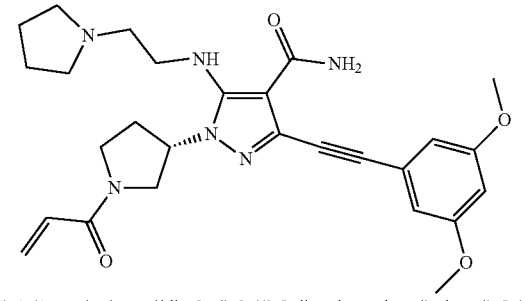<br>(S)-1-(1-acryloylpyrrolidin-3-yl)-3-((3,5-dimethoxyphenyl)ethynyl)-5-((2-(pyrrolidin-1-yl)ethyl)amino)-1H-pyrazole-4-carboxamide |
| 33 | 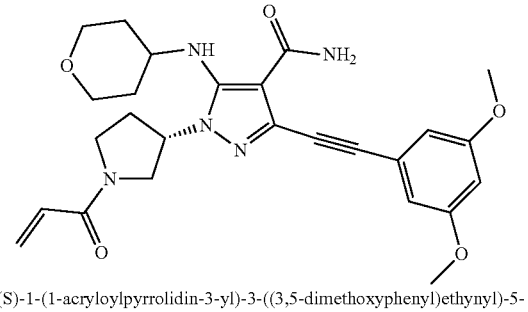<br>(S)-1-(1-acryloylpyrrolidin-3-yl)-3-((3,5-dimethoxyphenyl)ethynyl)-5-((tetrahydro-2H-pyran-4-yl)amino)-1H-pyrazole-4-carboxamide |
| 34 | 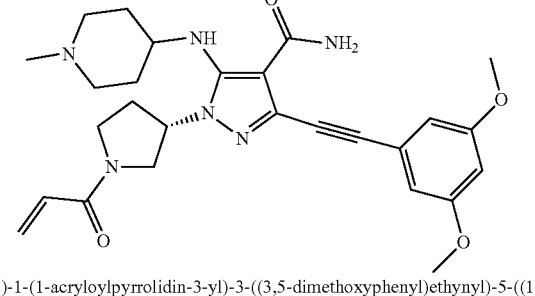<br>(S)-1-(1-acryloylpyrrolidin-3-yl)-3-((3,5-dimethoxyphenyl)ethynyl)-5-((1-methylpiperidin-4-yl)amino)-1H-pyrazole-4-carboxamide | or a prodrug thereof, a stable isotope derivative thereof, a pharmaceutically acceptable salt thereof, an isomer thereof, or a mixture thereof.

The compounds of the present invention have a significant inhibitory effect on the activity of FGFR. The compounds of the present invention are effective in inhibiting the activity of FGFR1, FGFR2, FGFR3 or FGFR4, preferably having an $IC_{50}$ of from 100 to 1000 nM for inhibiting FGFR1, FGFR2, FGFR3 or FGFR4, more preferably an $IC_{50}$ of less than 100 nM, most preferably an $IC_{50}$ of less than 10 nM. In particular, the compounds of the present invention have a significant inhibitory effect on cell proliferation of tumor cells (e.g., Hep3B, RT4, and SNU-16 tumor cells), preferably having an $IC_{50}$ of 100 to 1000 nM, more preferably having an $IC_{50}$ of less than 100 nM, and most preferably having an $IC_{50}$ less than 10 nM.

The compounds of the present invention are therefore useful in the treatment or prevention of FGFR-associated diseases including, but not limited to, tumors and inflammatory diseases such as osteoarthritis. The compounds of the present invention are useful for treating or preventing FGFR-related tumors, such as non-small cell lung cancer, esophageal cancer, melanoma, rhabdomyosarcoma, renal cell carcinoma, multiple myeloma, breast cancer, ovarian cancer, endometrial cancer, cervical cancer, stomach cancer, colon cancer, bladder cancer, pancreatic cancer, lung cancer, breast cancer, prostate cancer and liver cancer (for example, hepatocellular carcinoma), more specifically, liver cancer, gastric cancer, non-small cell lung cancer and bladder cancer. Accordingly, in still another aspect, the present invention provides a method of treating or preventing a FGFR-mediated disease, such as a tumor, comprising administering to a patient in need thereof a therapeutically effective amount of a compound of the present invention, or a prodrug thereof, a stable isotope derivative thereof, a pharmaceutically acceptable salt thereof, an isomer thereof, or a mixture thereof, or a pharmaceutical composition comprising the compounds.

Another aspect of the present invention relates to the use of a compound of the general formula (I) or a prodrug thereof, a stable isotope derivative thereof, a pharmaceutically acceptable salt thereof, an isomer thereof, or a mixture thereof in the preparation of a medicament for the treatment or prevention of a FGFR-mediated disease, such as a tumor or an inflammatory disease including, but not limited to, non-small cell lung cancer, esophageal cancer, melanoma, rhabdomyosarcoma, renal cell cancer, multiple myeloma, breast cancer, ovarian cancer, endometrium cancer, cervical cancer, stomach cancer, colon cancer, bladder cancer, pancreatic cancer, lung cancer, breast cancer, prostate cancer and liver cancer.

The present invention further relates to a pharmaceutical composition comprising a compound of the present invention or a prodrug thereof, a stable isotope derivative thereof, a pharmaceutically acceptable salt thereof, an isomer thereof, or a mixture thereof, and a pharmaceutically acceptable carrier, diluent or excipient.

Another aspect of the present invention relates to the use of a compound of the general formula (I) or a prodrug thereof, a stable isotope derivative thereof, a pharmaceutically acceptable salt thereof, an isomer thereof, or a mixture thereof, or a pharmaceutical composition for the preparation of a medicament, wherein the medicament is used for treating or preventing a FGFR mediated disease, such as a tumor and an inflammatory disease.

According to the present invention, the medicament may be in any pharmaceutical dosage form including, but not limited to, a tablet, a capsule, a solution, a lyophilized preparation, and an injection.

The pharmaceutical preparation of the present invention can be administered in the form of a dosage unit containing a predetermined amount of the active ingredient per dosage unit. Such a unit may comprise, for example, from 0.5 mg to 1 g, preferably from 1 mg to 700 mg, particularly preferably from 5 mg to 300 mg, of a compound of the present invention, depending on the disease being treated, the method of administration, as well as the age, weight and condition of the patient, or a pharmaceutical preparation may be administered in the form of dosage units containing a predetermined amount of active ingredient per dosage unit. The preferred dosage unit formulations are those containing the daily or divided doses indicated above or their corresponding fractions of the active ingredient. Furthermore, the pharmaceutical preparations of this type can be prepared using methods well known in the field of pharmaceutical.

The pharmaceutical preparations of the present invention may be adapted for administration by any suitable method desired, for example by oral (including buccal or sublingual), rectal, nasal, topical (including buccal, sublingual or transdermal), vaginal or parenteral (including subcutaneous, intramuscular, intravenous or intradermal) methods of administration. The formulations can be prepared by, for example, combining the active ingredient with one or more excipients or one or more adjuvants, using any one of the methods known in the pharmaceutical field.

DESCRIPTION OF THE EMBODIMENTS

Unless otherwise stated, the following terms used in the specification and claims of the present application have the following meanings.

The expression "$C_{x-y}$" as used herein denotes a range of the number of carbon atoms, wherein x and y are both integers, for example, a $C_{3-8}$ cycloalkyl group means a cycloalkyl group having 3 to 8 carbon atoms, that is, a cycloalkyl group having 3, 4, 5, 6, 7 or 8 carbon atoms. It should also be understood that "C3-8" also encompasses any sub-ranges contained therein, such as C3-7, C3-6, C4-7, C4-6, C5-6, and the like.

"Alkyl" refers to a saturated straight linear or branched hydrocarbyl group containing from 1 to 20 carbon atoms, for example from 1 to 18 carbon atoms, from 1 to 12 carbon atoms, from 1 to 8 carbon atoms, from 1 to 6 carbon atoms, or from 1 to 4 carbon atoms. Non-limiting examples of the alkyl groups include methyl, ethyl, n-propyl, isopropyl, n-butyl, isobutyl, tert-butyl, sec-butyl, n-pentyl, 1,1-dimethylpeopyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, and 2-ethylbutyl. The alkyl group can be substituted or unsubstituted.

"Alkenyl" refers to a straight linear or branched hydrocarbyl group containing at least one carbon to carbon double bond and usually 2 to 20 carbon atoms, for example 2 to 8 carbon atoms, 2 to 6 carbon atoms, or 2 to 4 carbon atoms. Non-limiting examples of alkenyl groups include ethenyl, 1-propenyl, 2-propenyl, 1-butenyl, 2-butenyl, 3-butenyl, 2-methyl-2-propenyl, 1,4-pentadienyl, and 1,4-butadienyl. The alkenyl group can be substituted or unsubstituted.

"Alkynyl" refers to a straight linear or branched chain hydrocarbyl group containing at least one carbon to carbon triple bond and typically 2 to 20 carbon atoms, for example 2 to 8 carbon atoms, 2 to 6 carbon atoms, or 2 to 4 carbon atoms. Non-limiting examples of alkynyl groups include ethynyl, 1-propynyl, 2-propynyl, 1-butynyl, 2-butynyl, and 3-butynyl. The alkynyl group can be substituted or unsubstituted.

"Cycloalkyl" refers to a saturated cyclic hydrocarbyl substituent group containing from 3 to 14 cyclic carbon atoms. The cycloalkyl group can be a single carbon ring and usually contains from 3 to 7 carbon ring atoms. Non-limiting examples of monocyclic cycloalkyl groups include cyclopropyl, cyclobutyl, cyclopentyl, cyclohexyl and cycloheptyl. The cycloalkyl group may alternatively be two or three ring structures fused together, such as decahydronaphthyl. The cycloalkyl group can be substituted or unsubstituted.

"Heterocyclic or heterocyclic group" refers to a saturated or partially unsaturated monocyclic or polycyclic cyclic group containing from 3 to 20 cyclic atoms, for example from 3 to 16, from 3 to 14, from 3 to 12, 3 to 10, 3 to 8, 3 to 6, or 5 to 6 cyclic atoms, in which one or more of the cyclic atoms are selected from the group consisting of nitrogen, oxygen or $S(O)_m$ (where m is an integer from 0 to 2), but does not include the ring moiety of —O—O—, —O—S— or —S—S— the remaining cyclic atoms are carbon. Preferably, it comprises from 3 to 12 cyclic atoms, more preferably from 3 to 10 cyclic atoms, most preferably 5 or 6 cyclic atoms, wherein from 1 to 4 are heteroatoms, more preferably from 1 to 3 are heteroatoms, most preferably 1 to 2 are heteroatoms. Non-limiting examples of monocyclic heterocyclic groups include pyrrolidinyl, piperidinyl, piperazinyl, morpholinyl, thiomorpholinyl, homopiperazinyl, oxearyl and azetidinyl. Polycyclic heterocyclic groups include fused, bridged or spiro polycyclic heterocyclic groups. The heterocyclic or heterocyclic group may be substituted or unsubstituted.

"Aryl" refers to an aromatic monocyclic or fused polycyclic group containing from 6 to 14 carbon atoms, preferably from 6 to 10 members, such as phenyl and naphthyl, most preferably phenyl. The aryl ring may be fused to a heteroaryl, heterocyclyl or cycloalkyl ring, wherein the ring to which the parent structure is attached is an aryl ring, non-limiting examples include:

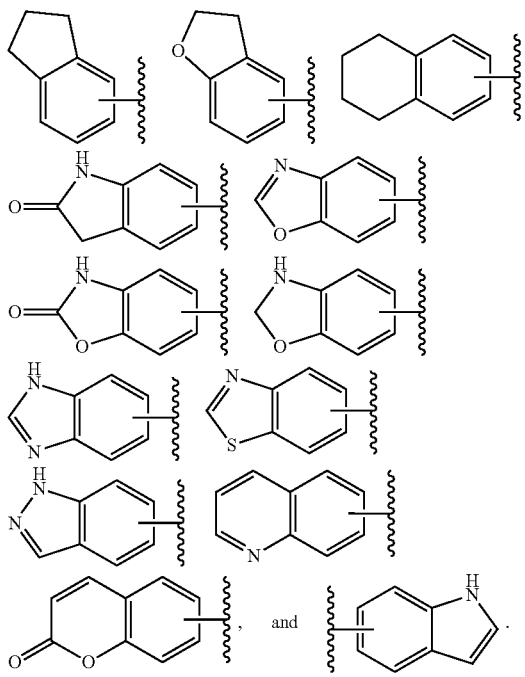

The aryl group may be substituted or unsubstituted.

"Heteroaryl or heteroaryl ring" refers to a heteroaromatic system containing from 5 to 14 cyclic atoms, wherein from 1 to 4 cyclic atoms are selected from heteroatoms including oxygen, sulfur and nitrogen. The heteroaryl group is preferably from 5 to 10 membered. More preferably, the heteroaryl group is 5 or 6 membered, such as furyl, thienyl, pyridyl, pyrrolyl, N-alkylpyrrolyl, pyrimidinyl, pyrazinyl, pyrazolyl, imidazolyl, tetrazolyl, oxazolyl, isoxazolyl, thiazolyl, isothiazolyl and the like. The heteroaryl ring may be fused to an aryl, heterocyclic or cycloalkyl ring, wherein the ring to which the parent structure is linked is a heteroaryl ring, non-limiting examples include:

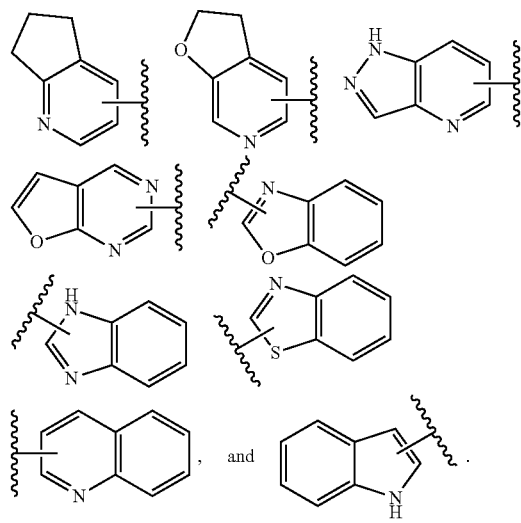

The heteroaryl group can be substituted or unsubstituted.

"Halogen" refers to fluoro, chloro, bromo or iodo.

"Cyano" refers to —CN.

"Optional" or "optionally" refers to that the subsequently described event or environment may, but need not, occur, including where the event or environment occurs or does not occur. For example, "heterocyclic group optionally substituted by an alkyl group" refers to that an alkyl group may be, but is not necessarily, present, and the description includes the case where the heterocyclic group is substituted with an alkyl group and the case where the heterocyclic group is not substituted with an alkyl group.

"Substituted" refers to one or more hydrogen atoms in the group, preferably 5, more preferably 1 to 3 hydrogen atoms, independently from each other, are substituted by a corresponding number of substituents. It goes without saying that the substituent groups are only in their possible chemical positions, and a person of ordinary skill in the art will be able to determine (by experiment or theory) substitutions that may or may not be possible without undue effort. For example, an amino group or a hydroxyl group having a free hydrogen that may be unstable when associated with a carbon atom having an unsaturated (for example, olefinic) bond. Such substituent groups include, but are not limited to, hydroxyl, amino, halogen, cyano, $C_{1-6}$ alkyl, $C_{1-6}$ alkoxy, $C_{2-6}$ alkenyl, $C_{2-6}$ alkynyl, $C_{3-8}$ cycloalkyl, and the like.

"Pharmaceutical composition" refers to a composition comprising one or more compounds described herein, or a pharmaceutically acceptable salt or a prodrug thereof, and other components such as pharmaceutically acceptable carriers and excipients. The purpose of the pharmaceutical composition is to facilitate the administration to an organism, and facilitate the absorption of the active ingredient and thereby exerts a desired biological activity.

"Isomer" refers to a compound having the same molecular formula but differing in the nature or sequence of its atomic bonding or in the spatial arrangement of its atoms, which is referred to as an "isomer." An isomer whose atomic space is arranged differently are referred to as a "stereoisomer." Stereoisomers include optical isomers, geometric isomers, and conformational isomers.

The compounds of the present invention may exist in an optical isomer form. These optical isomers are in the "R" or "S" configuration depending on the configuration of the substituents around the chiral carbon atom. Optical isomers include enantiomers and diastereomers. Methods of preparing and isolating optical isomers are known in the art.

The compounds of the present invention may also exist in a geometric isomer form. The present invention has various geometric isomers and mixtures thereof resulting from the distribution of substituents around carbon-carbon double bonds, carbon-nitrogen double bonds, cycloalkyl groups or heterocyclic groups. The substituent groups around the carbon-carbon double bond or carbon-nitrogen bond are designated as the Z or E configuration, and the substituent groups around the cycloalkyl or heterocycle are designated in the cis or trans configuration.

The compounds of the invention may also exhibit tautomerism, such as keto-enol tautomerization.

It is to be understood that the present invention includes any tautomeric or stereoisomeric forms and mixtures thereof, and is not limited to any one of the tautomeric or stereoisomeric forms used in the nomenclature or chemical structural formula of the compound.

"Isotopes" are all isotopes of the atoms occurring in the compounds of the present invention. Isotopes include those atoms having the same atomic number but different mass numbers. Examples of isotopes suitable for incorporation into the compounds of the present invention are hydrogen, carbon, nitrogen, oxygen, phosphorus, fluorine and chlorine, for example but not limited to $^2$H, $^3$H, $^{13}$C, $^{14}$C, $^{15}$N, $^{18}$O, $^{17}$O, $^{31}$P, $^{32}$P, $^{35}$P, $^{18}$F and $^{36}$Cl. Isotopically labeled compounds of the present invention can generally be prepared by conventional technical means known to a person of ordinary skill in the art or by methods analogous to those described in the accompanying examples, using the appropriate isotopically labeled reagents in place of the non-isotopically labeled reagents. Such compounds have a variety of potential uses, for example as a standard and reagent in the determination of a biological activity. In the case of stable isotopes, such compounds have the potential to advantageously alter biological, pharmacological or pharmacokinetic properties.

"Prodrug" refers to that a compound of the present invention can be administered in the form of a prodrug. A prodrug is a derivative which can be converted to the biologically active compound of the present invention under a physiological condition in vivo, for example by oxidation, reduction, hydrolysis, and so on, each of which is carried out using an enzyme or without the participation of an enzyme. An example of a prodrug is a compound in which an amino group in a compound of the invention is acylated, alkylated or phosphorylated, such as eicosylamino, alanylamino, pivaloyloxymethylamino, or wherein the hydroxy group is acylated, alkylated, phosphorylated or converted to a borate, for example acetoxy, palmitoyloxy, pivaloyloxy, succinyloxy, fumaryloxy, alanyloxy, and the like, or a carrier molecule in which the carboxyl group is esterified or amidated, or wherein the thiol group forms a disulfide bridge with a group selectively delivers a drug to the target and/or to the cytosol of the cell, such as a peptide. These compounds can be prepared from the compounds of the present invention according to certain known methods.

"Pharmaceutically salt" or "pharmaceutically acceptable salt" refers to a salt made from a pharmaceutically acceptable base or acid, including inorganic bases or acids and organic bases or acids, in the case where the compounds of the present invention contain one or more acidic or basic groups, the present invention also includes their corresponding pharmaceutically acceptable salts. Thus, the compounds of the present invention containing an acidic group may be present in the form of a salt and may be used according to the present invention, for example as an alkali metal salt, an alkaline earth metal salt or as an ammonium salt. More specific examples of such salts include sodium salts, potassium salts, calcium salts, magnesium salts or salts with ammonia or organic amines such as ethylamine, ethanolamine, triethanolamine or amino acids. The compounds of the present invention containing a basic group may be present in the form of a salt and may be used in accordance with the present invention in the form of their addition salts with inorganic or organic acids. Examples of suitable acids include hydrochloric acid, hydrobromic acid, phosphoric acid, sulfuric acid, nitric acid, methanesulfonic acid, p-toluenesulfonic acid, naphthalenedisulfonic acid, oxalic acid, acetic acid, tartaric acid, lactic acid, salicylic acid, benzoic acid, formic acid, propionic acid, pivalic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid and other acids known to a person of ordinary skill in the art. If a compound of the present invention contains both acidic and basic groups in the molecule, the present invention includes, in addition to the salt forms mentioned above, internal or internal ammonium salts. Each salt can be obtained by conventional methods known a person of ordinary skill in the art, for example by contacting them with an organic or inorganic acid or base in a solvent or dispersant, or by anion exchange or cation exchange with other salts.

Thus, when referring to "compound", "compound of the invention" or "compounds of the invention" in this application, it includes all such compound forms, such as prodrugs thereof, stable isotope derivatives thereof, pharmaceutically acceptable salts thereof, isomers thereof, mesomers thereof, raceme thereof, enantiomers thereof, diastereomers thereof, and mixtures thereof.

As used herein, the term "tumor" includes benign tumors and malignant tumors (for example, cancer).

As used herein, the term "cancer" includes various malignant tumors in which FGFR is involved, including but not limited to, non-small cell lung cancer, esophageal cancer, melanoma, rhabdomyosarcoma, renal cell carcinoma, multiple myeloma, breast cancer, ovary cancer, endometrial cancer, cervical cancer, stomach cancer, colon cancer, bladder cancer, pancreatic cancer, lung cancer, breast cancer, prostate cancer and liver cancer (such as hepatocellular carcinoma), more specifically liver cancer, stomach cancer, non-small cell lung cancer and bladder cancer.

As used herein, the term "inflammatory disease" refers to any inflammatory disease in which FGFR is involved in the onset of inflammation, such as osteoarthritis.

As used herein, the term "therapeutically effective amount" refers to an amount that includes a compound of the present invention that is effective to inhibit the function of FGFR and/or to treat or prevent the disease.

Synthesis Procedures

The present invention also provides methods of making the compounds. The preparation of the compounds of the general formula (I) of the present invention can be carried out by the following exemplary methods and embodiments, but the methods and embodiments should not be construed as limiting the scope of the present invention in any way. The compounds of the present invention may also be synthesized by other synthetic techniques known to a person of ordinary skill in the art, or a combination of methods known in the art and the methods of the invention may be employed. The product obtained in each step of the reaction is obtained by separation techniques known in the art including, but not limited to, extraction, filtration, distillation, crystallization, chromatographic separation and the like. The starting materials and chemical reagents required for the synthesis can be conventionally synthesized or purchased according to the literatures (available by searching from SciFinder).

The pyrazole compound of the general formula (I) of the present invention can be synthesized according to the route described in process A: 1) the starting material A1 is subject to a Sandmeyer reaction to obtain A2, or can be brominated to obtain A3, wherein $R_1$ may be —CN or an ester (—COOR, wherein R is an alkyl group); 2) A2 or A3 and a precursor X-L-N—P (wherein X is a leaving group, and L-N—P is a functional group containing a protected amino group, P is a protecting group for an amino group) have a substitution reaction occurring under the base catalysis to form A4, alternatively, it and a precursor having a hydroxyl group (HO-L-N—P) may be subjected to a light delay reaction (Mitsunobu reaction) to obtain A4; 3) when $R_1$ of A4 is —CN, it is hydrolyzed to an amide A5 under the NaOH/$H_2O_2$ condition; when $R_1$ of A4 is an ester (—COOR, wherein R is an alkyl group), it is first hydrolyzed under a basic condition (such as LiOH) to a carboxylic acid, and then subject to amidation to obtain A5; 4) A5 and an alkyne are coupled through a Sonogashira reaction to obtain A6; 5) an amino group in A6 is deprotected to obtain A7; 6) an amino group in A7 is derivatized with a chemical reagent (for example, BrCN, acryloyl chloride, etc.) containing a functional group reactive with a cysteine residue in the kinase ligand binding domain so as to obtain the target compound A8.

Approach A:

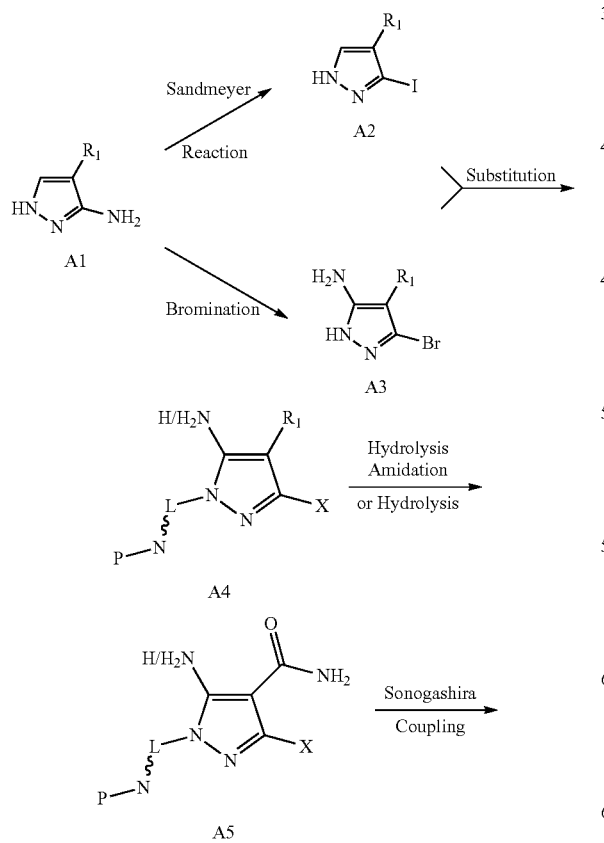

Alternatively, it can be synthesized according to the route described in approach B. In the second step, the pyrazole NH protecting group Q is introduced, and in the fifth step, the common intermediate B7 is obtained from deprotection, and next the pyrazole NH of B7 is reacted with different precursors with the protected amino group in a substitution reaction, which is next subjected to deprotection and derivatization so as to obtain the target product A8.

Approach B:

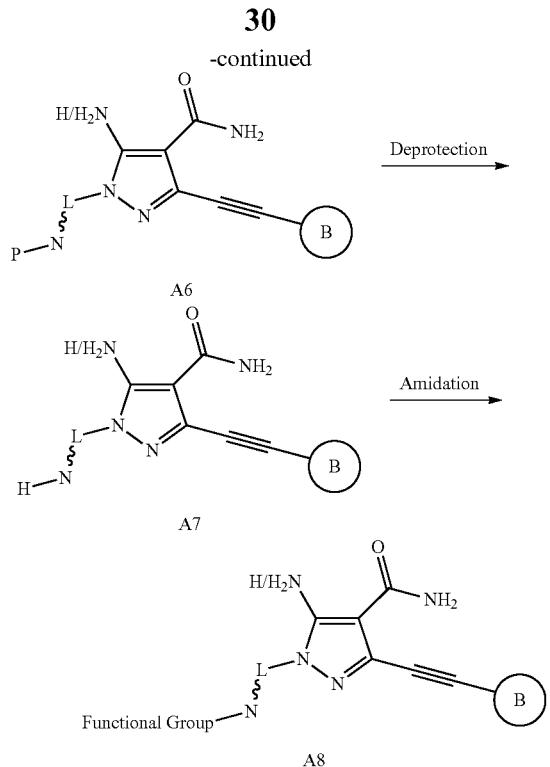

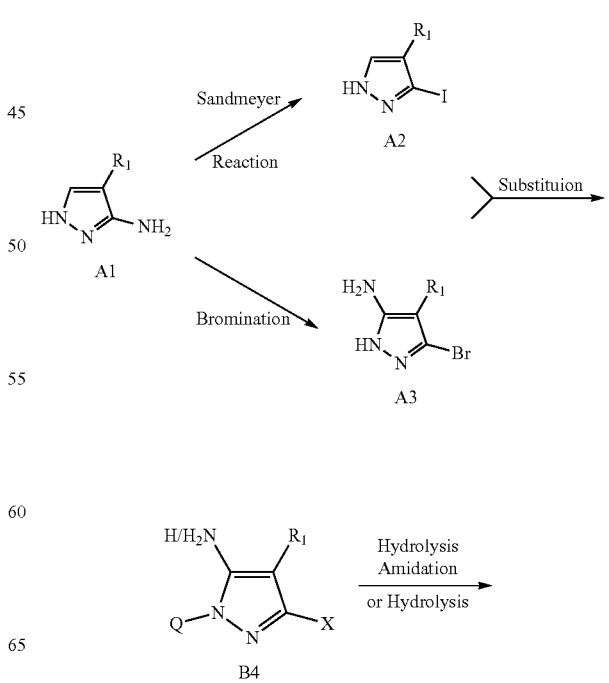

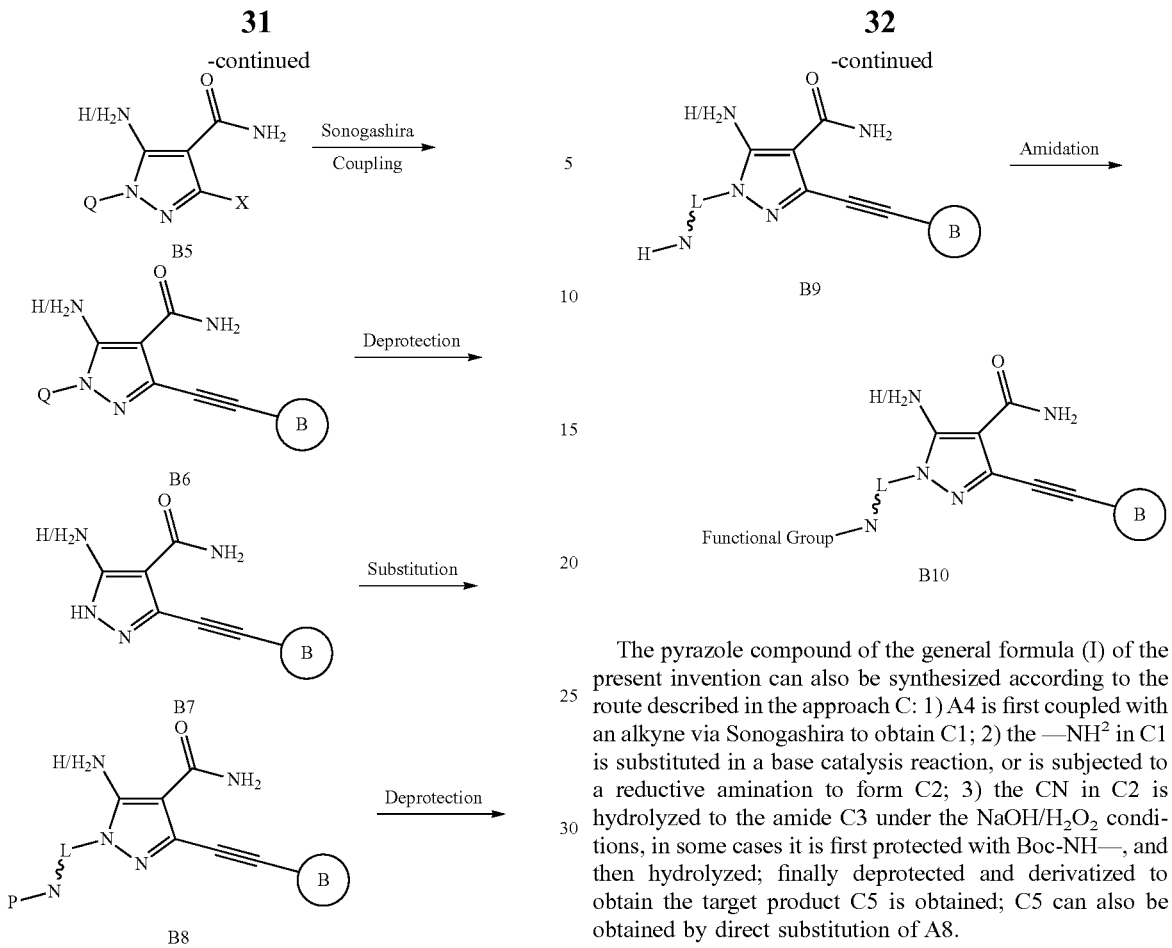

The pyrazole compound of the general formula (I) of the present invention can also be synthesized according to the route described in the approach C: 1) A4 is first coupled with an alkyne via Sonogashira to obtain C1; 2) the —NH² in C1 is substituted in a base catalysis reaction, or is subjected to a reductive amination to form C2; 3) the CN in C2 is hydrolyzed to the amide C3 under the NaOH/H₂O₂ conditions, in some cases it is first protected with Boc-NH—, and then hydrolyzed; finally deprotected and derivatized to obtain the target product C5 is obtained; C5 can also be obtained by direct substitution of A8.

Approach C:

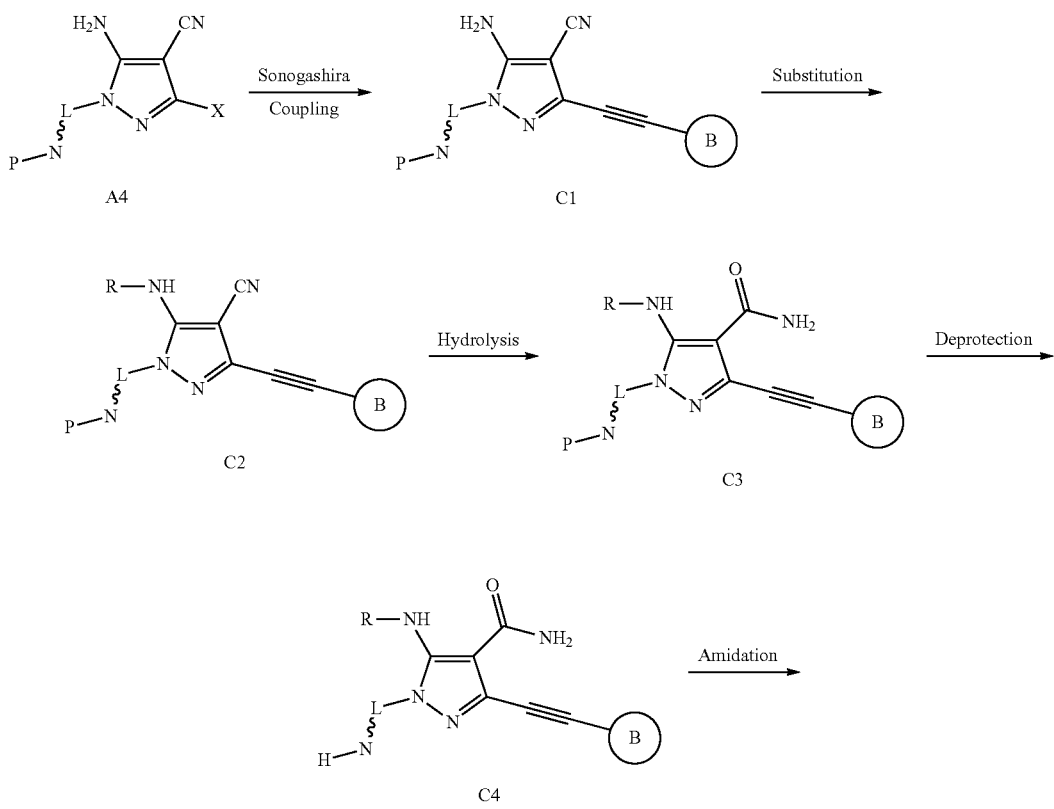

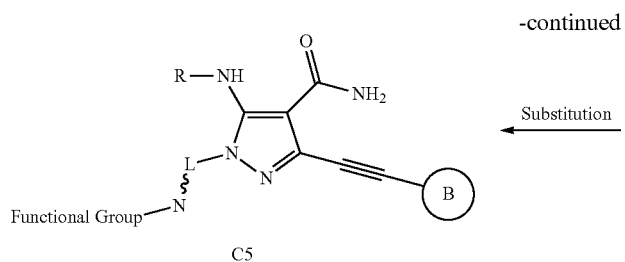

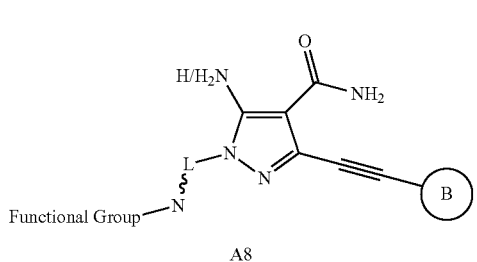

EXAMPLES

The structure of a compound is determined by nuclear magnetic resonance (NMR) or mass spectrometry (MS). The NMR was measured by Bruker AVANCE-400 or Varian Oxford-300 NMR, and the solvent was deuterated dimethyl sulfoxide (DMSO-$d_6$), deuterated chloroform (CDCl$_3$), deuterated methanol (CD$_3$OD), and the internal standard was tetramethylsilane (TMS), chemical shift is provided in the unit of $10^{-6}$ (ppm).

The MS was measured using an Agilent SQD (ESI) mass spectrometer (manufacturer: Agilent, model: 6120).

The HPLC measurements were performed using an Agilent 1200 DAD high pressure liquid chromatograph (Sunfire C18, 150×4.6 mm, 5 µm column) and a Waters 2695-2996 high pressure liquid chromatograph (Gimini C18 150×4.6 mm, 5 µm column).

The thin-layer chromatography silica gel plate uses Qingdao Ocean GF254 silica gel plate. The specification of silica gel plate used in the thin-layer chromatography (TLC) is 0.15 mm to 0.2 mm. The specification for thin layer chromatography separation and purification is the silicone board of 0.4 mm to 0.5 mm.

Column chromatography generally uses Qingdao Ocean 200 to 300 meshes silica gel as the carrier.

The known starting materials of the present invention may be synthesized according to the methods known in the art, or may be purchased from ABCR GmbH & Co. KG, Acros Organics, Aldrich Chemical Company, Accela ChemBio Inc., Beijing Coupling chemicals, and other companies.

In the examples of the present invention, unless otherwise specified, the reactions were all carried out under an argon atmosphere or a nitrogen atmosphere.

An argon atmosphere or a nitrogen atmosphere refers to that the reaction flask is connected to an argon or nitrogen balloon having a volume of about 1 L.

A hydrogen atmosphere refers to that the reaction flask is connected to a hydrogen balloon of about 1 L volume.

The pressurized hydrogenation reaction was carried out using a GCD-500G high purity hydrogen generator and a BLT-2000 medium pressure hydrogenator from Beijing Jiawei Kechuang Technology Co., Ltd.

The hydrogenation reaction is usually evacuated, charged with hydrogen, and repeatedly operated three times.

The microwave reaction used a CEM Discover-SP type microwave reactor.

In the examples of the present invention, unless otherwise specified, the reaction temperature was room temperature, and the temperature range was from 20° C. to 30° C.

The reaction progress in the examples was monitored by thin layer chromatography (TLC), and the system used for the reaction was A: a dichloromethane and methanol system; B: a petroleum ether and ethyl acetate system, the volume ratio of the solvents was adjusted based on the polarity of the compound.

The system of the column chromatography eluent used in the process of purifying the compound and the developing agent system used for developing in the thin layer chromatography include A: a dichloromethane and methanol system; B: a petroleum ether and ethyl acetate system, the volume ratio of the solvents was adjusted according to the polarity of the compound, and a small amount of triethylamine and an acidic or basic reagent may be added for adjustment.

Example 1

(S)-1-(1-acryloylpyrrolidin-3-yl)-3-((3,5-dimethoxyphenyl)ethynyl)-1H-pyrazole-4-carboxamide

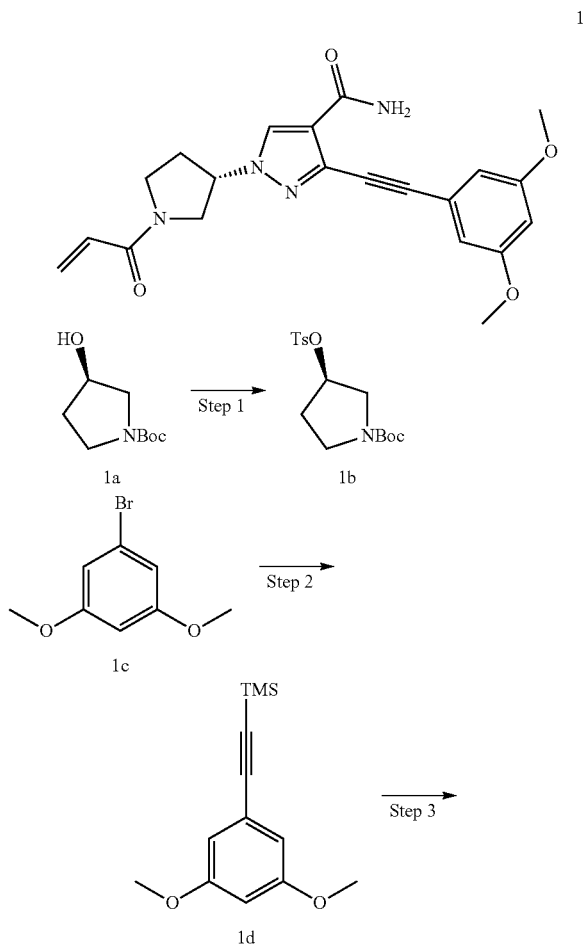

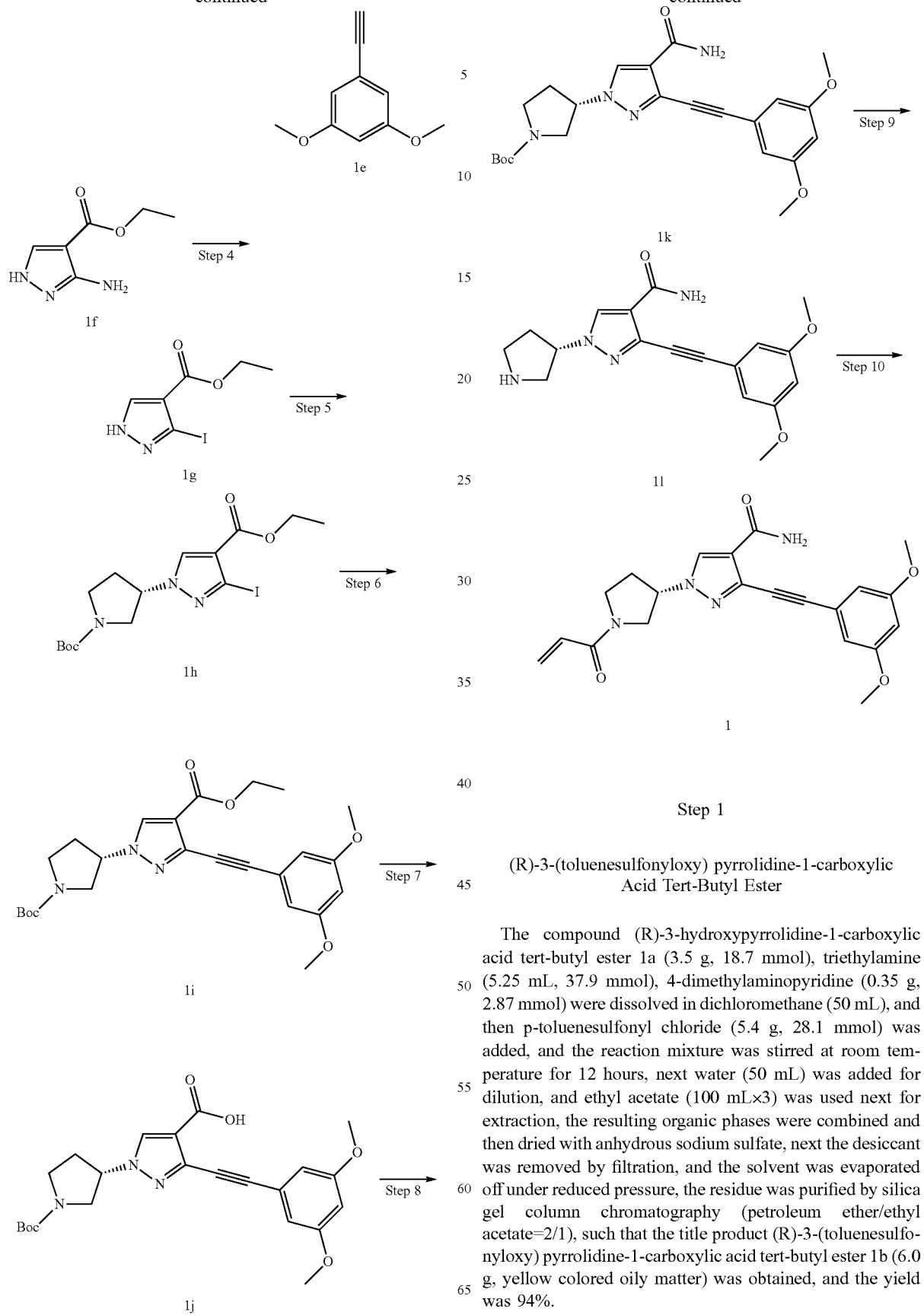

Step 1

(R)-3-(toluenesulfonyloxy) pyrrolidine-1-carboxylic Acid Tert-Butyl Ester

The compound (R)-3-hydroxypyrrolidine-1-carboxylic acid tert-butyl ester 1a (3.5 g, 18.7 mmol), triethylamine (5.25 mL, 37.9 mmol), 4-dimethylaminopyridine (0.35 g, 2.87 mmol) were dissolved in dichloromethane (50 mL), and then p-toluenesulfonyl chloride (5.4 g, 28.1 mmol) was added, and the reaction mixture was stirred at room temperature for 12 hours, next water (50 mL) was added for dilution, and ethyl acetate (100 mL×3) was used next for extraction, the resulting organic phases were combined and then dried with anhydrous sodium sulfate, next the desiccant was removed by filtration, and the solvent was evaporated off under reduced pressure, the residue was purified by silica gel column chromatography (petroleum ether/ethyl acetate=2/1), such that the title product (R)-3-(toluenesulfonyloxy) pyrrolidine-1-carboxylic acid tert-butyl ester 1b (6.0 g, yellow colored oily matter) was obtained, and the yield was 94%.

MS m/z (ESI): 364[M+23]

Step 2

((3,5-dimethoxyphenyl)ethynyl) trimethylsilane

The mixture 1-bromo-3,5-dimethoxybenzene 1c (6.51 g, 30 mmol), trimethylsilyl acetylene (8.8 g, 90 mmol), bis(triphenylphosphine) palladium chloride (1.05 g, 1.5 mmol), cuprous iodide (0.56 g, 3.0 mmol), triethylamine (80 mL) and N,N-dimethylformamide (150 mL) were heated to 80° C., and stirred under nitrogen for 12 hours; the reaction mixture was cooled to room temperature; concentrated under reduced pressure, and the residue was purified by silica gel column chromatography (petroleum ether), so as to obtain the title product ((3,5-dimethoxyphenyl)ethynyl) trimethylsilane 1d (6.2 g, brown solid), and the yield was 88%.

MS m/z (ESI): 235 [M+1]

Step 3

1-ethynyl-3,5-dimethoxy Benzene ((3,5-Dimethoxyphenyl)ethynyl) trimethylsilane d (3.0 g, 12.8 mmol) was dissolved in methanol (100 mL) and potassium carbonate (3.5 g, 25.6 mmol) was added and stirred at room temperature for 2 hours; and filter and the resulting filtrate was concentrated under reduced pressure; the residue was purified by silica gel column chromatography (petroleum ether), so as to obtain the title product 1-ethynyl-3,5-dimethoxybenzene 1e (2 g, yellow solid), and the yield was 96%.

Step 4

3-iodo-1H-pyrazole-4-carboxylic Acid Ethyl Ester

3-Amino-1H-pyrazole-4-carboxylic acid ethyl ester 1f (4.7 g, 30.3 mmol) was dissolved in concentrated hydrochloric acid (12 M, 40 mL) and cooled to 0° C., a solution of sodium nitrite (4.25 g, 60 mmol) (7.5 mL) was added and then stirred for 5 min, then a solution of potassium iodide (12.5 g, 75 mmol) (17.5 mL) was slowly added and continued stirring for 30 minutes, the reaction mixture was poured into a saturated aqueous solution of sodium thiosulfate (200 mL), and extracted with ethyl acetate (400 mL×3), the organic phases were combined and dried by anhydrous sodium sulfate, the desiccant was then removed by filtration, and the solvent was removed under reduced pressure; the residue was purified by silica gel column chromatography (petroleum ether/ethyl acetate=2/1), so as to obtain the title product 3-iodo-1H-pyrazole-4-carboxylic acid ethyl ester 1 g (6.4 g, pale yellow solid), and the yield was 80%.

MS m/z (ESI): 267 [M+1]

Step 5

(S)-1-(1-(tert-butoxycarbonyl)pyrrolidin-3-yl)-3-iodo-1H-pyrazole-4-ethyl Formate A mixture of 1-iodo-1H-pyrazole-4-carboxylic acid ethyl ester 1 g (4.5 g, 17 mmol), (R)-3-(toluenesulfonyloxy)pyrrolidine-1-carboxylic acid tert-butyl ester 1b (6.1 g, 17.8 mmol), cesium carbonate (7.5 g, 20.4 mmol), and N,N-dimethylformamide (50 mL) were heated to 80° C. and stirred for 3 hours, the reaction mixture was cooled to room temperature, and then poured into a saturated sodium bicarbonate solution (200 mL), which was then extracted with ethyl acetate (300 mL×3); the organic phases are combined and dried over anhydrous sodium sulfate, next filtered to remove the desiccant, and the solvent is removed under reduced pressure, the residue was purified by silica gel column chromatography (petroleum ether/ethyl acetate=5/1 to 2/1), so as to obtain the title product (S)-1-(1-(tert-Butoxycarbonyl)pyrrolidin-3-yl)-3-iodo-1H-pyrazole-4-ethyl formate 1H (3.1 g, pale yellow solid), and the yield was 42%.

MS m/z (ESI): 458 [M+23]

Step 6

(S)-1-(1-(tert-butoxycarbonyl)pyrrolidin-3-yl)-3-((3,5-dimethoxyphenyl)ethynyl)-1H-pyrazole-4-ethyl Formate A mixture of (S)-1-(1-(tert-butoxycarbonyl)pyrrolidin-3-yl)-3-iodo-1H-pyrazole-4-ethyl formate 1 h (1 g, 2.25 mmol), 1-acetylene-3,5-dimethoxybenzene 1e (0.75 g, 4.5 mmol), bis(triphenylphosphine) palladium chloride (175 mg, 0.25 mmol), cuprous iodide (95 mg, 0.5 mmol), triethyl the amine (12.5 ml), and N,N-dimethylformamide (12.5 mL) was heated to 80° C. and stirred for 12 hours, the reaction mixture was cooled to room temperature, and the solvent was removed under reduced pressure, the residue was purified by silica gel column chromatography (petroleum ether/ethyl acetate=2/1), so as to obtain the title product (S)-1-(1-(tert-butoxycarbonyl)pyrrolidin-3-yl)-3-((3,5-dimethoxyphenyl)ethynyl)-1H-pyrazole-4-ethyl formate (0.95 g, yellow oily substance), and the yield was 90%.

MS m/z (ESI): 414 [M+1-56]

Step 7

(S)-1-(1-(tert-butoxycarbonyl)pyrrolidin-3-yl)-3-((3,5-dimethoxyphenyl)ethynyl)-1H-pyrazole-4-formic Acid (S)-1-(1-(tert-butoxycarbonyl)pyrrolidin-3-yl)-3-((3,5-dimethoxyphenyl)ethynyl)-1H-pyrazole-4-ethyl formate 1i (0.30 g, 0.64 mmol) was dissolved in tetrahydrofuran (3 mL), and a sodium hydroxide solution (4 M, 2 mL) was added and stirred at room temperature for 1 hour, the reaction mixture was concentrated under reduced pressure, and the residue was acidified with hydrochloric acid (6 M, 1 mL), and then extracted with ethyl acetate (10 mL×3), the organic phases were combined and dried over anhydrous sodium sulfate, and the desiccant was removed by filtering, the solvent was removed under reduced pressure, so as to obtain the title product (S)-1-(1-(tert-butoxycarbonyl)pyrrolidin-3-yl)-3-((3,5-dimethoxyphenyl)ethynyl)-1H-pyrazole-4-formate 1j (200 mg, light yellow oily substance), and the yield was 71%.

MS m/z (ESI): 386 [M+1-56]

Step 8

(S)-3-(4-carbamoyl-3-((3,5-dimethoxyphenyl)ethynyl)-1H-pyrazol-1-yl)pyrrolidine-1-carboxylic Acid Tert-Butyl Ester A mixture of (S)-1-(1-(tert-Butoxycarbonyl)pyrrolidin-3-yl)-3-((3,5-dimethoxyphenyl)ethynyl)-1H-pyrazole-4-formate 1j (220 mg, 0.5 mmol), ammonium chloride (270 mg, 5 mmol), O-(7-azabenzotriazol-1-yl)-N,N,N',N'-tetramethyluronium hexafluorophosphate (HATU) (228 mg, 0.6 mmol), N,N-diisopropylethylamine (129 mg, 1 mmol) and N,N-dimethylformamide (5 mL) was stirred at room temperature overnight, and then diluted with water, and extracted with ethyl acetate, the organic phases were combined and dried over anhydrous sodium sulfate, the desiccant was removed by filtering, the solvent was removed under reduced pressure, the residue was purified by preparative chromatography on a thin layer of silica gel (dichloromethane/methanol=20/1), so as to obtain the title product (S)-3-(4-carbamoyl-3-((3,5-dimethoxyphenyl)ethynyl)-1H-pyrazol-1-yl)pyrrolidine-1-carboxylic acid tert-butyl ester 1k (140 mg, white solid), and the yield was 64%.

MS m/z (ESI): 385 [M+1-56]

Step 9

(S)-3-((3,5-dimethoxyphenyl)ethynyl)-1-(pyrrolidin-3-yl)-1H-pyrazole-4-carboxamide A mixture of (S)-3-(4-carbamoyl-3-((3,5-dimethoxyphenyl)ethynyl)-1H-pyrazol-1-yl)pyrrolidine-1-carboxylic acid tert-butyl ester 1k (50 mg, 0.11 mmol), hydrochloric acid (6 M, 5 mL) and dioxane (5 mL) was stirred at room temperature for 1 hour, and then the solvent was removed under reduced pressure, so as to obtain the title product (S)-3-((3,5-dimethoxyphenyl)ethynyl)-1-(pyrrolidin-3-yl)-1H-pyrazole-4-carboxamide 11 (42 mg, a hydrochloride salt, crude product), and the yield was 100%.

MS m/z (ESI): 341 [M+1]

Step 10

(S)-1-(1-acryloylpyrrolidin-3-yl)-3-((3,5-dimethoxyphenyl)ethynyl)-1H-pyrazole-4-carboxamide A mixture of (S)-3-((3,5-dimethoxyphenyl)ethynyl)-1-(pyrrolidin-3-yl)-1H-pyrazole-4-carboxamide hydrochloride 11 (30 mg, 0.08 mmol), N,N-diisopropylethylamine (31 mg, 0.24 mmol) and tetrahydrofuran (15 mL) was added dropwise of a solution of acryloyl chloride (11 mg, 0.12 mmol) in tetrahydrofuran (5 mL), the reaction mixture was stirred at room temperature for 30 minutes, and then quenched with water (30 mL), extracted with ethyl acetate, the organic phases were combined and dried over anhydrous sodium sulfate, and then filtered to remove the desiccant, the solvent was removed under reduced pressure, the residue was purified by preparative chromatography on a thin layer of silica gel (dichloromethane/methanol=20/1), so as to obtain the title product of (S)-1-(1-acryloylpyrrolidin-3-yl)-3-((3,5-dimethoxyphenyl)ethynyl)-1H-pyrazole-4-carboxamide 1 (15 mg, white solid), and the yield was 50%.

MS m/z (ESI): 395[M+1]

$^1$H NMR (400 MHz, CDCl$_3$) δ 8.10 (d, J=9.8 Hz, 1H), 6.96 (brs, 1H), 6.71 (d, J=2.3 Hz, 2H), 6.54-6.52 (m, 1H), 6.46-6.39 (m, 2H), 5.80 (brs, 1H), 5.76-5.72 (m, 1H), 5.01-4.92 (m, 1H), 4.13-4.00 (m, 2H), 3.90-3.75 (m, 8H), 2.62-2.44 (m, 2H).

Example 2

1-(1-acryloylpiperidin-4-yl)-3-((3,5-dimethoxyphenyl)ethynyl)-1H-pyrazole-4-carboxamide

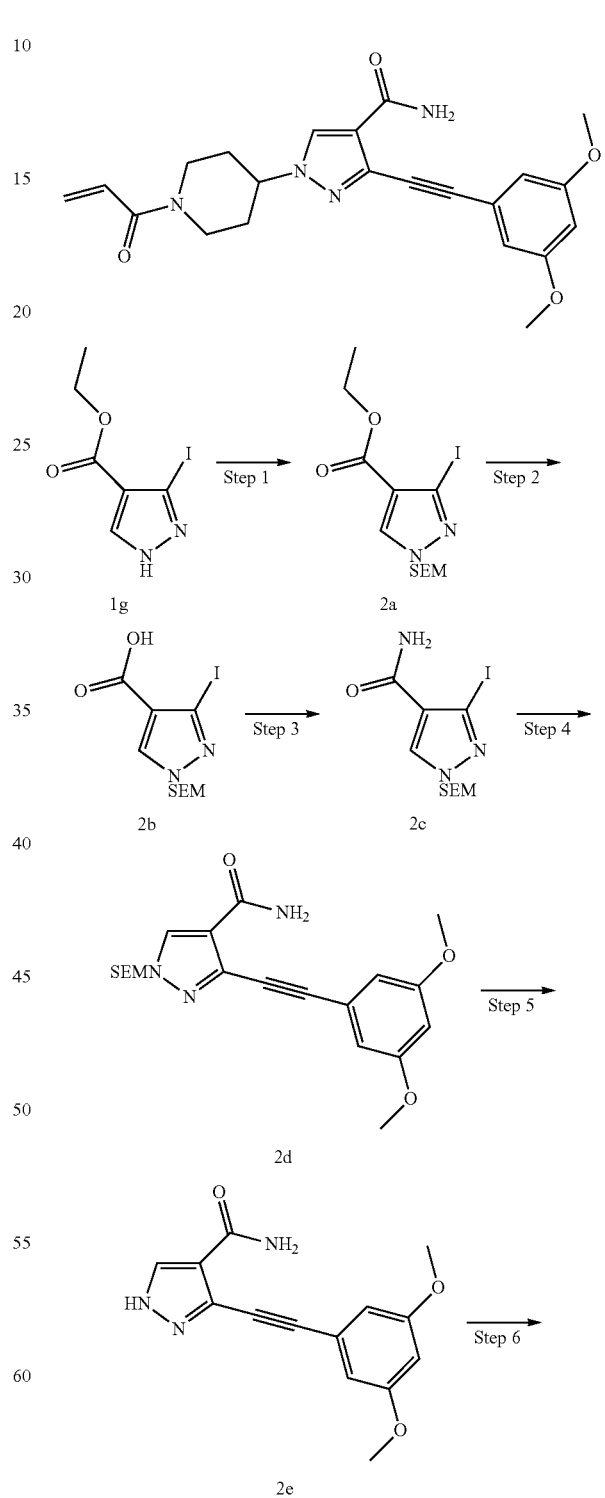

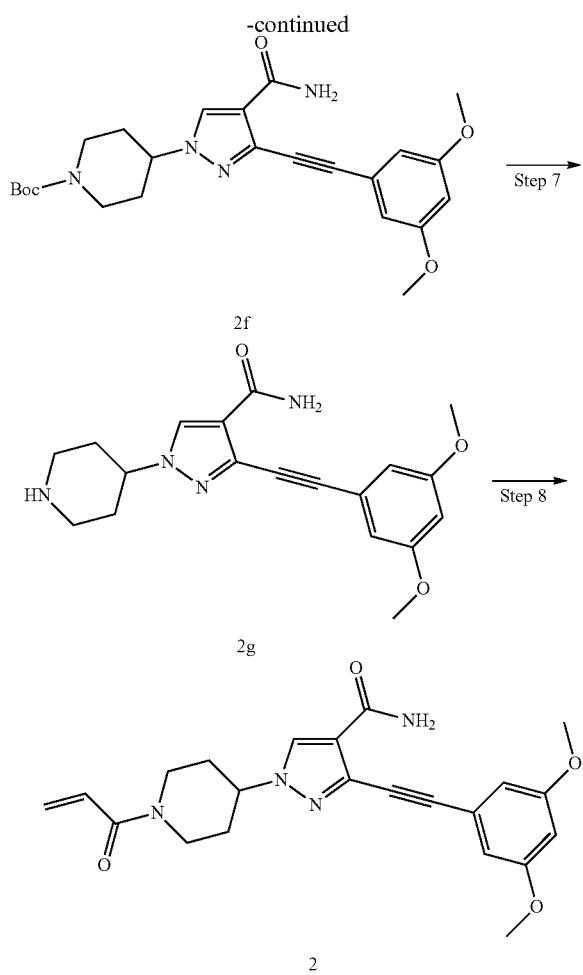

Step 1

3-iodo-1-((2-(trimethylsilyl)ethoxy)methyl)-1H-pyrazole-4-ethyl Formate

A compound 3-iodo-1H-pyrazole-4-ethyl formate 1 g (2.01 g, 7.5 mmol) was dissolved in tetrahydrofuran (80 mL) and cooled to 0° C., sodium hydride (60% mineral oil dispersion, 0.42 g, 10.5 mmol) was added, stirred at room temperature for 1 hour, and the reaction mixture was added 2-(trimethylsilyl)ethoxymethyl chloride (1.76 g, 10.5 mmol), continued stirring for 15 hours, and then a saturated brine (100 mL) was added to the reaction mixture, which was then extracted with ethyl acetate (150 mL×2), the organic phases were combined and washed with saturated brine (100 mL), the solvent was removed under reduced pressure, the residue was purified by silica gel column chromatography (petroleum ether/ethyl acetate=5/1 to 1/2), so as to obtain the title product 3-iodo-1-((2-(trimethylsilyl)ethoxy)methyl)-1H-pyrazole-4-ethyl formate (2.6 g, colorless oily substance), and the yield was 87%.

MS m/z (ESI): 397[M+1]

Step 2

3-iodo-1-((2-(trimethylsilyl)ethoxy)methyl)-1H-pyrazole-4-carboxylic Acid

The compound 3-iodo-1-((2-(trimethylsilyl)ethoxy) methyl)-1H-pyrazole-4-ethyl formate 2a (2.6 g, 6.5 mmol) was dissolved in tetrahydrofuran (40 mL), an aqueous solution of lithium hydroxide (1M, 13 mL) was added and stirred at room temperature for 15 hours, which was then diluted with water (20 mL), and acidified to pH=4-5 with hydrochloric acid (1M), which was then extracted with ethyl acetate (50 mL×3), the organic phases were combined and washed with a saturated brine (100 mL), the solvent is removed under reduced pressure, and then dries, so as to obtain the title product 3-iodo-1-((2-(trimethylsilyl)ethoxy) methyl)-1H-pyrazole-4-carboxylic acid 2b (2.03 g, white solid), and the yield was 85%.

MS m/z (ESI): 391[M+23]

Step 3

3-iodo-1-((2-(trimethylsilyl)ethoxy)methyl)-1H-pyrazole-4-carboxamide

The compound 3-iodo-1-((2-(trimethylsilyl)ethoxy) methyl)-1H-pyrazole-4-carboxylic acid 2b (2.03 g, 5.5 mmol), diisopropylethylamine (2.13 g, 16.5 mmol) and N,N-dimethylformamide (20 mL) were mixed, which was then sequentially added O-(7-azabenzotriazol-1-yl)-N,N,N', N'-tetramethyluronium hexafluorophosphate (HATU) (2.5 g, 6.6 mmol) and 1-hydroxybenzotriazole (890 mg, 6.6 mmol), after stirring at room temperature for 1 hour, a solid ammonium chloride (1.47 g, 27.5 mmol) was added, continued stirring for 15 hours, and then a saturated brine (30 mL) was added to the reaction mixture, which was extracted with ethyl acetate (50 mL×3), and the organic phases were combined and washed with a saturated brine (100 mL), after removing the solvent under reduced pressure, the residue was purified by silica gel column chromatography (dichloromethane/methanol=20/1), so as to obtain the title product 3-iodo-1-((2-(trimethylsilyl)ethoxy)methyl)-1H-pyrazole-4-carboxamide 2c (2.3 g, yellow oily substance), and the yield was 100%.

MS m/z (ESI): 368[M+1]

Step 4

3-((3,5-dimethoxyphenyl)ethynyl)-1-((2-(trimethylsilyl)ethoxy)methyl)-1H-pyrazole-4-carboxamide The compounds of 3-iodo-1-((2-(trimethylsilyl)ethoxy) methyl)-1H-pyrazole-4-carboxamide 2c (2.7 g, 7.3 mmol), 1-ethynyl-3,5-dimethoxybenzene (1.78 g, 11 mmol), triethylamine (2.2 g, 21.9 mmol), bis(triphenylphosphine)palladium chloride (512 mg, 0.73 mmol), and anhydrous tetrahydrofuran (70 mL) were mixed, and then subjected to deoxygenation, and stirred at room temperature for 15 hours under an argon atmosphere, the solvent was then removed under reduced pressure, the residue was purified by silica gel column chromatography (ethyl acetate/petroleum ether=10/1 to 2/1), so as to obtain the title product 3-((3,5-dimethoxyphenyl)ethynyl)-1-((2-(trimethylsilyl)ethoxy) methyl)-1H-pyrazole-4-carboxamide 2d (1.5 g, yellow solid), and the yield was 51%.

MS m/z (ESI): 402[M+1]

Step 5

3-((3,5-dimethoxyphenyl)ethynyl)-1H-pyrazole-4-carboxamide 3-((3,5-Dimethoxyphenyl)ethynyl)-1-((2-(trimethylsilyl) ethoxy)methyl)-1H-pyrazole-4-carboxamide 2d (1.4 g, 3.5 mmol), ethylenediamine (525 mg, 8.75 mmol) and tetrahydrofuran (30 mL) were mixed together, and then a solution of tetrabutylammonium fluoride in tetrahydrofuran (1 M, 17.5 mL, 17.5 mmol) was added, after heating to reflux for 15 hours, cooled to room temperature, and a saturated brine (20 mL) was added, and extracted with ethyl acetate (100 mL×3), the resulting organic phases were combined and dried over anhydrous sodium sulfate, the desiccant was then removed by filtering, and the solvent was removed under reduced pressure, the residue was purified by silica gel column chromatography (dichloromethane/methanol=20/1), so as to obtain the title product 3-((3,5-dimethoxyphenyl)ethynyl)-1H-pyrazole-4-carboxamide 2e (600 mg, white solid), and the yield was 63%.

MS m/z (ESI): 272[M+1]

Step 6

4-(4-carbamoyl-3-((3,5-dimethoxyphenyl)ethynyl)-1H-pyrazol-1-yl)piperidine-1-carboxylic Acid Tert-Butyl Ester The compounds 3-((3,5-dimethoxyphenyl)ethynyl)-1H-pyrazole-4-carboxamide 2e (180 mg, 0.66 mmol), 4-bromopiperidine-1-carboxylic acid tert-butyl ester (264 mg, 0.99 mmol), potassium carbonate (182 mg, 1.32 mmol) and N,N-dimethylformamide (10 mL) were mixed together, and then heated to 75° C. and stirred for 15 hours, next water was added, the resulting solution was extracted with ethyl acetate (50 mL×3), the organic phases were combined and washed with saturated brine, dried over anhydrous sodium sulfate, the desiccant was removed by filtering, and the solvent was removed under reduced pressure, the residue was purified by silica gel column chromatography (dichloromethane/methanol=20/1), so as to obtain the title product 4-(4-carbamoyl-3-((3,5-dimethoxyphenyl)ethynyl)-1H-pyrazol-1-yl)piperidine-1-carboxylic acid tert-butyl ester 2f (120 mg, yellow solid, containing regioisomer), and the yield was 40%.

MS m/z (ESI): 477[M+23]

Step 7

3-((3,5-dimethoxyphenyl)ethynyl)-1-(piperidin-4-yl)-1H-pyrazole-4-carboxamide

The compound 4-(4-carbamoyl-3-((3,5-dimethoxyphenyl)ethynyl)-1H-pyrazol-1-yl)piperidine-1-carboxylic acid tert-butyl ester 2f (120 mg, 0.26 mmol, a mixture) was dissolved in ethanol (20 mL), and then hydrogen chloride in ethanol (4M, 1 mL, 4 mmol) was added, stirred at room temperature for 15 hours, the solvent is removed under reduced pressure, after the residue was dissolved in methanol (20 mL), adjusted the solution to pH=8 to 9 with a saturated sodium bicarbonate solution, next the solvent was removed under reduced pressure, and the residue was purified by silica gel column chromatography (dichloromethane/methanol=10/1), so as to obtain the title product 3-((3,5-dimethoxyphenyl)ethynyl)-1-(piperidin-4-yl)-1H-pyrazole-4-carboxamide 2 g (25 mg, white solid), and the yield was 27%.

MS m/z (ESI): 355[M+1]

Step 8

1-(1-acryloylpiperidin-4-yl)-3-((3,5-dimethoxyphenyl)ethynyl)-1H-pyrazole-4-carboxamide The compound 3-((3,5-dimethoxyphenyl)ethynyl)-1-(piperidin-4-yl)-1H-pyrazole-4-carboxamide 2 g (25 mg, 0.07 mmol), alkene propionyl chloride (10 mg, 0.11 mmol), solid sodium hydrogen carbonate (18 mg, 0.21 mmol), water (2 mL) and tetrahydrofuran (10 mL) were mixed at 0° C. and stirred at this temperature for 10 hours, which was then extracted with ethyl acetate (20 mL×3), the organic phases were combined and dried over anhydrous sodium sulfate, the desiccant was then removed by filtering, and the solvent was removed under reduced pressure, next the residue was purified by silica gel column chromatography (dichloromethane/methanol=10/1), so as to obtain the title product 1-(1-acryloylpiperidin-4-yl)-3-((3,5-dimethoxyphenyl)ethynyl)-1H-pyrazole-4-carboxamide 2 (17 mg, white solid), and the yield was 60%.

MS m/z (ESI): 409[M+1]

$^1$H NMR (400 MHz, CDCl$_3$) δ 8.10 (s, 1H), 7.01 (brs, 1H), 6.72 (d, J=2.2 Hz, 2H), 6.62 (dd, J=16.8, 10.6 Hz, 1H), 6.55 (t, J=2.2 Hz, 1H), 6.33 (dd, J=16.8, 1.5 Hz, 1H), 5.80 (brs, 1H), 5.76 (dd, J=10.6, 1.6 Hz, 1H), 4.81 (brs, 1H), 4.40 (t, J=11.4 Hz, 1H), 4.18 (brs, 1H), 3.82 (s, 6H), 3.26 (brs, 1H), 2.89 (brs, 1H), 2.42-2.25 (m, 2H), 2.08-2.00 (m, 2H).

Examples 3-6 were carried out in accordance with the procedure provided in Example 2:

Example 3

1-(1-acryloylazetidin-3-yl)-3-((3,5-dimethoxyphenyl)ethynyl)-1H-pyrazole-4-carboxamide

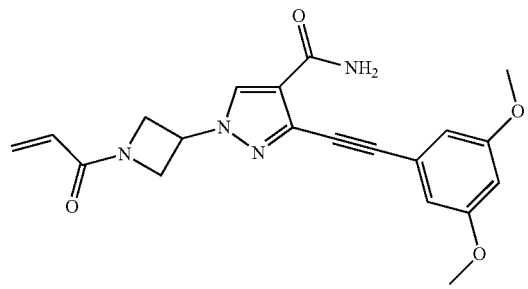

3

MS m/z (ESI): 381[M+1]

$^1$H NMR (400 MHz, DMSO-d$_6$) δ 8.43 (s, 1H), 7.30 (s, 2H), 6.73 (d, J=2.2 Hz, 2H), 6.60 (t, J=2.2 Hz, 1H), 6.38 (dd, J=17.0, 10.3 Hz, 1H), 6.16 (dd, J=17.0, 2.1 Hz, 1H), 5.73 (dd, J=10.3, 2.1 Hz, 1H), 5.41-5.28 (m, 1H), 4.71 (t, J=8.6 Hz, 1H), 4.50 (dd, J=9.2, 4.9 Hz, 1H), 4.46-4.36 (m, 1H), 4.20 (dd, J=10.7, 4.8 Hz, 1H), 3.78 (s, 6H).

Example 4

1-((1-anoylpiperidin-4-yl)methyl)-3-((3,5-dimethoxyphenyl)ethynyl)-1H-pyrazole-4-carboxamide

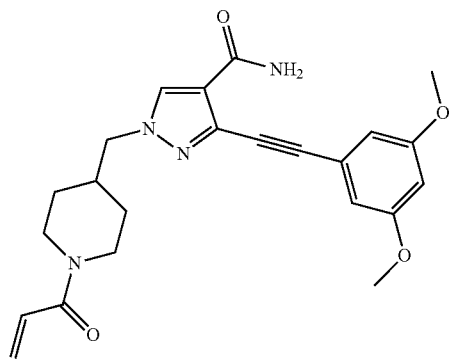

4

MS m/z (ESI): 423[M+1]

$^1$H NMR (400 MHz, CDCl$_3$) δ 8.00 (s, 1H), 6.98 (brs, 1H), 6.72 (s, 2H), 6.61-6.54 (m, 2H), 6.28 (d, J=16.8 Hz, 1H), 5.87 (brs, 1H), 5.70 (d, J=10.5 Hz, 1H), 4.72 (brs, 1H), 4.04 (brs, 3H), 3.82 (s, 6H), 3.05 (brs, 1H), 2.64 (brs, 1H), 2.27 (brs, 1H), 1.69 (brs, 2H), 1.24 (brs, 2H).

Example 5

1-(4-acryloylaminocyclohexyl)-3-((3,5-dimethoxyphenyl)ethynyl)-1H-pyrazole-4-carboxamide

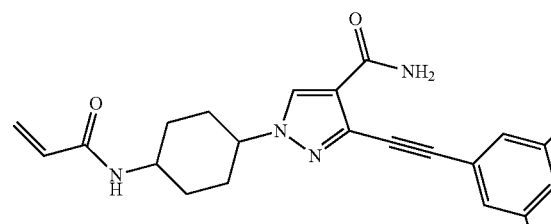

5

MS m/z (ESI): 423[M+1]

$^1$H NMR (400 MHz, CD$_3$OD) δ 8.25 (s, 1H), 6.77 (d, J=2.3 Hz, 2H), 6.58 (t, J=2.3 Hz, 1H), 6.38 (dd, J=17.1, 10.0 Hz, 1H), 6.26 (dd, J=17.1, 2.0 Hz, 1H), 5.68 (dd, J=10.1, 2.0 Hz, 1H), 4.38-4.33 (m, 1H), 4.13-4.11 (m, 1H), 3.82 (s, 6H), 2.28-2.18 (m, 2H), 2.07-2.02 (m, 2H), 1.96-1.80 (m, 4H).

Example 6

3-((3,5-dimethoxyphenyl)ethynyl)-1-(2-(N-methylacryloylamino)ethyl)-1H-pyrazole-4-carboxamide

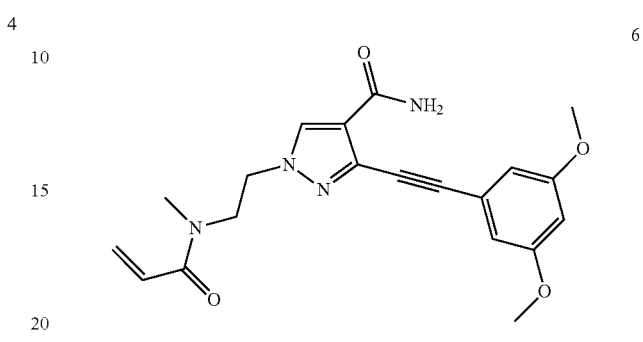

6

MS m/z (ESI): 383[M+1]

$^1$H NMR (300 MHz, DMSO-d$_6$) δ 8.24 (s, 1H), 7.10-6.90 (m, 2H), 6.76 (s, 2H), 6.69-6.54 (m, 2H), 6.07 (d, J=16.5 Hz, 1H), 5.64 (d, J=9.8 Hz, 1H), 4.37 (t, J=5.7 Hz, 2H), 3.89-3.80 (m, 8H), 2.94 (s, 3H).

Example 7

(S)-1-(1-acryloylpyrrolidin-3-yl)-5-amino-3-((3,5-dimethoxyphenyl)ethynyl)-1H-pyrazole-4-carboxamide

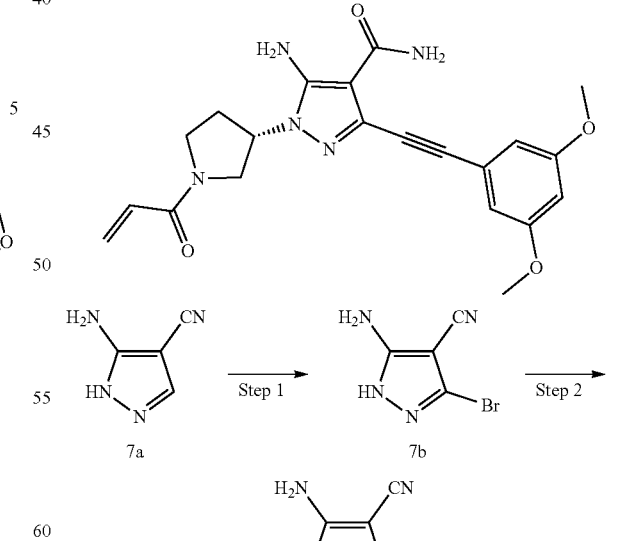

7

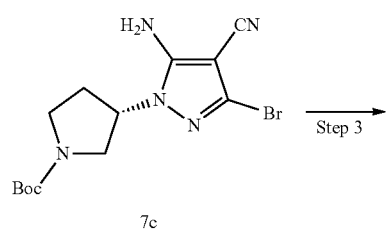

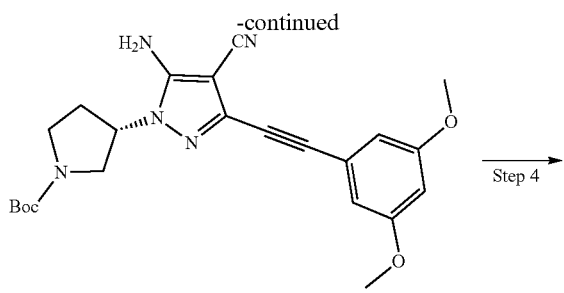

7d

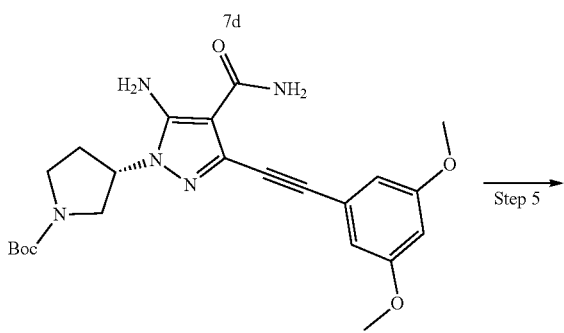

7e

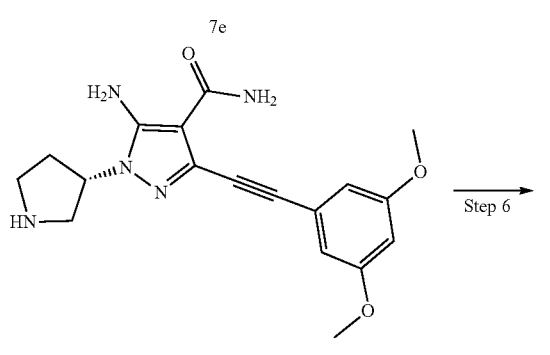

7f

7

Step 1

5-amino-3-bromo-1H-pyrazole-4-carbonitrile

The compound 5-amino-1H-pyrazole-4-carbonitrile 7a (20 g, 185 mmol) was dissolved in N,N-dimethylformamide (200 mL), and cooled to 0° C., next N-bromosuccinimide (34 g, 190 mmol) was added in portions, the temperature was raised to room temperature and stirred for 2 hours, the reaction solution was then poured into a sodium sulfite solution, extracted with ethyl acetate (200 mL×3), and then the phases were combined and dried over anhydrous sodium sulfate, the desiccant was removed through filtering, and the reaction system was concentrated under reduced pressure, the residue was purified by silica gel column chromatography (dichloromethane/methanol=20/1), so as to obtain the title product 5-amino-3-bromo-1H-pyrazole-4-carbonitrile 7b (32 g, yellow solid), and the yield was 93%.

MS m/z (ESI): 187/189[M+1]

Step 2

(S)-3-(5-amino-3-bromo-4-cyano-1H-pyrazol-1-yl)pyrrolidine-1-carboxylic Acid Tert-Butyl Ester A mixture of 5-amino-3-bromo-1H-pyrazole-4-carbonitrile 7b (10 g, 53.8 mmol), 3-(toluenesulfonyloxy)pyrrolidine-1-carboxylic acid tert-butyl ester (22 g, 64.5 mmol), cesium carbonate (58 g, 107.6 mmol) and acetonitrile (250 mL) was heated to 90° C. and reacted for 4 hours, and was then cooled to room temperature, filtered and the resulting filter cake was washed with dichloromethane, the filtrates were combined and concentrated under reduced pressure, the residue was purified by silica gel column chromatography (petroleum ether/ethyl acetate=5/1), so as to obtain the title product (S)-3-(5-amino-3-bromo-4-cyano-1H-pyrazol-1-yl)pyrrolidine-1-carboxylic acid tert-butyl ester 7c (5 g, yellow oil), and the yield was 26%.

MS m/z (ESI): 300/302[M+1-56]

Step 3

(S)-3-(5-amino-4-cyano-3-((3,5-dimethoxyphenyl)ethynyl)-1H-pyrazol-1-yl)pyrrolidine-1-carboxylic Acid Tert-Butyl Ester A mixture of (S)-3-(5-amino-3-bromo-4-cyano-1H-pyrazol-1-yl)pyrrolidine-1-carboxylic acid tert-butyl ester 7c (5 g, 14.1 mmol), cuprous iodide (0.6 g, 2.8 mmol), triethylamine (9 mL), [1,1'-bis(diphenylphosphino)ferrocene]palladium dichloride (2 g, 2.8 mmol) and N,N-dimethylformamide (150 mL) was heated to 80° C. under argon, and then 1-ethynyl-3,5-dimethoxybenzene (14 g, 84.5 mmol) was added in portions, next stirred for 2 hours, and then cooled to room temperature, poured the reaction solution into water, extracted with ethyl acetate (200 mL×3); next the organic phases were combined and dried over anhydrous sodium sulfate, the desiccant was removed by filtering, and the reaction system was concentrated under reduced pressure, the residue was purified by silica gel column chromatography (petroleum ether/ethyl acetate=5/1), so as to obtain the title product (S)-3-(5-amino-4-cyano-3-((3,5-dimethoxyphenyl)ethynyl)-1H-pyrazol-1-yl)pyrrolidine-1-carboxylic acid tert-butyl ester 7d (5 g, brown oil), and the yield was 81%.

MS m/z (ESI): 382[M+1-56]

Step 4

(S)-3-(5-amino-4-carbamoyl-3-((3,5-dimethoxyphenyl)ethynyl)-1H-pyrazol-1-yl)pyrrolidine-1-carboxylic Acid Tert-Butyl Ester A mixture of (S)-3-(5-Amino-4-cyano-3-((3,5-dimethoxyphenyl)ethynyl)-1H-pyrazol-1-yl)pyrrolidine-1-carboxylic acid tert-butyl ester 7d (5 g, 11.4 mmol), sodium hydroxide (1.5 g, 37.5 mmol, dissolved in 2 mL of water), ethanol (50 mL) and dimethyl sulfoxide (10 mL) was cooled to 0° C., added with hydrogen peroxide (20 mL), stirred at room temperature for 2 hours, the reaction solution was next poured into a sodium sulfite solution, extracted with ethyl acetate (100 mL×3), and the organic phases were combined and dried over anhydrous sodium sulfate, the desiccant was removed by filtering, and the reaction system was concentrated under reduced pressure, the residue was purified by silica gel column chromatography (petroleum ether/ethyl acetate=1/1), so as to obtain the title product (S)-3-(5-amino-4-carbamoyl-3-((3,5-dimethoxyphenyl)ethynyl)-1H-pyrazol-1-yl)pyrrolidine-1-carboxylic acid tert-butyl ester, and the yield was 96%.

MS m/z (ESI): 400[M+1-56]

Step 5

(S)-5-amino-3-((3,5-dimethoxyphenyl)ethynyl)-1-(pyrrolidin-3-yl)-1H-pyrazole-4-carboxamide The compound (S)-3-(5-amino-4-carbamoyl-3-((3,5-dimethoxyphenyl)ethynyl)-1H-pyrazol-1-yl)pyrrolidine-1-carboxylic acid tert-butyl ester 7e (5 g, 11 mmol) was dissolved in dichloromethane (100 mL), next added trifluoroacetic acid (15 mL), and then stirred at room temperature for 2 hours, and then concentrated under reduced pressure, so as to obtain the title product (S)-5-amino-3-((3,5-dimethoxyphenyl)ethynyl)-1-(pyrrolidin-3-yl)-1H-pyrazole-4-carboxamide 7f (7.1 g, brown oily substance, trifluoroacetate, crude), and the yield was >100%, the product was used in the next reaction without purification.

MS m/z (ESI): 356[M+1]

Step 6

(S)-1-(1-acryloylpyrrolidin-3-yl)-5-amino-3-((3,5-dimethoxyphenyl)ethynyl)-1H-pyrazole-4-carboxamide The compound (S)-5-amino-3-((3,5-dimethoxyphenyl)ethynyl)-1-(pyrrolidin-3-yl)-1H-pyrazole-4-carboxamide 7f (7.1 g, 11 mmol, trifluoroacetate, crude) was dissolved in tetrahydrofuran (50 mL), and cooled to 0° C., a saturated sodium bicarbonate solution (20 mL) and acryloyl chloride (900 mg, 10 mmol) were added sequentially, stirred for 30 minutes, the reaction solution was then poured into water (100 mL), and extracted with dichloromethane (100 mL×3), the organic phases were combined and dried over anhydrous sodium sulfate, the desiccant was removed by filtering, and the reaction system was concentrated under reduced pressure, the residue was purified by silica gel column chromatography (petroleum ether/ethyl acetate=1/2), so as to obtain the title product (S)-1-(1-acryloylpyrrolidin-3-yl)-5-amino-3-((3,5-dimethoxyphenyl)ethynyl)-1H-pyrazole-4-carboxamide 7 (1.9 g, white solid), and the yield was 42%.

MS m/z (ESI): 410[M+1]

$^1$H NMR (400 MHz, DMSO-d$_6$) δ 7.18 (brs, 1H), 6.75 (d, J=2.3 Hz, 2H), 6.69-6.55 (m, 3H), 6.20-6.14 (m, 1H), 5.72-5.67 (m, 1H), 5.03-4.91 (m, 1H), 4.01-3.96 (m, 1H), 3.84-3.70 (m, 7H), 3.66-3.60 (m, 1H), 3.55-3.48 (m, 1H), 2.36-2.21 (m, 2H).

Example 8

(S,E)-5-amino-3-((3,5-dimethoxyphenyl)ethynyl)-1-(1-(4-(dimethylamino)but-2-enoyl) pyrrolidin-3-yl)-1H-pyrazole-4-carboxamide

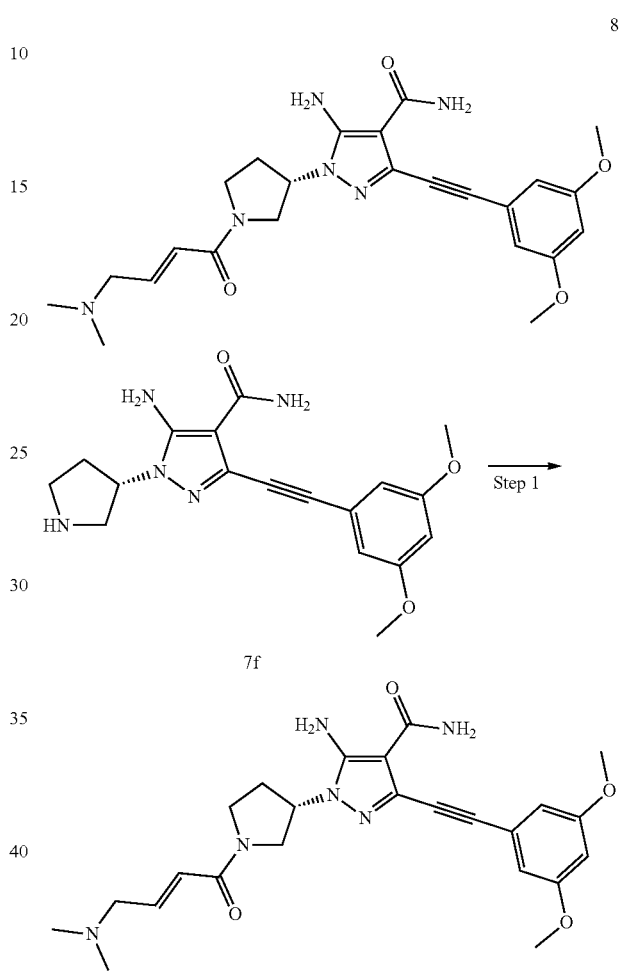

Step 1

(S,E)-5-amino-3-((3,5-dimethoxyphenyl)ethynyl)-1-(1-(4-(dimethylamino)but-2-enoyl) pyrrolidin-3-yl)-1H-pyrazole-4-carboxamide A mixture of (E)-4-(dimethylamino)but-2-enoic acid (23 mg, 0.14 mmol), O-(7-azabenzotriazol-1-yl)-N,N,N',N'-tetramethylurea hexafluorophosphate (HATU) (64 mg, 0.17 mmol), (S)-5-amino-3-((3,5-dimethoxyphenyl)ethynyl)-1-pyrrolidin-3-yl)-1H-pyrazole-4-carboxamide 7f (50 mg, 0.14 mmol), N,N-diisopropylethylamine (2 mL) and dichloromethane (3 mL) was stirred at room temperature for 1 hour, the reaction solution was poured into water and extracted with dichloromethane (20 mL×3), the organic phases were combined and dried over anhydrous sodium sulfate, the desiccant was removed by filtering, and the reaction system was concentrated under reduced pressure, the residue was purified by high performance liquid chromatography, so as to obtain the title product (S,E)-5-amino-3-((3,5-dimethoxyphenyl)ethynyl)-1-(1-(4-(dimethylamino)but-2-enoyl) pyrrolidin-3-yl)-1H-pyrazole-4-carboxamide 8 (2.4 mg, white solid, formate), and the yield was 4%.

MS m/z (ESI): 467[M+1]

$^1$H NMR (400 MHz, DMSO-d$_6$) δ 8.27 (brs, 1H), 7.20 (brs, 1H), 6.75 (d, J=2.3 Hz, 2H), 6.70-6.61 (m, 3H), 6.44-6.35 (m, 1H), 5.01-4.93 (m, 1H), 4.01-3.93 (m, 1H), 3.77 (s, 6H), 3.74-3.64 (m, 3H), 3.06-3.03 (m, 2H), 2.38-2.24 (m, 2H), 2.17-2.15 (m, 6H).

Example 9

(S)-5-amino-3-((3,5-dimethoxyphenyl)ethynyl)-1-(1-(2-fluoroacryloyl)pyrrolidin-3-yl)-1H-pyrazole-4-carboxamide

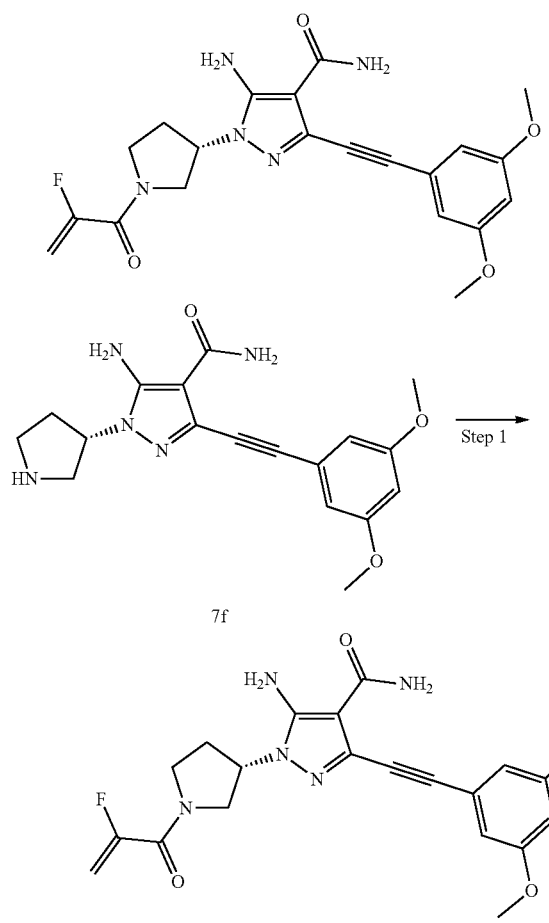

Step 1

(S)-5-amino-3-((3,5-dimethoxyphenyl)ethynyl)-1-(1-(2-fluoroacryloyl)pyrrolidin-3-yl)-1H-pyrazole-4-carboxamide The compound (S)-5-amino-3-((3,5-dimethoxyphenyl)ethynyl)-1-(pyrrolidin-3-yl)-1H-pyrazole-4-carboxamide 7f (50 mg, 0.14 mmol) and 2-fluoroacrylic acid (15 mg, 0.17 mmol) were dissolved in dichloromethane, next added N,N-diisopropylethylamine (54 mg, 0.42 mmol) and O-(7-azabenzotriazol-1-yl)-N,N,N',N'-tetramethyluronium hexafluorophosphate (HATU) (69 mg, 0.18 mmol), stirred at room temperature for 2 hours, the reaction mixture was then diluted with water (10 mL), extracted with dichloromethane (10 mL×3), and the organic phases were combined and dried over anhydrous sodium sulfate, the desiccant was removed by filtering, and the reaction system was concentrated under reduced pressure, the residue was purified by thin layer silica gel column chromatography (dichloromethane/methanol=20/1), so as to obtain the title product (S)-5-amino-3-((3,5-dimethoxyphenyl)ethynyl)-1-(1-(2-fluoroacryloyl)pyrrolidin-3-yl)-1H-pyrazole-4-carboxamide 9 (3.6 mg, white solid), and the yield was 6%.

MS m/z (ESI): 428 [M+1]

$^1$H NMR (400 MHz, CD$_3$OD) δ 6.62 (t, J=2.5 Hz, 2H), 6.47 (t, J=2.3 Hz, 1H), 5.39 (dd, J=47.2, 3.5 Hz, 1H), 5.16 (ddd, J=16.6, 5.7, 3.5 Hz, 1H), 4.86-4.81 (m, 1H), 4.02-3.91 (m, 2H), 3.87-3.72 (m, 2H), 3.71 (s, 6H), 2.34-2.23 (m, 2H).

Example 10

(S)-5-amino-1-(1-(but-2-ynyl)pyrrolidin-3-yl)-3-((3,5-dimethoxyphenyl)ethynyl)-1H-pyrazole-4-carboxamide

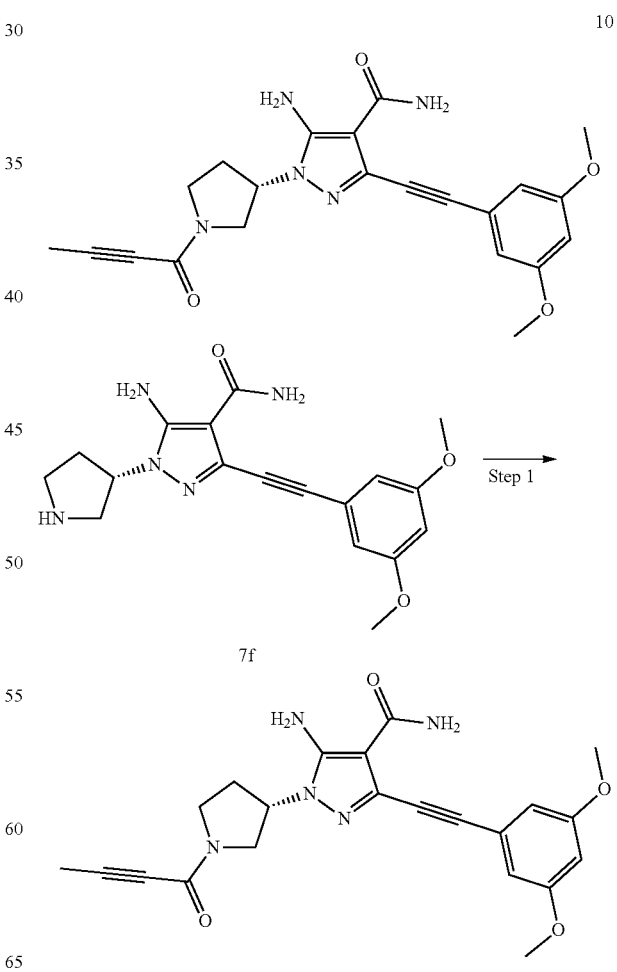

Step 1

(S)-5-amino-1-(1-(but-2-ynyl)pyrrolidin-3-yl)-3-((3,5-dimethoxyphenyl)ethynyl)-1H-pyrazole-4-carboxamide (S)-5-amino-3-((3,5-dimethoxyphenyl)ethynyl)-1-(pyrrolidin-3-yl)-1H-pyrazole-4-carboxamide 7f (50 mg, 0.14 mmol) and 2-butynoic acid (14 mg, 0.17 mmol) were dissolved in dichloromethane, next added N,N-diisopropylethylamine (54 mg, 0.42 mmol) and O-(7-azabenzotriazol-1-yl)-N,N,N',N'-tetramethyluronium hexafluorophosphate (HATU) (69 mg, 0.18 mmol), stirred at room temperature for 2 hours, the reaction mixture was then diluted with water (10 mL), extracted with dichloromethane (10 mL×3), and the organic phases were combined and dried over anhydrous sodium sulfate, the desiccant was removed by filtering, and the reaction system was concentrated under reduced pressure, the residue was purified by thin layer silica gel column chromatography (dichloromethane/methanol=20/1), so as to obtain the title product (S)-5-amino-1-(1-(but-2-ynyl)pyrrolidin-3-yl)-3-((3,5-dimethoxyphenyl)ethynyl)-1H-pyrazole-4-carboxamide 10 (5.1 mg, pale yellow solid), and the yield was 9%.

MS m/z (ESI): 422 [M+1]

$^1$H NMR (400 MHz, CD$_3$OD) δ 6.62 (t, J=2.1 Hz, 2H), 6.47 (t, J=2.2 Hz, 1H), 4.85-4.81 (m, 1H), 4.01-3.86 (m, 2H), 3.77-3.62 (m, 7.5H), 3.54-3.46 (m, 0.5H), 2.32-2.27 (m, 2H), 1.95-1.93 (m, 3H).

Example 11

(S,E)-5-amino-3-((3,5-dimethoxyphenyl)ethynyl)-1-(1-(4-methoxybut-2-enoyl)pyrrolidine-3-yl)-1H-pyrazole-4-carboxamide

11

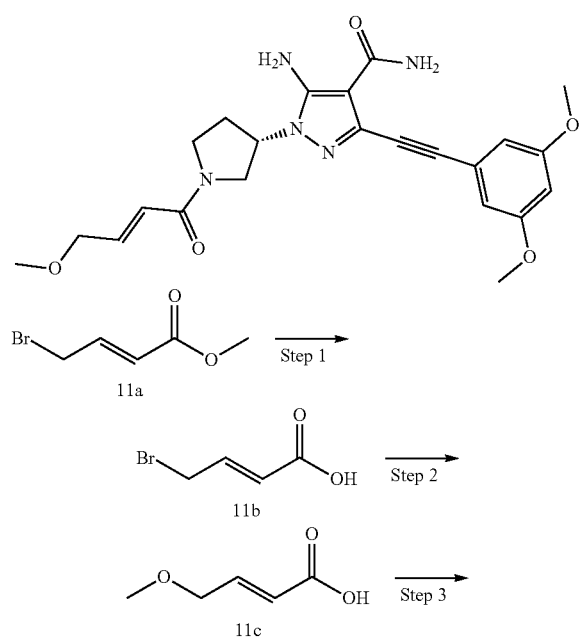

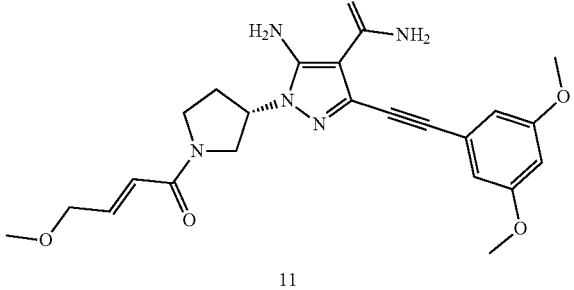

11

Step 1

(E)-4-bromobut-2-enoic Acid

Methyl (E)-4-bromobut-2-enoate 11a (3 g, 16.8 mmol), lithium hydroxide monohydrate (1.1 g, 25.3 mmol), tetrahydrofuran (50 mL) and water (50 mL) were mixed at 0° C. and stirred for 2 more hours; after completion of the reaction, tetrahydrofuran was washed away with petroleum ether, and the aqueous phase was adjusted to pH=1 with 2M hydrochloric acid, and then extracted with ethyl acetate (100 mL×2), after the organic phases were combined, the solvent was evaporated under reduced pressure, so as to obtain the title product (E) 4-bromobut-2-enoic acid 11b (2.3 g, yellow oily substance), and the yield was 83%.

MS m/z (ESI): 163[M−1]

Step 2

(E)-4-methoxybut-2-enoic Acid

The compound (E)-4-bromobut-2-enoic acid 11b (100 mg, 0.61 mmol) was dissolved in methanol (5 mL), a sodium methoxide in methanol (30%, 0.55 mL, 3.05 mmol) was added and then stirred for 15 hours, the reaction mixture was removed with the solvent under reduced pressure and then dissolved in water, next adjusted to pH=1 with dilute hydrochloric acid and then extracted with dichloromethane (10 mL×3), the organic phases were combined, and the solvent was evaporated under reduced pressure, so as to obtain the title product of (E)-4-methoxybut-2-enoic acid 11c (50 mg, yellow oily substance), and the yield was 71%.

$^1$H NMR (400 MHz, CDCl$_3$) δ 7.13-7.03 (m, 1H), 6.15-6.07 (m, 1H), 4.18-4.11 (m, 2H), 3.48-3.38 (s, 3H).

Step 3

(S,E)-5-amino-3-((3,5-dimethoxyphenyl)ethynyl)-1-(1-(4-methoxybut-2-enoyl)pyrrolidine-3-yl)-1H-pyrazole-4-carboxamide The compound (E)-4-methoxybut-2-enoic acid 11c (22 mg, 0.19 mmol), diisopropylethylamine (67 mg, 0.52 mmol), (S)-5-amino-3-((3,5-dimethoxyphenyl)ethynyl)-1-(pyrrolidin-3-yl)-1H-pyrazole-4-carboxamide 7f (50 mg, 0.13 mmol), 2-(7-Oxobenzotriazole)-N,N,N',N'-tetramethyluronium hexafluorophosphate (72 mg, 0.19 mmol) and N,N-dimethylformamide (10 mL) were mixed and stirred for 2 hours, the solvent is removed under reduced pressure, and the residue was dissolved in ethyl acetate (30 mL), and then washed sequentially with water and saturated brine, the solvent was removed under reduced pressure, and the residue was purified by silica gel column chromatography (dichloromethane/methanol=20/1), so as to obtain the title product of (S,E)-5-amino-3-((3,5-dimethoxyphenyl)ethynyl)-1-(1-(4-methoxybut-2-enoyl)pyrrolidine-3-yl)-1H-pyrazole-4-carboxamide (30 mg, white solid), and the yield was 51%.

MS m/z (ESI): 454[M+1]

¹H NMR (400 MHz, CDCl₃) δ 6.98 (d, J=15.3 Hz, 1H), 6.86 (brs, 1H), 6.72 (d, J=2.1 Hz, 2H), 6.54 (s, 1H), 6.39 (dd, J=27.7, 16.0 Hz, 1H), 5.54 (brs, 1H), 4.73-4.70 (m, 1H), 4.14-4.12 (m, 2H), 4.05-4.00 (m, 2H), 3.95-3.93 (m, 1H), 3.82 (s, 6H), 3.77-3.68 (m, 1H), 3.43 (d, J=10.1 Hz, 3H), 2.72 (brs, 0.5H), 2.54 (brs, 0.5H), 2.43-2.35 (m, 1H).

Example 12

(S)-5-amino-1-(1-cyanopyrrolidin-3-yl)-3-((3,5-dimethoxyphenyl)ethynyl)-1H-pyrazole-4-carboxamide

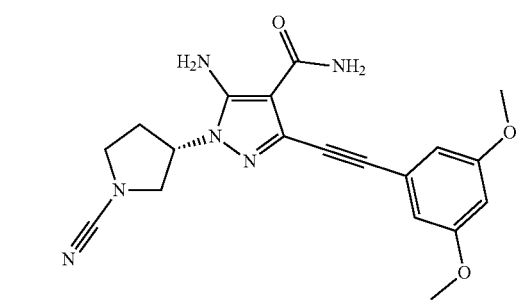

12

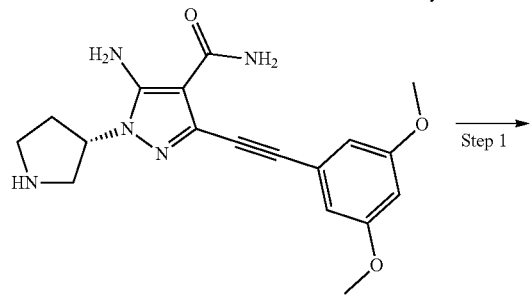

7f

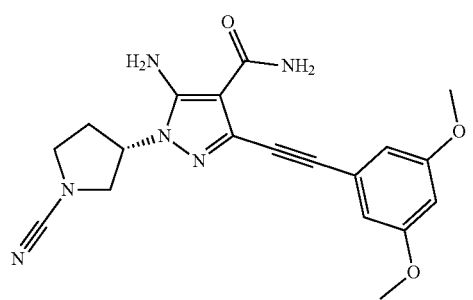

12

Step 1

(S)-5-amino-1-(1-cyanopyrrolidin-3-yl)-3-((3,5-dimethoxyphenyl)ethynyl)-1H-pyrazole-4-carboxamide The compound (S)-5-amino-3-((3,5-dimethoxyphenyl)ethynyl)-1-(pyrrolidin-3-yl)-1H-pyrazole-4-carboxamide 7f (50 mg, 0.14 mmol) was dissolved in tetrahydrofuran (2 mL), and then added triethylamine (1 mL), cooled to 0° C., added cyanogen bromide (17 mg, 0.15 mmol), stirred at 0° C. for 2 hours, the reaction temperature was next raised to room temperature and continued stirring for 2 hours, the reaction mixture was concentrated under reduced pressure, and the residue was purified by thin layer silica gel chromatography (dichloromethane/methanol=15/1), so as to obtain the title product (S)-5-amino-1-(1-cyanopyrrolidin-3-yl)-3-((3,5-dimethoxyphenyl)ethynyl)-1H-pyrazole-4-carboxamide 12 (18 mg, white solid), and the yield was 34%.

MS m/z (ESI): 381[M+1]

¹H NMR (400 MHz, CDCl₃) δ 6.77 (brs, 1H), 6.68 (d, J=1.9 Hz, 2H), 6.50 (s, 1H), 5.75 (s, 2H), 5.67 (brs, 1H), 4.79-4.73 (m, 1H), 3.84-3.73 (m, 9H), 3.61-3.53 (m, 1H), 2.53-2.43 (m, 1H), 2.37-2.26 (m, 1H).

Examples 13 to 16 were synthesized with reference to the operational steps of Example 7:

Example 13

(R)-1-(1-acryloylpyrrolidin-3-yl)-5-amino-3-((3,5-dimethoxyphenyl)ethynyl)-1H-pyrazole-4-carboxamide

13

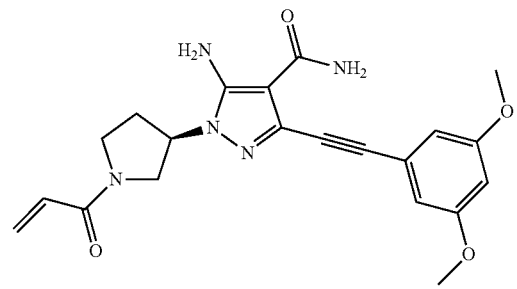

MS m/z (ESI): 410[M+1]

¹H NMR (400 MHz, CD₃OD) δ 6.73 (d, J=1.9 Hz, 2H), 6.71-6.60 (m, 1H), 6.58 (brs, 1H), 6.32 (dd, J=16.8, 1.7 Hz, 1H), 5.84-5.74 (m, 1H), 5.04-4.91 (m, 1H), 4.09 (m, 0.5H), 3.98 (td, J=11.1, 4.0 Hz, 1H), 3.91 (dd, J=7.8, 5.6 Hz, 1H), 3.86 (dd, J=9.9, 4.4 Hz, 1H), 3.81 (s, 6H), 3.73-3.63 (m, 0.5H), 2.47 (dd, J=13.2, 6.7 Hz, 1H), 2.38 (dd, J=13.6, 7.0 Hz, 1H).

Example 14

1-(1-acryloylazetidin-3-yl)-5-amino-3-((3,5-dimethoxyphenyl)ethynyl)-1H-pyrazole-4-carboxamide

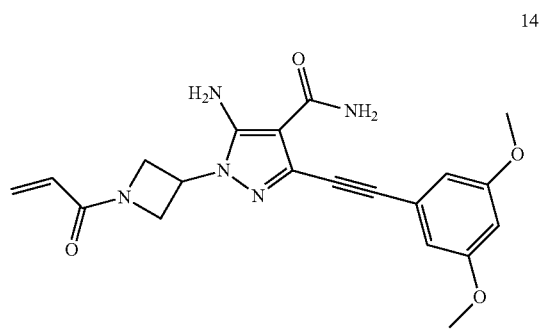 [SMILES: C=CC(=O)N1CC(n2nc(C#Cc3cc(OC)cc(OC)c3)c(C(N)=O)c2N)C1]

MS m/z (ESI): 396[M+1]

¹H NMR (400 MHz, CD₃OD) δ 6.75 (d, J=2.3 Hz, 2H), 6.60 (t, J=2.2 Hz, 1H), 6.45-6.28 (m, 2H), 5.80 (dd, J=10.1, 2.1 Hz, 1H), 5.29-5.21 (m, 1H), 4.79-4.64 (m, 2H), 4.54-4.47 (m, 1H), 4.46-4.39 (m, 1H), 3.82 (s, 6H).

Example 15

1-(1-acryloylpiperidin-4-yl)-5-amino-3-((3,5-dimethoxyphenyl)ethynyl)-1H-pyrazole-4-carboxamide

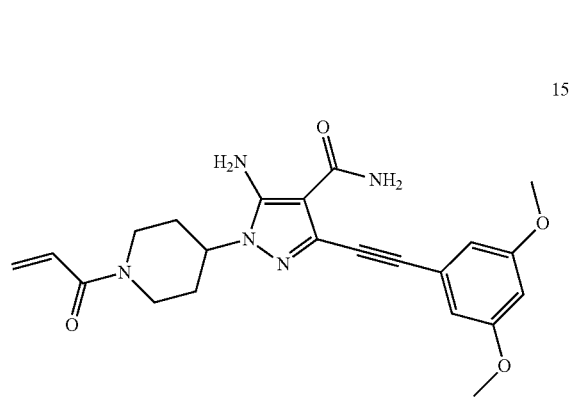 [SMILES: C=CC(=O)N1CCC(n2nc(C#Cc3cc(OC)cc(OC)c3)c(C(N)=O)c2N)CC1]

MS m/z (ESI): 424[M+1]

¹H NMR (400 MHz, CD₃OD) δ 6.88-6.78 (m, 1H), 6.73 (d, J=2.2 Hz, 2H), 6.58 (t, J=2.2 Hz, 1H), 6.24 (dd, J=16.8, 1.7 Hz, 1H), 5.78 (dd, J=10.7, 1.7 Hz, 1H), 4.73 (d, J=13.2 Hz, 1H), 4.47-4.36 (m, 1H), 4.30 (d, J=13.3 Hz, 1H), 3.81 (s, 6H), 3.32-3.24 (m, 1H), 2.91 (t, J=9.9 Hz, 1H), 2.02 (d, J=4.5 Hz, 4H).

Example 16

1-((1-acryloylpyrrolidin-3-yl)methyl)-5-amino-3-((3,5-dimethoxyphenyl)ethynyl)-1H-pyrazole-4-carboxamide

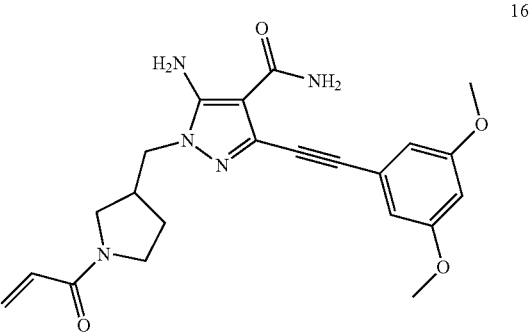 [SMILES: C=CC(=O)N1CCC(Cn2nc(C#Cc3cc(OC)cc(OC)c3)c(C(N)=O)c2N)C1]

MS m/z (ESI): 424[M+1]

¹H NMR (400 MHz, CD₃OD) δ 6.73 (s, 2H), 6.66-6.55 (m, 2H), 6.28 (d, J=16.7 Hz, 1H), 5.75 (d, J=10.4 Hz, 1H), 4.13-3.99 (m, 2H), 3.82 (s, 6H), 3.78-3.61 (m, 2H), 3.48 (dd, J=14.8, 7.4 Hz, 1H), 3.39-3.34 (m, 1H), 2.94-2.75 (m, 1H), 2.20-2.02 (m, 1H), 1.94-1.71 (m, 1H).

Example 17

(S)-1-(1-acryloylpyrrolidin-3-yl)-5-amino-3-((2-fluoro-3,5-dimethoxyphenyl)ethynyl)-1H-pyrazole-4-carboxamide

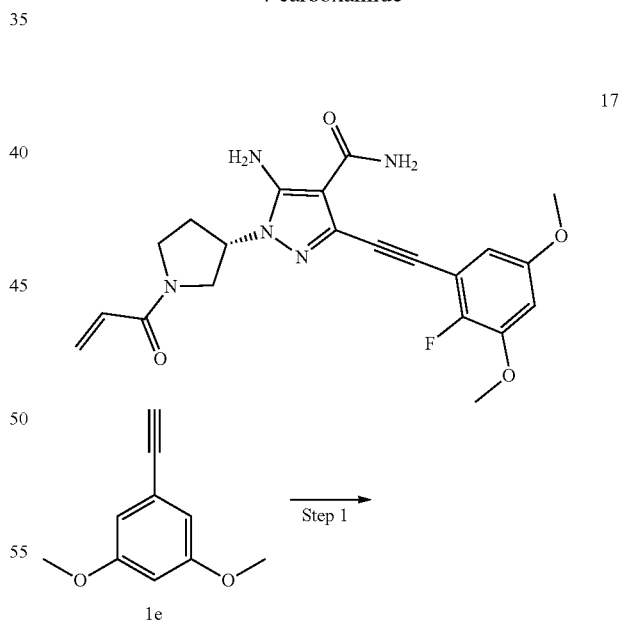

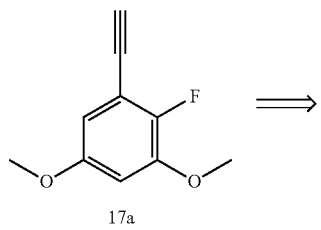

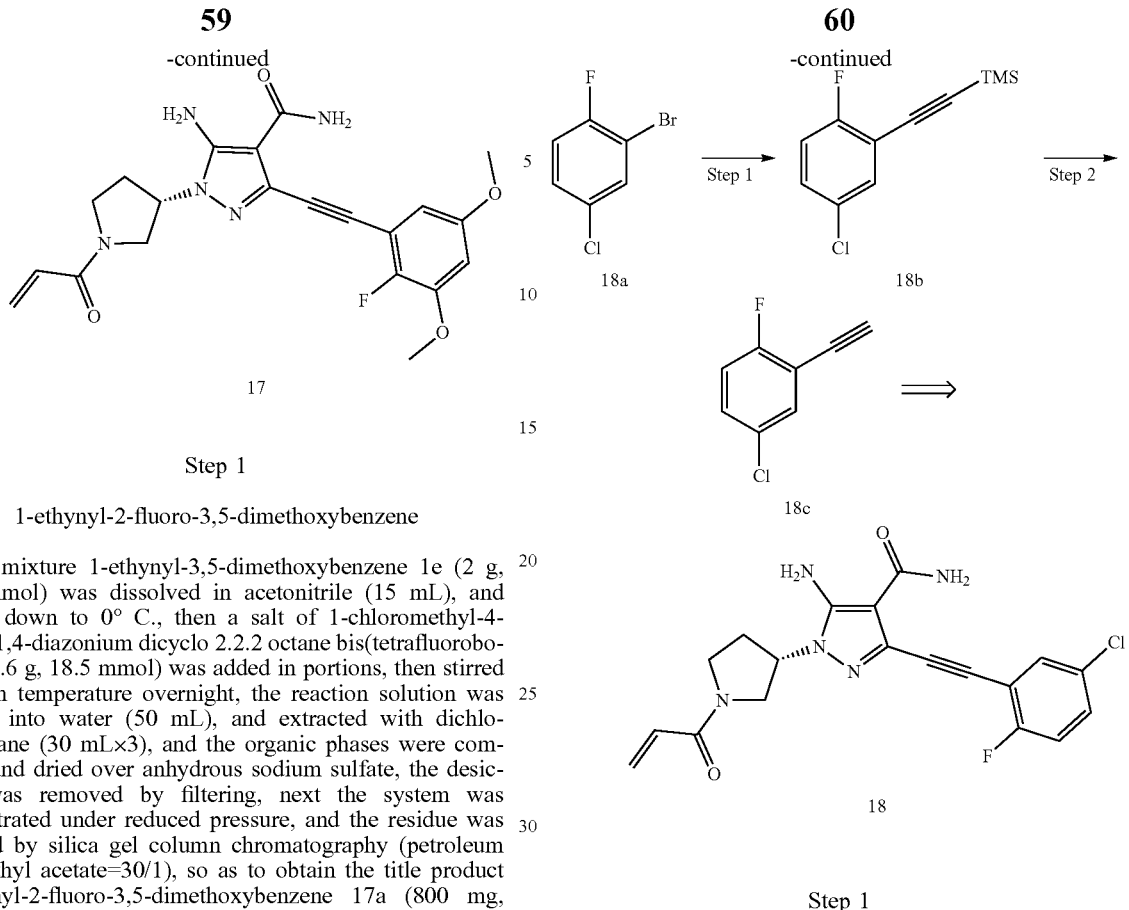

Step 1

1-ethynyl-2-fluoro-3,5-dimethoxybenzene

The mixture 1-ethynyl-3,5-dimethoxybenzene 1e (2 g, 12.3 mmol) was dissolved in acetonitrile (15 mL), and cooled down to 0° C., then a salt of 1-chloromethyl-4-fluoro-1,4-diazonium dicyclo 2.2.2 octane bis(tetrafluoroborate) (6.6 g, 18.5 mmol) was added in portions, then stirred at room temperature overnight, the reaction solution was poured into water (50 mL), and extracted with dichloromethane (30 mL×3), and the organic phases were combined and dried over anhydrous sodium sulfate, the desiccant was removed by filtering, next the system was concentrated under reduced pressure, and the residue was purified by silica gel column chromatography (petroleum ether/ethyl acetate=30/1), so as to obtain the title product 1-ethynyl-2-fluoro-3,5-dimethoxybenzene 17a (800 mg, yellow solid), and the yield was 36%.

$^1$H NMR (400 MHz, CDCl$_3$) δ 6.46 (dd, J=6.9, 2.9 Hz, 1H), 6.41 (dd, J=4.5, 3.0 Hz, 1H), 3.78 (s, 3H), 3.69 (s, 3H), 3.22 (s, 1H).

Example 17 was then synthesized by referring to the procedure of the first to sixth steps of Example 7 provided above, but in the third step, 1-ethynyl-2-fluoro-3,5-dimethoxybenzene was used to substitute 1-ethynyl-3,5-dimethoxybenzene.

MS m/z (ESI): 428[M+1]

$^1$H NMR (400 MHz, CDCl$_3$) δ 7.00 (brs, 1H), 6.59-6.57 (m, 2H), 6.49-6.39 (m, 2H), 5.74-5.70 (m, 1H), 5.52 (d, J=8.5 Hz, 2H), 5.35 (brs, 1H), 4.73-4.64 (m, 1H), 4.07-3.90 (m, 3H), 3.88 (s, 3H), 3.78 (d, J=5.3 Hz, 3H), 3.75-3.67 (m, 1H), 2.72-2.67 (m, 0.5H), 2.54-2.31 (m, 1.5H).

Example 18

(S)-1-(1-acryloylpyrrolidin-3-yl)-5-amino-3-((5-chloro-2-fluorophenyl)ethynyl)-1H-pyrazole-4-carboxamide

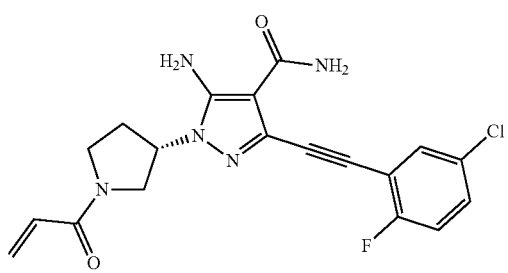

Step 1

((2-fluoro-5-chlorophenyl)ethynyl)trimethylsilane

2-Fluoro-5-chlorobromobenzene 18a (11.0 g, 52.8 mmol), ethynyltrimethylsilane (7.7 g, 79 mmol) and triethylamine (60 mL) were mixed together, and then cuprous iodide (100 mg, 0.53 mmol) and ditriphenylphosphine palladium chloride (1.86 g, 2.65 mmol) were added, the reaction mixture was heated to 80° C. under a nitrogen atmosphere and stirring was continued for 4 hours, after the reaction was completed, the solvent was removed from the solution under reduced pressure, the residue was purified by silica gel column chromatography (petroleum ether/ethyl acetate=100/1), so as to obtain the title product ((2-fluoro-5-chlorophenyl)ethynyl)trimethylsilane 18b (11.0 g, yellow oily substance), and the yield was 90%.

$^1$H NMR (400 MHz, CDCl$_3$) δ 7.45 (dd, J=6.0, 2.7 Hz, 1H), 7.28-7.22 (m, 1H), 7.02 (t, J=8.8 Hz, 1H), 0.29 (s, 9H).

Step 2

4-chloro-2-ethynyl-1-fluorobenzene ((2-fluoro-5-chlorophenyl)ethynyl)trimethylsilane 18b (11.0 g, 48 mmol), potassium carbonate (8.1 g, 58 mmol), dichloromethane (80 mL) and methanol (40 mL) were mixed together, and stirred at room temperature for 18 hours, after the reaction was finished, the solvent was removed from the solution under reduced pressure, the residue was purified by silica gel column chromatography (petroleum ether/ethyl acetate=100/1) so as to obtain the title product 4-chloro-2-ethynyl-1-fluorobenzene 18c (5.5 g, yellow solid), and the yield was 74%.

¹H NMR (400 MHz, CDCl₃) δ 7.45 (dd, J=6.0, 2.7 Hz, 1H), 7.31-7.27 (m, 1H), 7.04 (t, J=8.0, 1H), 3.35 (s, 1H).

Example 18 was then synthesized by referring to the procedure of the first to sixth steps of Example 7 provided above, but in the third step, 4-chloro-2-ethynyl-1-fluorobenzene was used to substitute 1-ethynyl-3,5-dimethoxybenzene.

MS m/z (ESI): 402[M+1]

¹H NMR (400 MHz, CD₃OD) δ 7.62-7.61 (m, 1H), 7.47-7.45 (m, 1H), 7.24 (t, J=9.0 Hz, 1H), 6.69-6.56 (m, 1H), 6.30 (d, J=16.8 Hz, 1H), 5.77 (t, J=9.2 Hz, 1H), 5.02-1.91 (m, 1H), 4.09-3.95 (m, 2H), 3.84-3.78 (m, 2H), 2.46 (dd, J=13.1, 6.6 Hz, 1H), 2.37 (dd, J=13.6, 6.9 Hz, 1H).

Example 19

(S)-1-(1-acryloylpyrrolidin-3-yl)-5-amino-3-((2-chloro-5-(methylcarbamoyl)phenyl)ethynyl)-1H-pyrazole-4-carboxamide

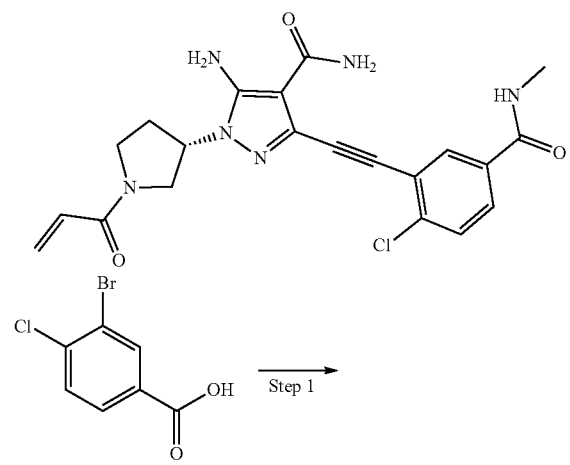

19

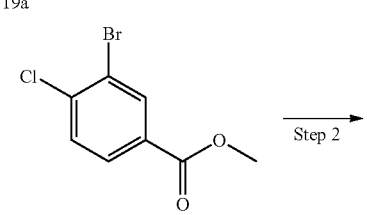

19a

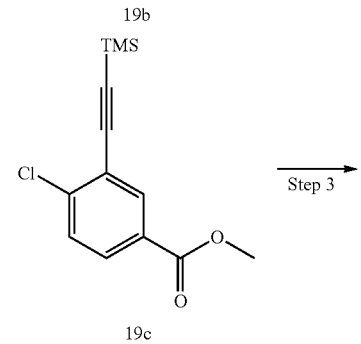

19b

19c

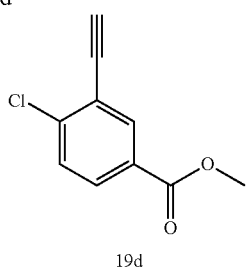

19d

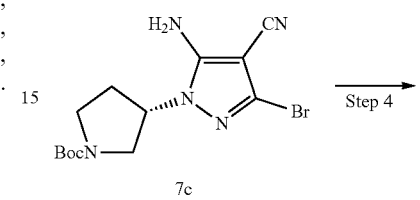

7c

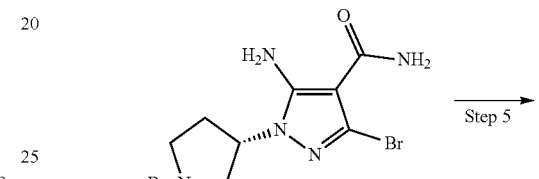

19e

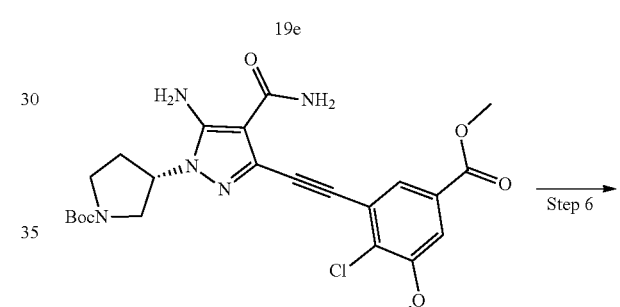

19f

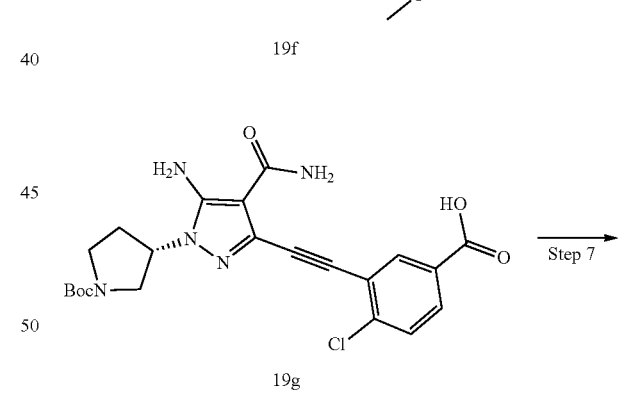

19g

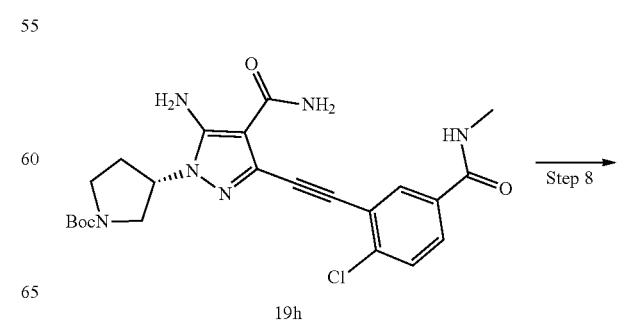

19h

-continued

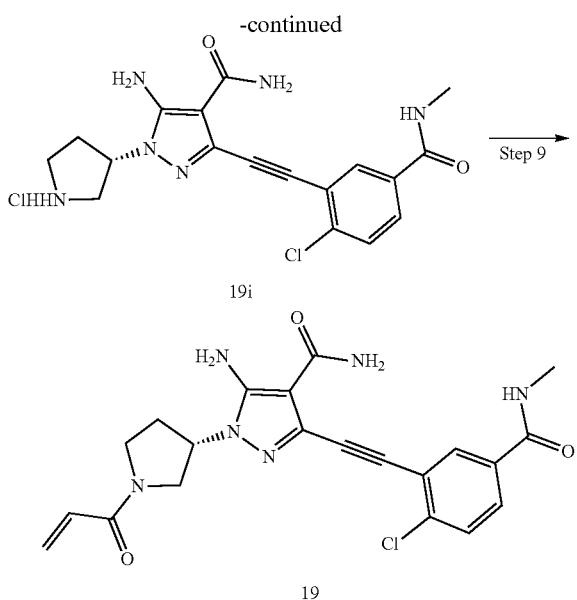

19i

19

Step 1

Methyl 4-chloro-3-bromobenzoate

4-Chloro-3-bromobenzoic acid 19a (2 g, 8.5 mmol) was dissolved in methanol (400 mL) and cooled to 0° C., next acetyl chloride (2.3 g, 30 mmol) was then added dropwise and stirring was continued for 18 hours, after the reaction was finished, the solvent was removed under reduced pressure, and the residue was purified by silica gel column chromatography (petroleum ether/ethyl acetate=10/1), so as to obtain the title product methyl 4-chloro-3-bromobenzoate 19b (1.2 g, yellow solid), and the yield was 57%.

$^1$H NMR (400 MHz, CDCl$_3$) δ 8.31 (d, J=1.9 Hz, 1H), 7.93 (dd, J=8.3, 1.9 Hz, 1H), 7.55 (d, J=8.3 Hz, 1H), 3.95 (s, 3H).

Step 2

Methyl 4-chloro-3-((trimethylsilyl)ethynyl)benzoate

The compound methyl 4-chloro-3-bromobenzoate 19b (1.2 g, 4.8 mmol), trimethylsilylacetylene (0.95 g, 9.7 mmol), palladium acetate (108 mg, 0.48 mmol), triphenylphosphine (254 mg, 0.97 mmol), cuprous iodide (185 mg, 0.97 mmol) and triethylamine (25 mL) were mixed in a sealed tube, and heated and stirred at 100° C. for 15 hours, after the reaction is completed, the solvent was removed under reduced pressure, and the residue was purified by silica gel column chromatography (petroleum ether/ethyl acetate=10/1), so as to obtain the title product methyl 4-chloro-3-((trimethylsilyl)ethynyl)benzoate 19c (1 g, yellow solid), and the yield was 78%.

$^1$H NMR (400 MHz, CDCl$_3$) δ 8.19 (d, J=2.0 Hz, 1H), 7.91 (dd, J=8.4, 2.1 Hz, 1H), 7.48 (d, J=8.4 Hz, 1H), 3.94 (s, 3H), 0.30 (s, 9H).

Step 3

Methyl 4-chloro-3-ethynylbenzoate

Methyl 4-chloro-3-((trimethylsilyl)ethynyl)benzoate 19c (1 g, 3.76 mmol) was dissolved in methanol (20 mL), potassium carbonate (1.04 g, 7.52 mmol) was then added, after stirring at room temperature for 1 hour, the solvent was removed under reduced pressure, and the residue was washed with water and then filtered, so as to obtain the title product methyl 4-chloro-3-ethynylbenzoate 19d (380 mg, yellow solid), and the yield was 52%.

$^1$H NMR (400 MHz, CDCl$_3$) δ 8.23 (d, J=2.1 Hz, 1H), 7.96 (dd, J=8.4, 2.0 Hz, 1H), 7.51 (d, J=8.4 Hz, 1H), 3.95 (s, 3H), 3.44 (s, 1H).

Step 4

(S)-3-(5-amino-3-bromo-4-carbamoyl-1H-pyrazol-1-yl)pyrrolidine-1-carboxylic Acid Tert-Butyl Ester Compound (S)-3-(5-amino-3-bromo-4-cyano-1H-pyrazol-1-yl)pyrrolidine-1-carboxylic acid tert-butyl ester 7c (2.20 g, 6.2 mmol), an aqueous solution of sodium hydrooxide (0.5 M, 12.4 mL, 6.2 mmol), an aqueous solution of hydrogen peroxide (30%, 15 mL) and dimethyl sulfoxide (30 mL) were mixed together, after stirring at room temperature for 2 hours, the reaction was diluted with saturated brine (50 mL), and then extracted with ethyl acetate (50 mL×3), then the organic phases were combined, the solvent was removed under reduced pressure, and the residue was purified by silica gel column chromatography (dichloromethane/methanol=100/1 to 20/1), so as to obtain the title product (S)-3-(5-amino-3-bromo-4-carbamoyl-1H-pyrazol-1-yl)pyrrolidine-1-carboxylic acid tert-butyl ester 19e (1.92 g, light yellow solid), and the yield was 83%.

MS m/z (ESI): 374[M+1]

Step 5

(S)-3-(5-amino-4-carbamoyl-3-((2-chloro-5-(carbomethoxy <methoxycarbonyl>)phenyl)ethynyl)-1H-pyrazole-1-yl)pyrrolidine-1-carboxylic Acid Tert-Butyl Ester (S)-3-(5-amino-3-bromo-4-carbamoyl-1H-pyrazol-1-yl)pyrrolidine-1-carboxylic acid tert-butyl ester 19e (770 mg, 2.1 mmol), triethylamine (6 mL), 1,1'-bisdiphenylphosphinoferrocene palladium dichloride (307 mg, 0.42 mmol), cuprous iodide (80 mg, 0.42 mmol) and N,N-dimethylformamide (20 mL) were mixed, deoxygenated, and then heated to 90° C. under argon atmosphere, next a solution of methyl 4-chloro-3-ethynylbenzoate 19d (3.20 g, 16.5 mmol) in N,N-dimethylformamide (2 mL) was added dropwise, and stirring continued for 12 hours, the solvent was removed under reduced pressure, and the residue was purified by silica gel column chromatography (dichloromethane/methanol=20/1), so as to obtain the title product (S)-3-(5-amino-4-carbamoyl-3-((2-chloro-5-(carbomethoxy <methoxycarbonyl>)phenyl)ethynyl)-1H-pyrazole-1-yl)pyrrolidine-1-carboxylic acid tert-butyl ester 19f (420 mg, yellow solid), and the yield was 41%.

MS m/z (ESI): 488[M+1]

Step 6

(S)-3-((5-amino-1-(1-(tert-butoxycarbonyl)pyrrolidin-3-yl)-4-carbamoyl-1H-pyrazol-3-yl)ethynyl)-4-chlorobenzoic Acid (S)-3-(5-amino-4-carbamoyl-3-((2-chloro-5-(carbomethoxy <methoxycarbonyl>)phenyl)ethynyl)-1H-pyrazole-1-yl)pyrrolidine-1-carboxylic acid tert-butyl ester 19f (100 mg, 0.2 mmol) was dissolved in a mixed solvent of methanol (4 mL) and water (4 mL), sodium hydroxide (25 mg, 0.61 mmol) was then added and stirring was continued for 2 hours, after the reaction was completed, the organic solvent was removed under reduced pressure, and the residue was adjusted to pH=4 to 5 with hydrochloric acid (1M), and then extracted with ethyl acetate (30 mL×2), the resulting organic phases were combined and washed with saturated brine, and then dried over anhydrous sodium sulfate, and filtered, the filtrate was removed with solvent under reduced pressure, so as to obtain the title product (S)-3-((5-amino-1-(1-(tert-butoxycarbonyl)pyrrolidin-3-yl)-4-carbamoyl-1H-pyrazol-3-yl)ethynyl)-4-chlorobenzoic acid 19 g (80 mg, brown solid), and the yield was 84%.

MS m/z (ESI): 418[M+H−56]

Step 7

(S)-3-(5-amino-4-carbamoyl-3-((2-chloro-5-(methylcarbamoyl)phenyl)ethynyl)-1H-pyrazol-1-yl)pyrrolidine-1-carboxylic Acid Tert-Butyl Ester (S)-3-((5-amino-1-(1-(tert-butoxycarbonyl)pyrrolidin-3-yl)-4-carbamoyl-1H-pyrazol-3-yl)ethynyl)-4-chlorobenzoic acid 19 g (80 mg, 0.17 mmol) was dissolved in N,N-dimethylformamide (2.5 mL), then methylamine hydrochloride (34 mg, 0.50 mmol), diisopropylethylamine (129 mg, 1 mmol) and 2-(7-benzotriazole)-N,N,N',N'-tetramethylurea hexafluorophosphate (64 mg, 0.17 mmol) were added sequentially, the reaction was stirred at room temperature for 2 hours and then quenched with water, next extracted with ethyl acetate (20 mL×3), the organic phases were combined, the solvent was removed under reduced pressure, and the residue was purified by silica gel column chromatography (petroleum ether/ethyl acetate=100/1 to 0/1), so as to obtain the title product (S)-3-(5-amino-4-carbamoyl-3-((2-chloro-5-(methylcarbamoyl)phenyl)ethynyl)-1H-pyrazol-1-yl)pyrrolidine-1-carboxylic acid tert-butyl ester 19h (41 mg, brown solid), and the yield was 50%.

MS m/z (ESI): 387[M+H-Boc]

Step 8

(S)-5-amino-3-((2-chloro-5-(methylcarbamoyl)phenyl)ethynyl)-1-(pyrrolidin-3-yl)-1H-pyrazole-4-formamide Hydrochloride (S)-3-(5-amino-4-carbamoyl-3-((2-chloro-5-(methylcarbamoyl)phenyl)ethynyl)-1H-pyrazol-1-yl)pyrrolidine-1-carboxylic acid tert-butyl ester 19h (40 mg, 0.08 mmol) was dissolved in ethyl acetate (5 mL), then a solution of hydrogen chloride in ethanol (33%, 3 mL) was added and stirred at room temperature for 1 hour, after the reaction was completed, the solvent was removed under reduced pressure, so as to obtain the title product (S)-5-amino-3-((2-chloro-5-(methylcarbamoyl)phenyl)ethynyl)-1-(pyrrolidin-3-yl)-1H-pyrazole-4-formamide hydrochloride 19i (40 mg, crude, brown solid), and the product was used directly in the next step without further purification.

MS m/z (ESI): 387[M+H]

Step 9

(S)-1-(1-acryloylpyrrolidin-3-yl)-5-amino-3-((2-chloro-5-(methylcarbamoyl)phenyl)ethynyl)-1H-pyrazole-4-carboxamide Compound (S)-5-amino-3-((2-chloro-5-(methylcarbamoyl)phenyl)ethynyl)-1-(pyrrolidin-3-yl)-1H-pyrazole-4-formamide hydrochloride 19i (40 mg, 0.08 mmol, crude), acryloyl chloride (7.5 mg, 0.08 mmol), an aqueous solution of potassium carbonate (0.4 M, 1.0 mL, 0.4 mmol) and tetrahydrofuran (5 mL) were mixed at 0° C., and stirred at this temperature for 0.5 hours, next extracted with ethyl acetate (20 mL×2), the organic phases were combined and dried over anhydrous sodium sulfate, the desiccant was removed by filtering, the solvent was removed under reduced pressure, and the residue was purified by silica gel column chromatography (dichloromethane/methanol=100/1 to 10/1), so as to obtain the title product (S)-1-(1-acryloylpyrrolidin-3-yl)-5-amino-3-((2-chloro-5-(methylcarbamoyl)phenyl)ethynyl)-1H-pyrazole-4-carboxamide 19 (18 mg, white solid), and the yield was 51% in two steps.

MS m/z (ESI): 441[M+H]

$^1$H NMR (400 MHz, DMSO-d$_6$) δ 8.65 (s, 1H), 8.18 (s, 1H), 7.90 (d, J=8.0 Hz, 1H), 7.72 (d, J=8.3 Hz, 1H), 7.43 (s, 1H), 6.70-6.62 (m, 4H), 6.19-6.15 (m, 1H), 5.70 (t, J=10.2 Hz, 1H), 5.03-4.94 (m, 1H), 3.80-3.54 (m, 4H), 2.78 (d, J=3.8 Hz, 3H), 2.36-2.25 (m, 2H).

Example 20

(S)-1-(1-acryloylpyrrolidin-3-yl)-5-amino-3-((3-methoxy-5-(methylcarbamoyl)phenyl)ethynyl)-1H-pyrazole-4-carboxamide

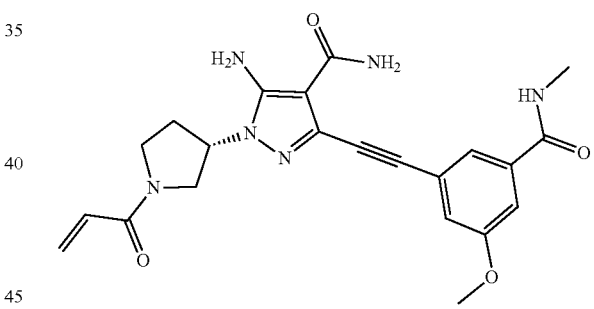

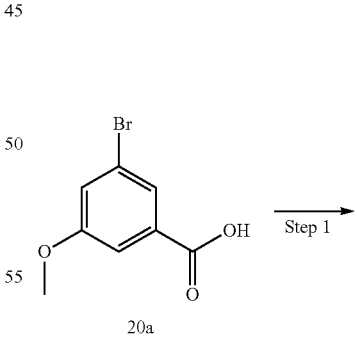

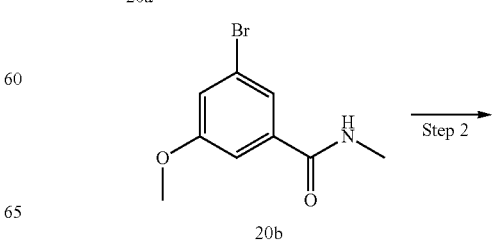

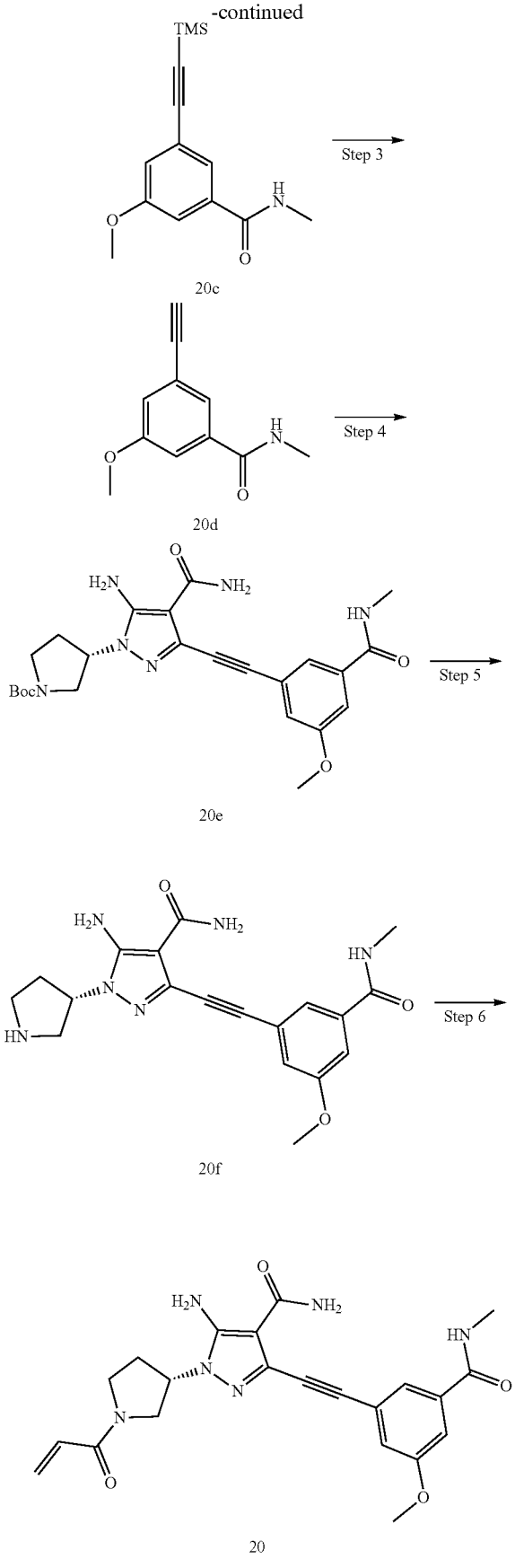

Step 1

3-bromo-5-methoxy-N-methylbenzamide

3-Bromo-5-methoxybenzoic acid 20a (500 mg, 2.17 mmol) was dissolved in N,N-dimethylformamide (15 mL), then methylamine hydrochloride (291 mg, 4.35 mmol), diisopropylethylamine (1.12 g, 8.68 mmol) and 2-(7-benzotriazole)-N,N,N',N'-tetramethylurea hexafluorophosphate (1.24 g, 3.26 mmol) were sequentially added, the reaction system was stirred at room temperature for 2 hours and then quenched with water, the solvent was removed under reduced pressure, and the residue was purified by silica gel column chromatography (petroleum ether/ethyl acetate=1/1), so as to obtain the title product 3-bromo-5-methoxy-N-methylbenzamide 20b (500 mg, white solid), and the yield was 95%.

MS m/z (ESI): 244[M+H]

Step 2

3-methoxy-N-methyl-5-((trimethylsilyl)ethynyl) benzamide

The compound 3-bromo-5-methoxy-N-methylbenzamide 20b (500 mg, 2.1 mmol), trimethylsilylacetylene (302 mg, 3.1 mmol), palladium acetate (47 mg, 0.21 mmol), triphenyl phosphine (110 mg, 0.42 mmol), cuprous iodide (80 mg, 0.42 mmol) and triethylamine (20 mL) were mixed in a sealed tube, and then heated to 100° C., and stirred for 15 hours, after the reaction is completed, the solvent was removed under reduced pressure, and the residue was purified by silica gel column chromatography (petroleum ether/ethyl acetate=1/1), so as to obtain the title product 3-methoxy-N-methyl-5-((trimethylsilyl)ethynyl)benzamide, 20c (220 mg, yellow solid), and the yield was 41%.

MS m/z (ESI): 262[M+H]

Step 3

3-ethynyl-5-methoxy-N-methylbenzamide

3-Methoxy-N-methyl-5-((trimethylsilyl)ethynyl)benzamide 20c (220 mg, 0.84 mmol) was dissolved in methanol (8 mL), potassium carbonate (233 mg, 1.68 mmol) was then added, after stirring at room temperature for 1 hour, the solvent was removed under reduced pressure, and the residue was purified by silica gel column chromatography (petroleum ether/ethyl acetate=1/1) purified, so as to obtain the title product 3-ethynyl-5-methoxy-N-methylbenzamide 20d (140 mg, light yellow solid), and the yield was 88%.

MS m/z (ESI): 190[M+H]

Step 4

(S)-3-(5-amino-4-carbamoyl-3-((3-methoxy-5-(methylcarbamoyl)phenyl)ethynyl)-1H-pyrazole-1-carboxylic Acid Tert-Butyl Ester (S)-3-(5-amino-3-bromo-4-carbamoyl-1H-pyrazol-1-yl)pyrrolidine-1-carboxylic acid tert-butyl ester 19e (329 mg, 0.88 mmol), triethylamine (2 mL), 1,1'-bisdiphenylphosphinoferrocene palladium dichloride (129 mg, 0.2 mmol), cuprous iodide (34 mg, 0.18 mmol) and N,N-dimethylformamide (8 mL) were mixed, and then deoxygenated, and heated to 90° C. under an argon atmosphere, then a solution of 3-ethynyl-5-methoxy-N-methylbenzamide 20d (1.00 g, 5.3 mmol) in N,N-dimethylformamide (2 mL) was added dropwise, continued stirring for 12 hours, the solvent was removed under reduced pressure, and the residue was purified by silica gel column chromatography (dichloromethane/methanol=20/1), so as to obtain the title product (S)-3-(5-amino-4-carbamoyl-3-((3-methoxy-5-(methylcarbamoyl)phenyl)ethynyl)-1H-pyrazole-1-carboxylic acid tert-butyl ester 20e (400 mg, crude, brown solid).

MS m/z (ESI): 383[M+H−100]

Step 5

(S)-5-amino-3-((3-methoxy-5-(methylcarbamoyl)phenyl)ethynyl)-1-(pyrrolidin-3-yl)-1H-pyrazole-4-carboxamide Hydrochloride (S)-3-(5-amino-4-carbamoyl-3-((3-methoxy-5-(methylcarbamoyl)phenyl)ethynyl)-1H-pyrazole-1-carboxylic acid tert-butyl ester 20e (400 mg, crude) dissolved in dichloromethane (5 mL), then added a solution of hydrogen chloride in ethanol (30%, 3 mL), stirred at room temperature for 1 hour, after the reaction was completed, the solvent was removed under reduced pressure, so as to obtain the title product (S)-5-amino-3-((3-methoxy-5-(methylcarbamoyl)phenyl)ethynyl)-1-(pyrrolidin-3-yl)-1H-pyrazole-4-carboxamide hydrochloride 20f (300 mg, crude, brown solid). The product was used directly in the next reaction without purification.

MS m/z (ESI): 383[M+H]

Step 6

(S)-1-(1-acryloylpyrrolidin-3-yl)-5-amino-3-((3-methoxy-5-(methylcarbamoyl)phenyl)ethynyl)-1H-pyrazole-4-carboxamide Compound (S)-5-amino-3-((3-methoxy-5-(methylcarbamoyl)phenyl)ethynyl)-1-(pyrrolidin-3-yl)-1H-pyrazole-4-carboxamide hydrochloride 20f (150 mg, 0.39 mmol, crude), acryloyl chloride (42 mg, 0.47 mmol), sodium bicarbonate (131 mg, 1.56 mmol), water (4 mL), and tetrahydrofuran (8 mL) were mixed at 0° C., and stirred at this temperature for 0.5 hour, and extracted with ethyl acetate (20 mL×2), the organic phases were combined and dried over anhydrous sodium sulfate, the desiccant was removed by filtering, the solvent was removed under reduced pressure, and the residue was purified by silica gel column chromatography (dichloromethane/methanol=20/1), so as to obtain the title product (S)-1-(1-acryloylpyrrolidin-3-yl)-5-amino-3-((3-methoxy-5-(methylcarbamoyl)phenyl)ethynyl)-1H-pyrazole-4-carboxamide 20 (60 mg, white solid), and the yield was 35% in two steps.

MS m/z (ESI): 437[M+H]

$^1$H NMR (400 MHz, CD$_3$OD) δ 7.59 (s, 1H), 7.45 (s, 1H), 7.28 (s, 1H), 6.73-6.58 (m, 1H), 6.36-6.28 (m, 1H), 5.83-5.75 (m, 1H), 5.04-4.93 (m, 1H), 4.12-3.91 (m, 2H), 3.89 (s, 3H), 3.86-3.66 (m, 2H), 2.93 (s, 3H), 2.51-2.44 (m, 1H), 2.42-2.34 (m, 1H).

Example 21

(S)-1-(1-acryloylpyrrolidin-3-yl)-3-((3,5-dimethoxyphenyl)ethynyl)-5-(methylamino)-1H-pyrazole-4-carboxamide

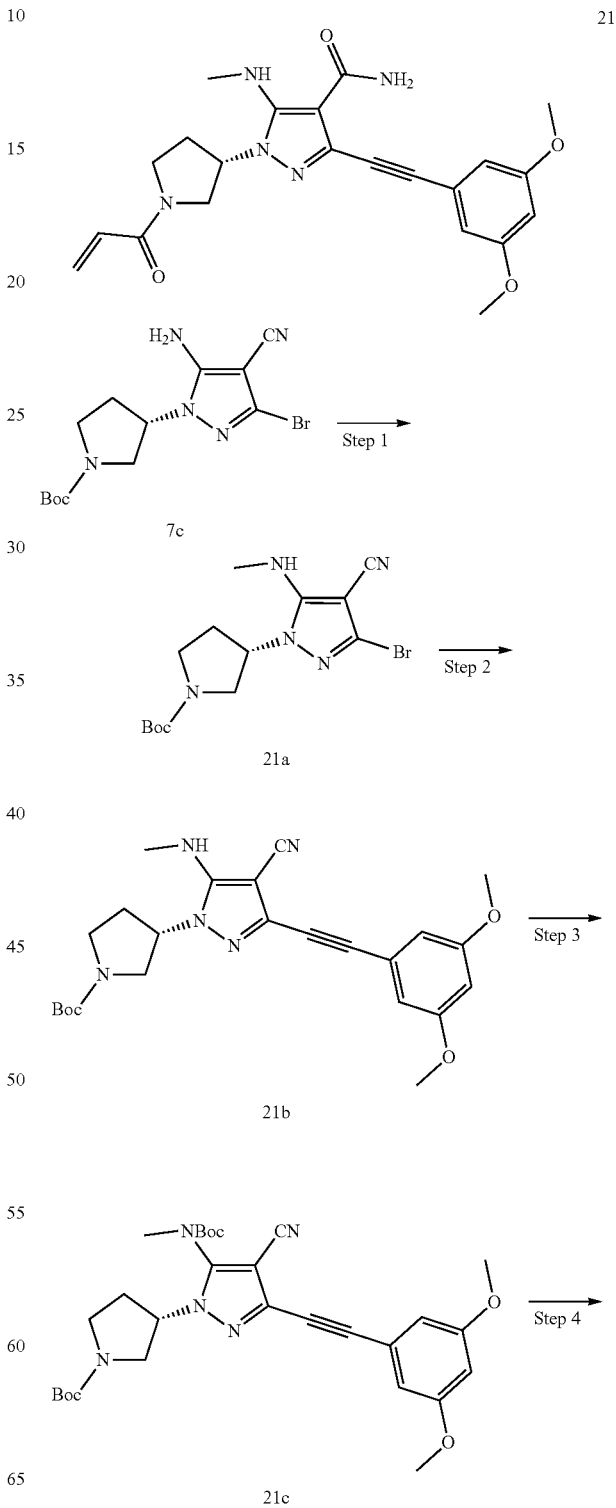

-continued

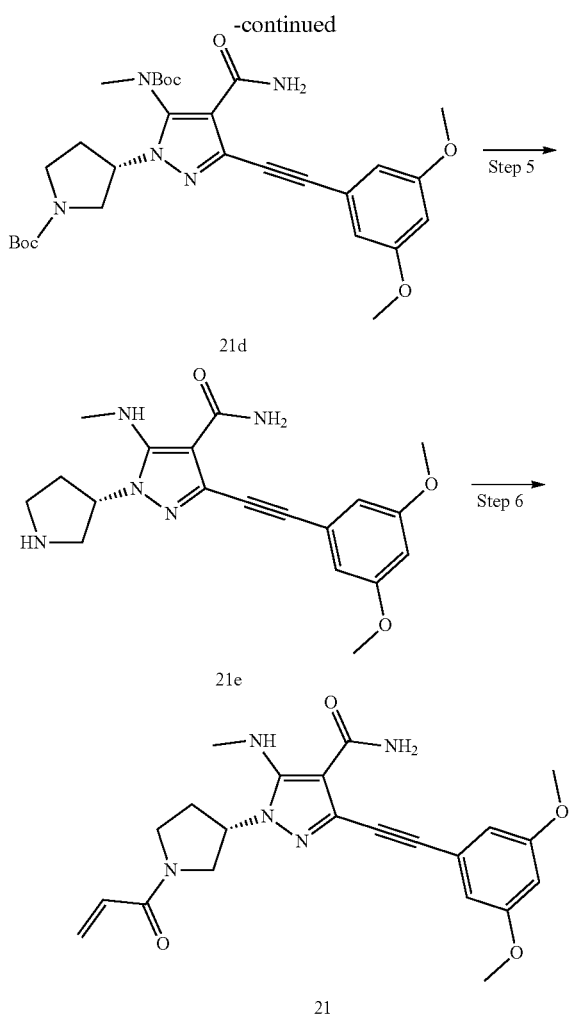

Step 1

(S)-3-(3-bromo-4-cyano-5-(methylamino)-1H-pyrazol-1-yl)pyrrolidine-1-carboxylic Acid Tert-Butyl Ester Compound (S)-3-(5-amino-3-bromo-4-cyano-1H-pyrazol-1-yl)pyrrolidine-1-carboxylic acid tert-butyl ester 7c (178 mg, 0.5 mmol), and benzenesulfonic acid monohydrate (12 mg, 0.07 mmol) were dissolved in triethyl orthoformate (4 mL), and heated to reflux for 2 hours, after the reaction is finished, the solvent was removed under reduced pressure, and the residue was dispersed in water, next extracted with ethyl acetate (30 mL×2), the organic phases were combined and dried over anhydrous sodium sulfate, the desiccant was removed by filtering, the filtrate was removed with solvent under reduced pressure, the residue was dissolved in ethanol (10 mL), and cooled to 0° C., sodium borohydride (89 mg, 2.35 mmol) was added, and then stirred at room temperature for 2 hours, after the reaction is completed, it was quenched with saturated brine, and then extracted with ethyl acetate (30 mL×2), the organic phases were combined, the solvent was removed under reduced pressure, and the residue was purified by silica gel column chromatography (petroleum ether/ethyl acetate=100/1 to 1/1), so as to obtain the title product (S)-3-(3-bromo-4-cyano-5-(methylamino)-1H-pyrazol-1-yl)pyrrolidine-1-carboxylic acid tert-butyl ester 21a (178 mg, white solid), and the yield was 100%.

MS m/z (ESI): 314[M+H−56]

Step 2

(S)-3-(4-cyano-3-((3,5-dimethoxyphenyl)ethynyl)-5-(methylamino)-1H-pyrazol-1-yl)pyrrolidine-1-carboxylic Acid Tert-Butyl Ester (S)-3-(3-bromo-4-cyano-5-(methylamino)-1H-pyrazol-1-yl)pyrrolidine-1-carboxylic acid tert-butyl ester 21a (1.85 g, 5.0 mmol), triethylamine (20 mL), 1,1'-bisdiphenylphosphinoferrocene palladium dichloride (816 mg, 1 mmol), cuprous iodide (190 mg, 1 mmol) and N,N-dimethylmethyl Mix the amide (20 mL) were mixed together, deoxygenated, and then heated to 90° C. under an argon atmosphere, then a solution of 1-ethynyl-3,5-dimethoxybenzene (4.86 g, 30 mmol) in N,N-dimethylformamide (10 mL) was added dropwise, stirring continued for 12 hours, the solvent was removed under reduced pressure, and the residue was purified by silica gel column chromatography (petroleum ether/ethyl acetate=50/1 to 0/1), so as to obtain the title product (S)-3-(4-cyano-3-((3,5-dimethoxyphenyl)ethynyl)-5-(methylamino)-1H-pyrazol-1-yl)pyrrolidine-1-carboxylic acid tert-butyl ester 21b (2.1 g, brown solid), and the yield was 80%.

MS m/z (ESI): 496[M+H−56]

Step 3

(S)-3-(5-((tert-butoxycarbonyl)(methyl)amino)-4-cyano-3-((3,5-dimethoxyphenyl)ethynyl)-1H-pyridyl Zylidene-1-yl)pyrrolidine-1-carboxylic Acid Tert-Butyl Ester (S)-3-(4-cyano-3-((3,5-dimethoxyphenyl)ethynyl)-5-(methylamino)-1H-pyrazol-1-yl)pyrrolidine-1-carboxylic acid tert-butyl ester 21b (225 mg, 0.5 mmol) was dissolved in dichloromethane (10 mL), then triethylamine (150 mg, 1.5 mmol), Boc anhydride (218 mg, 1 mmol) and 4-dimethyl aminopyridine (6 mg, 0.05 mmol) were added sequentially, after stirring at room temperature for 2 hours, saturated brine (10 mL) was added, and then extracted with ethyl acetate (20 mL×2), the organic phases were combined and the solvent was removed under reduced pressure, and the residue was purified by silica gel column chromatography (petroleum ether/ethyl acetate=50/1 to 1/1), so as to obtain the title product (S)-3-(5-((tert-butoxycarbonyl)(methyl)amino)-4-cyano-3-((3,5-dimethoxyphenyl)ethynyl)-1H-pyridyl Zylidene-1-yl)pyrrolidine-1-carboxylic acid tert-butyl ester 21c (200 mg, pale yellow solid), and the yield was 72%.

MS m/z (ESI): 440[M+H−112]

Step 4

(S)-3-(5-((tert-Butoxycarbonyl)(methyl)amino)-4-carbamoyl-3-((3,5-dimethoxyphenyl)ethynyl)-1H-pyrazol-1-yl)pyrrolidine-1-carboxylic Acid Tert-Butyl Ester (S)-3-(5-((tert-butoxycarbonyl)(methyl)amino)-4-cyano-3-((3,5-dimethoxyphenyl)ethynyl)-1H-pyridyl Zylidene-1-yl)pyrrolidine-1-carboxylic acid tert-butyl ester 21c (55 mg, 0.1 mmol), an aqueous solution of sodium hydroxide (0.5 M, 0.1 mL, 0.05 mmol), an aqueous solution of hydrogen peroxide (30%, 0.5 mL) and dimethyl sulfoxide (1 mL) were mixed, and stirred at room temperature for 2 hours, the reactants were diluted with saturated brine (10 mL) and extracted with ethyl acetate (20 mL×2), the organic phases were combined, the solvent was removed under reduced pressure, and the residue was purified by silica gel column chromatography (petroleum ether/ethyl acetate=100/1 to 1/100), so as to obtain the title product (S)-3-(5-((tert-Butoxycarbonyl)(methyl)amino)-4-carbamoyl-3-((3,5-dimethoxyphenyl)ethynyl)-1H-pyrazol-1-yl)pyrrolidine-1-carboxylic acid tert-butyl ester 21d (30 mg, brown solid), and the yield was 50%.

MS m/z (ESI): 414[M+H−156]

Step 5

(S)-3-((3,5-dimethoxyphenyl)ethynyl)-5-(methylamino)-1-(pyrrolidin-3-yl)-1H-pyrazole-4-carboxamide Hydrochloride (S)-3-(5-((tert-Butoxycarbonyl)(methyl)amino)-4-carbamoyl-3-((3,5-dimethoxyphenyl)ethynyl)-1H-pyrazol-1-yl)pyrrolidine-1-carboxylic acid tert-butyl ester 21d (570 mg, 1 mmol) was dissolved in ethyl acetate (10 mL), a solution of hydrogen chloride in ethanol (33%, 5 mL) was then added, and stirred at room temperature for 1 hour, after the reaction is completed, the solvent was removed under reduced pressure, so as to obtain the title product (S)-3-((3, 5-dimethoxyphenyl)ethynyl)-5-(methylamino)-1-(pyrrolidin-3-yl)-1H-pyrazole-4-carboxamide hydrochloride 21e (400 mg, crude, brown solid). This product was used directly in the next step without further purification.

MS m/z (ESI): 370[M+H]

Step 6

(S)-1-(1-acryloylpyrrolidin-3-yl)-3-((3,5-dimethoxyphenyl)ethynyl)-5-(methylamino)-1H-pyrazole-4-carboxamide Compound (S)-3-((3,5-dimethoxyphenyl)ethynyl)-5-(methylamino)-1-(pyrrolidin-3-yl)-1H-pyrazole-4-carboxamide hydrochloride 21e, acryloyl chloride (254 mg, 2.82 mmol), an aqueous solution of potassium carbonate (2.5 M, 4.7 mL, 11.78 mmol) and tetrahydrofuran (10 mL) were mixed and stirred at this temperature for 0.5 hour, next extracted with ethyl acetate (50 mL×2), the organic phases were combined and dried over anhydrous sodium sulfate, the solvent was removed under reduced pressure, and the residue was purified by silica gel column chromatography (dichloromethane/methanol=100/1 to 10/1), so as to obtain the title product (S)-1-(1-acryloylpyrrolidin-3-yl)-3-((3,5-dimethoxyphenyl)ethynyl)-5-(methylamino)-1H-pyrazole-4-carboxamide 21 (720 mg, white solid), and the yield was 76%.

MS m/z (ESI): 424[M+H] $^1$H NMR (400 MHz, CDCl$_3$) δ 6.88 (s, 1H), 6.69 (d, J=2.3 Hz, 2H), 6.51 (t, J=2.2 Hz, 1H), 6.46-6.40 (m, 2H), 5.74-5.72 (m, 1H), 5.52-5.48 (m, 1H), 5.06-5.01 (m, 1H), 4.09-3.94 (m, 3H), 3.80 (s, 6H), 3.72-3.70 (m, 1H), 3.00 (s, 3H), 2.71-2.56 (m, 1H), 2.45-2.35 (m, 1H).

Example 22

(S)-1-(1-acryloylpyrrolidin-3-yl)-3-((2-fluoro-3,5-dimethoxyphenyl)ethynyl)-5-(methylamino)-1H-pyrazole-4-carboxamide

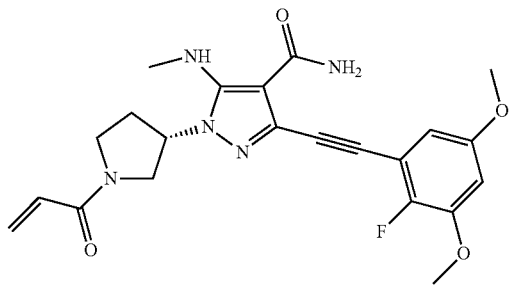

Example 22 was synthesize according to the procedure of Example 21, but in the second step, 1-ethynyl-2-fluoro-3,5-dimethoxybenzene used to substitute 1-ethynyl-3,5-dimethoxybenzene.

MS m/z (ESI): 442[M+H]

$^1$H NMR (400 MHz, CDCl$_3$) 7.08 (s, 1H), 6.68 (d, J=7.2 Hz, 1H), 6.60-6.57 (m, 2H), 6.51-6.40 (m, 2H), 5.74-5.69 (m, 1H), 5.35 (s, 1H), 5.08-4.99 (m, 1H), 4.11-4.08 (m, 1H), 4.05-3.94 (m, 2H), 3.88 (s, 3H), 3.79 (s, 3H), 3.75-3.65 (m, 1H), 3.00 (t, J=5.2 Hz, 3H), 2.72-2.58 (m, 1H), 2.44-2.33 (m, 1H).

Example 23

(S)-1-(1-acryloylpyrrolidin-3-yl)-3-((5-chloro-2-fluorophenyl)ethynyl)-5-(methylamino)-1H-pyrazole-4-carboxamide

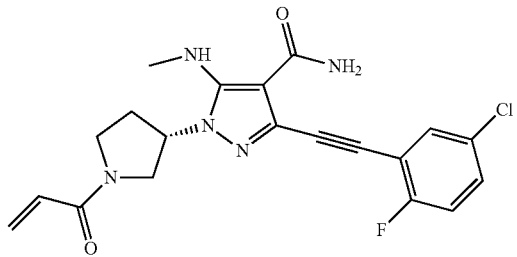

Example 23 was synthesized according to the procedure of Example 21, but in the second step, 4-chloro-2-ethynyl-1-fluorobenzene was used to substitute 1-ethynyl-3,5-dimethoxybenzene.

MS m/z (ESI): 416[M+H]

$^1$H NMR (400 MHz, CDCl$_3$) δ 7.56-7.52 (m, 1H), 7.35-7.33 (m, 1H), 7.08 (t, J=8.8 Hz, 1H), 7.02-6.92 (m, 1H), 6.51-6.39 (m, 2H), 5.74 (d, J=9.3 Hz, 1H), 5.55-5.44 (m, 1H), 5.09-4.98 (m, 1H), 4.14-3.90 (m, 3H), 3.80-3.65 (m, 1H), 3.01 (s, 3H), 2.74-2.55 (m, 1H), 2.49-2.34 (m, 1H).

Example 24

(S)-1-(1-acryloylpyrrolidin-3-yl)-3-((3,5-dimethoxyphenyl)ethynyl)-5-(ethylamino)-1H-pyrazole-4-carboxamide

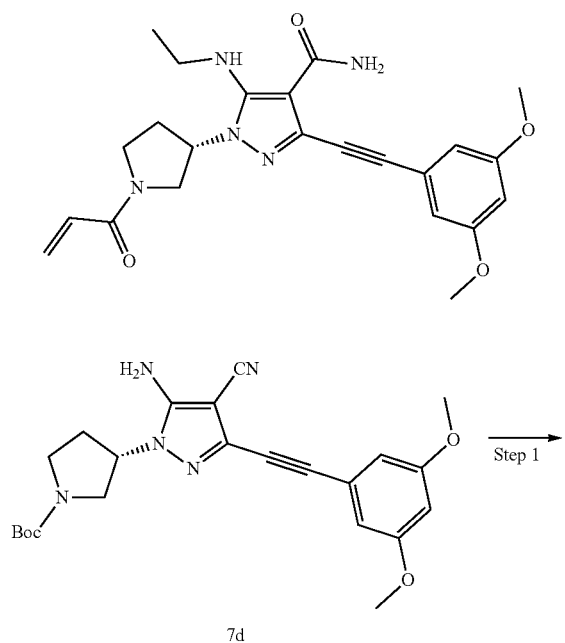

7d

24a

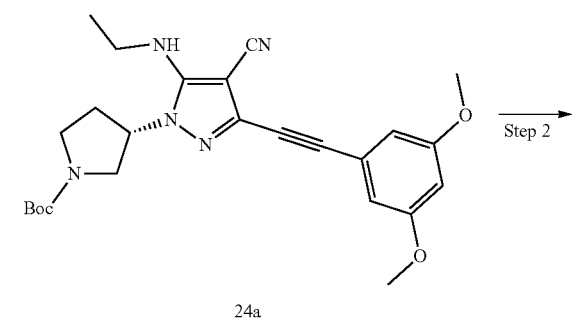

24b

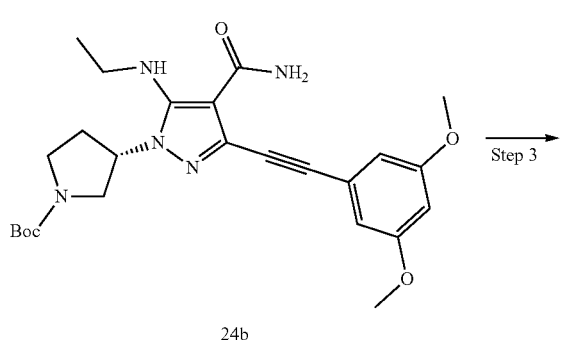

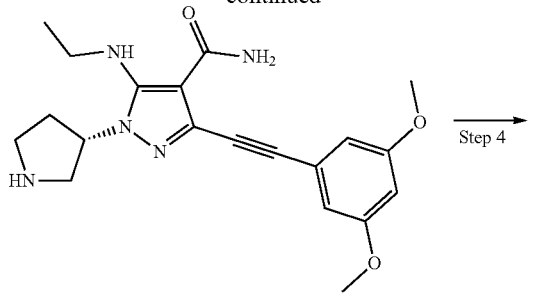

24c

24

Step 1

(S)-3-(5-ethylamino-4-cyano-3-((3,5-dimethoxyphenyl)ethynyl)-1H-pyrazol-1-yl)pyrrolidine-1-carboxylic Acid Tert-Butyl Ester A mixture (S)-3-(5-amino-4-cyano-3-((3,5-dimethoxyphenyl)ethynyl)-1H-pyrazol-1-yl)pyrrolidine-1-carboxylic acid tert-butyl ester 7d (500 mg, 1.14 mmol) and sodium hydride (91 mg, 2.28 mmol, 60%) were added to N,N-diethylacetamide (5 mL), and stirred for 10 minutes, iodoethane (106 mg, 0.68 mmol) was then added, and stirred for 0.5 hours, the reaction solution was poured into the water, and then concentrated under reduced pressure, the residue was purified by reverse-phase high performance liquid preparative chromatography [acetonitrile/water (containing 0.1% formic acid): 50%-90%], so as to obtain the title product (S)-3-(5-ethylamino-4-cyano-3-((3,5-dimethoxyphenyl)ethynyl)-1H-pyrazol-1-yl)pyrrolidine-1-carboxylic acid tert-butyl ester 24a (70 mg, white solid), and the yield was 22%.

MS m/z (ESI): 410[M+1-56]

Step 2

(S)-3-(5-ethylamino-4-carbamoyl-3-((3,5-dimethoxyphenyl)ethynyl)-1H-pyrazol-1-yl)pyrrolidine-1-carboxylic Acid Tert-Butyl Ester (S)-3-(5-ethylamino-4-cyano-3-((3,5-dimethoxyphenyl)ethynyl)-1H-pyrazol-1-yl)pyrrolidine-1-carboxylic acid tert-butyl ester 24a (55 mg, 0.12 mmol) was dissolved in dimethyl sulfoxide (3 mL), next hydrogen peroxide was added (2 mL) and sodium hydroxide (300 mg, 7.5 mmol), after stirring at room temperature for 10 minutes, warm it up to 40° C., after the reaction was completed, it was diluted with water (20 mL) after cooling, extracted with ethyl acetate (30 mL), and washed with water (20 mL×3), the organic phase was concentrated under reduced pressure, the residue was purified by reverse-phase high performance liquid preparative chromatography [acetonitrile/water (containing 0.1% formic acid): 50%-90%], so as to obtain the title product (S)-3-(5-ethylamino-4-carbamoyl-3-((3,5-dimethoxyphenyl)ethynyl)-1H-pyrazol-1-yl)pyrrolidine-1-carboxylic acid tert-butyl ester 24b (15 mg), and the yield was 26%.

MS m/z (ESI): 484 [M+1]

Step 3

(S)-3-((3,5-dimethoxyphenyl)ethynyl)-5-(ethylamino)-1-(pyrrolidin-3-yl)-1H-pyrazole-4-carboxamide (S)-3-(5-ethylamino-4-carbamoyl-3-((3,5-dimethoxyphenyl)ethynyl)-1H-pyrazol-1-yl)pyrrolidine-1-carboxylic acid tert-butyl ester 24b (15 mg, 0.031 mmol) was dissolved in dichloromethane (2 mL), trifluoroacetic acid (0.5 mL) was then added, stirred for half an hour, after the reaction is completed, the reaction system was concentrated under reduced pressure, so as to obtain the title product (S)-3-((3,5-Dimethoxyphenyl)ethynyl)-5-(ethylamino)-1-(pyrrolidin-3-yl)-1H-pyrazole-4-carboxamide 24c (20 mg, crude, brown oil), and the yield was >100%. The product was used in the next reaction without purification.

MS m/z (ESI): 384[M+1]

Step 4

(S)-1-(1-acryloylpyrrolidin-3-yl)-3-((3,5-dimethoxyphenyl)ethynyl)-5-(ethylamino)-1H-pyrazole-4-carboxamide Compound (S)-3-((3,5-Dimethoxyphenyl)ethynyl)-5-(ethylamino)-1-(pyrrolidin-3-yl)-1H-pyrazole-4-carboxamide 24c (20 mg, 0.031 mmol, crude) was dissolved in tetrahydrofuran (5 mL), and then added a saturated sodium bicarbonate solution (2 mL), next added a solution of acryloyl chloride (2.7 mg, 0.03 mmol) in tetrahydrofuran, stirred for 0.5 hours, the reaction solution was concentrated under reduced pressure, the residue was dissolved in ethyl acetate (30 mL), and then washed with water (20 mL×3), the organic phases were then concentrated under reduced pressure, and the residue was purified by reverse-phase high performance liquid preparative chromatography [acetonitrile/water (containing 0.1% formic acid): 20%-70%], so as to obtain the title product (S)-1-(1-acryloylpyrrolidin-3-yl)-3-((3,5-dimethoxyphenyl)ethynyl)-5-(ethylamino)-1H-pyrazole-4-carboxamide 24 (4.7 mg, white solid), and the yield was 24%.

MS m/z (ESI): 438[M+1]

$^1$H NMR (400 MHz, CDCl$_3$) δ 8.87 (brs, 1H), 6.74 (s, 2H), 6.54 (s, 1H), 6.52 (s, 1H), 6.48-6.40 (m, 2H), 5.74-5.69 (m, 1H), 5.06-4.97 (m, 2H), 4.13-3.93 (m, 3H), 3.84 (s, 6H), 3.80-3.67 (m, 1H), 3.42 (brs, 2H), 2.75-2.35 (m, 2H), 1.31-1.25 (m, 3H).

Example 25

(S)-1-(1-acryloylpyrrolidin-3-yl)-3-((3,5-dimethoxyphenyl)ethynyl)-5-(isopropylamino)-1H-pyrazole-4-carboxamide

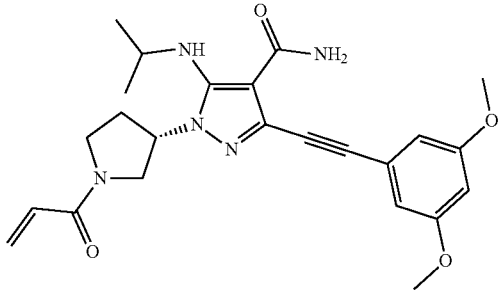

-continued

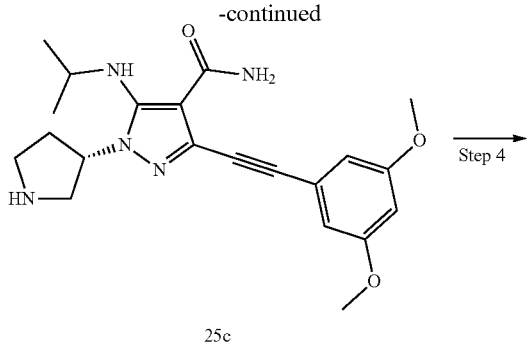

25c

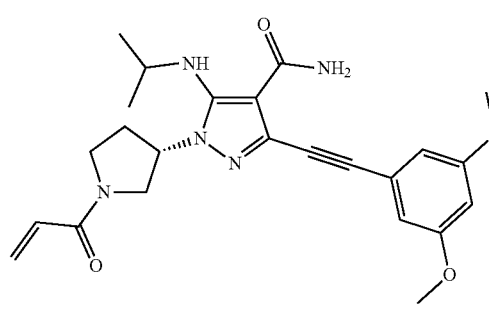

25

Step 1

(S)-3-(4-cyano-3-((3,5-dimethoxyphenyl)ethynyl)-5-(isopropylamino)-1H-pyrazol-1-yl)pyrrolidine-1-carboxylic Acid Tert-Butyl Ester A mixture (S)-3-(5-amino-4-cyano-3-((3,5-dimethoxyphenyl)ethynyl)-1H-pyrazol-1-yl)pyrrolidine-1-carboxylic acid tert-butyl ester 7d (600 mg, 1.37 mmol), cesium carbonate (893 mg, 2.74 mmol) and acetonitrile (25 mL) was stirred for 10 minutes, then quickly added 2-bromopropane (186 mg, 1.51 mmol), heated to 72° C., stirred for 6 hours, and then cooled to room temperature, and concentrated under reduced pressure, the residue was purified by silica gel column chromatography (petroleum ether/ethyl acetate=2/1), so as to obtain the title product (S)-3-(4-cyano-3-((3,5-dimethoxyphenyl)ethynyl)-5-(isopropylamino)-1H-pyrazol-1-yl)pyrrolidine-1-carboxylic acid tert-butyl ester 25a (600 mg, pale yellow solid), and the yield was 91%.

MS m/z (ESI): 424[M+1-56]

Example 25 was synthesized with reference to the operation of the second to fourth steps carried out in Example 24.

MS m/z (ESI): 452[M+1]

$^1$H NMR (400 MHz, CDCl$_3$) δ 6.88 (brs, 1H), 6.70 (s, 2H), 6.54 (s, 1H), 6.51-6.39 (m, 2H), 6.03 (t, J=10.3 Hz, 1H), 5.74-5.69 (m, 1H), 5.49 (brs, 1H), 4.96-4.87 (m, 1H), 4.09-3.86 (m, 3H), 3.80-3.66 (m, 7H), 3.45-3.43 (m, 1H), 2.69-2.32 (m, 2H), 1.27-1.15 (m, 6H).

Example 26

(S)-1-(1-acryloylpyrrolidin-3-yl)-5-((cyclopropylmethyl)amino)-3-((3,5-dimethoxyphenyl)ethynyl)-1H-pyrazole-4-carboxamide Step 1

(S)-1-(1-acryloylpyrrolidin-3-yl)-5-((cyclopropylmethyl)amino)-3-((3,5-dimethoxyphenyl)ethynyl)-1H-pyrazole-4-carboxamide

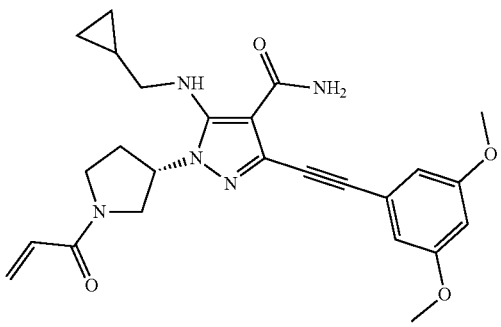

26

Compound (S)-1-(1-acryloylpyrrolidin-3-yl)-5-amino-3-((3,5-dimethoxyphenyl)ethynyl)-1H-pyrazole-4-carboxamide 7 (50 mg, 0.12 mmol) was dissolved in acetonitrile (2 mL), and then added cesium carbonate (80 mg, 0.24 mmol) and (bromomethyl)cyclopropane (19 mg, 0.13 mmol), heated to 70° C., stirred for 4 hours, next the reaction solution was poured into water (30 mL), and extracted with ethyl acetate (30 mL×3), the organic phases were combined and dried over anhydrous sodium sulfate, the residue was prepared by chromatography on a thin layer of silica gel (dichloromethane/methanol=12/1) for purification, so as to obtain the title product (S)-1-(1-acryloylpyrrolidin-3-yl)-5-((cyclopropylmethyl)amino)-3-((3,5-dimethoxyphenyl)

ethynyl)-1H-pyrazole-4-carboxamide 26 (14 mg, white solid), and the yield was 28%.

MS m/z (ESI): 464[M+1]

¹H NMR (400 MHz, CDCl₃) δ 6.89 (brs, 1H), 6.71 (s, 2H), 6.54 (s, 1H), 6.51-6.37 (m, 2H), 5.76-5.71 (m, 1H), 5.40 (brs, 1H), 5.03-4.95 (m, 1H), 4.06-3.89 (m, 3H), 3.82 (s, 6H), 3.78-3.67 (m, 1H), 3.06-3.02 (m, 2H), 2.69-2.52 (m, 1H), 2.46-2.35 (m, 1H), 1.15-0.98 (m, 1H), 0.63-0.60 (m, 2H), 0.29-0.27 (m, 2H).

Example 27

(S)-1-(1-acryloylpyrrolidin-3-yl)-3-((3,5-dimethoxyphenyl)ethynyl)-5-((2,2,2-trifluoroethyl) amino)-1H-pyrazole-4-carboxamide

27

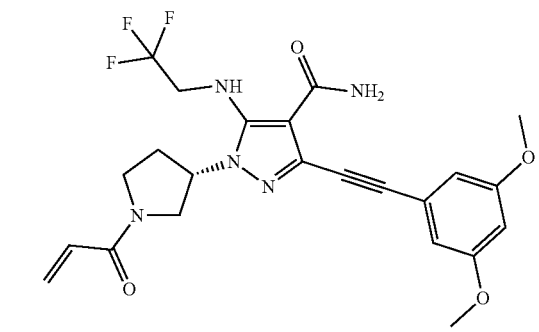

7d

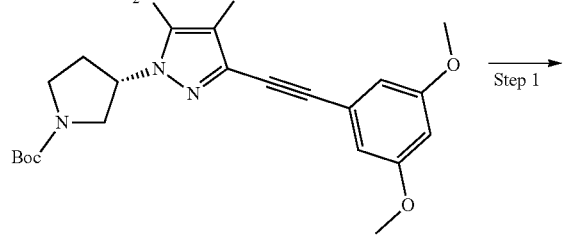

27a

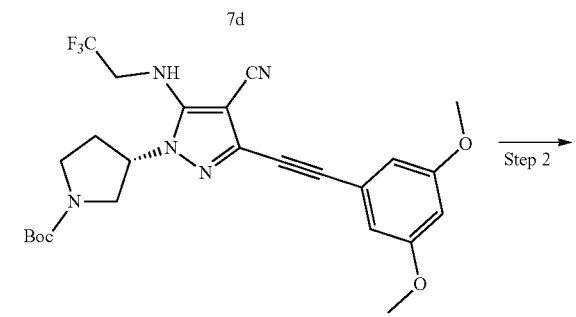

27b

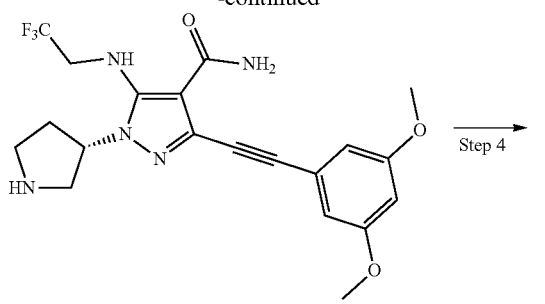

27c

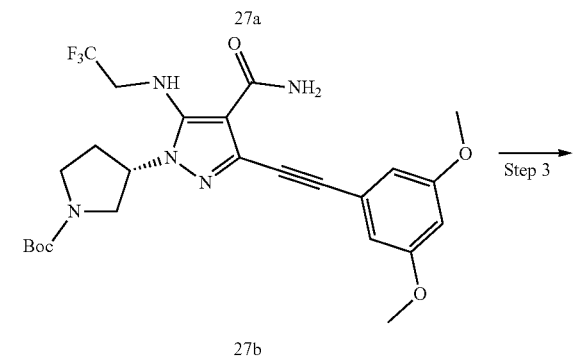

27

Step 1

(S)-3-(4-cyano-3-((3,5-dimethoxyphenyl)ethynyl)-5-((2,2,2-trifluoroethyl)amino)-1H-pyrazol-1-yl)pyrrolidine-1-carboxylic Acid Tert-Butyl Ester (S)-3-(5-amino-4-cyano-3-((3,5-dimethoxyphenyl)ethynyl)-1H-pyrazol-1-yl)pyrrolidine-1-carboxylic acid tert-butyl ester 7d (430 mg, 0.98 mmol), an aqueous solution of trifluoroacetaldehyde (75%) (304 mg, 1.96 mmol) and tetraethyl titanate (448 mg, 1.96 mmol) were added to dichloromethane (15 mL), stirred for 2 hours, after the reaction was completed, sodium borohydride (75 mg, 1.96 mmol) was added to the reaction mixture, and the stirring was continued at room temperature for 1 hour, the reaction mixture was poured into water and extracted with ethyl acetate (20 mL×3), the organic phase was combined and dried over anhydrous sodium sulfate, the desiccant was removed by filtering, and the reaction system was concentrated under reduced pressure, and the residue was quickly purified by a column, so as to obtain the title product (S)-3-(4-cyano-3-((3,5-dimethoxyphenyl)ethynyl)-5-((2,2,2-trifluoroethyl)amino)-1H-pyrazol-1-yl)pyrrolidine-1-carboxylic acid tert-butyl ester 27a (120 mg, yellow oily substance), and the yield was 26%.

MS m/z (ESI): 464[M+1-56]

Example 27 was synthesized by referring to the operation of the second to fourth steps carried out in Example 24.

MS m/z (ESI): 492[M+1]

¹H NMR (400 MHz, CDCl₃) δ 6.92 (brs, 1H), 6.70 (s, 2H), 6.52 (s, 1H), 6.47-6.39 (m, 2H), 6.31-6.25 (m, 1H), 5.75-5.65 (m, 1H), 5.65 (brs, 1H), 5.05-4.98 (m, 1H), 4.10-3.88 (m, 3H), 3.80 (s, 6H), 3.75-3.61 (m, 3H), 2.63-2.34 (m, 2H).

Example 28

(S)-1-(1-acryloylpyrrolidin-3-yl)-3-((3,5-dimethoxy-phenyl)ethynyl)-5-((2-methoxyethyl) amino)-1H-pyrazole-4-carboxamide

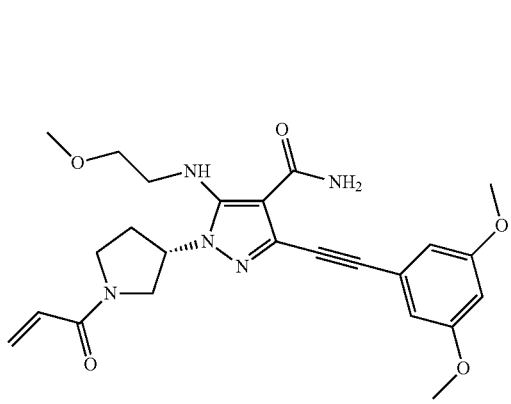

28

Example 28 was synthesized by following the procedure of Example 25, but in the first step, 1-bromo-2-methoxy-ethane was used to substitute 2-bromopropane.

MS m/z (ESI): 468[M+1]

$^1$H NMR (400 MHz, DMSO-d$_6$) δ 7.32 (brs, 1H), 6.74 (d, J=2.2 Hz, 2H), 6.64 (dd, J=16.8, 10.4 Hz, 1H), 6.60 (t, J=2.2 Hz, 1H), 6.50 (t, J=6.0 Hz, 1H), 6.16 (dd, J=16.8, 5.0 Hz, 1H), 5.68 (t, J=10.8 Hz, 1H), 5.15-5.05 (m, 1H), 4.05-4.01 (m, 0.5H), 3.86-3.81 (m, 1.5H), 3.77 (s, 6H), 3.70-3.61 (m, 1H), 3.59-3.50 (m, 1H), 3.46 (t, J=5.1 Hz, 2H), 3.39-3.34 (m, 2H), 3.26 (s, 3H), 2.42-2.23 (m, 2H).

Example 29

(S)-1-(1-acryloylpyrrolidin-3-yl)-3-((3,5-dimethoxy-phenyl)ethynyl)-5-((2-hydroxyethyl)amino)-1H-pyrazole-4-carboxamide

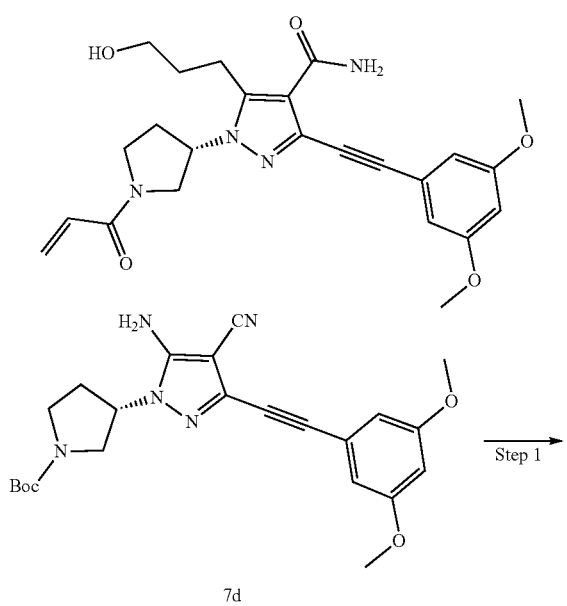

29

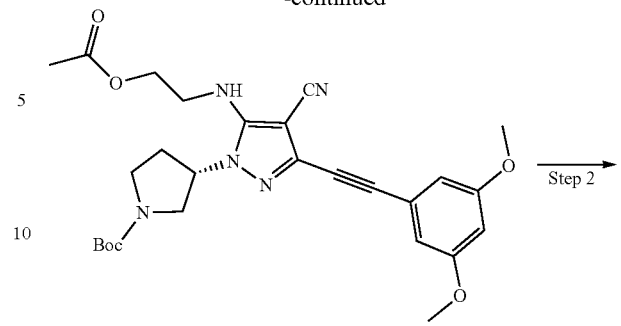

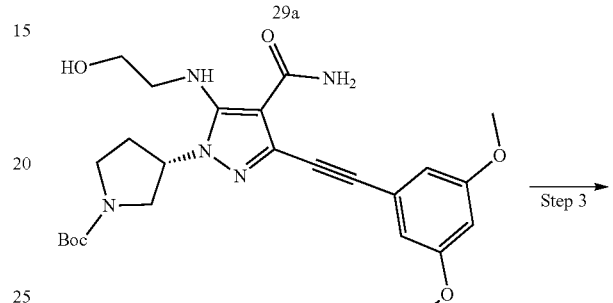
29a

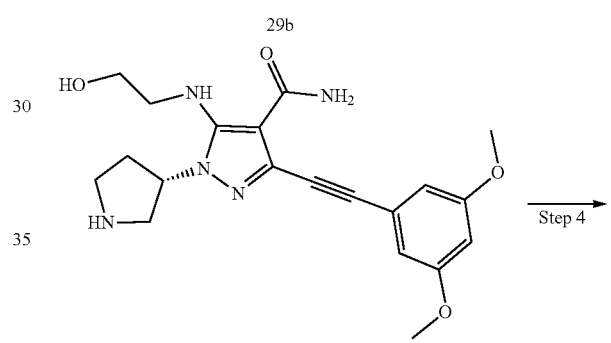
29b

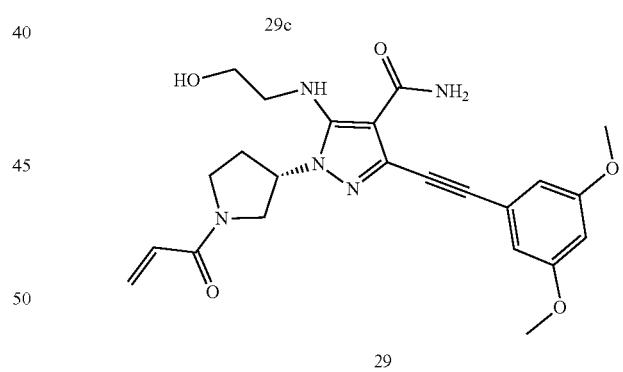
29c

29

Step 1

(S)-3-(5-((2-acetoxyethyl)amino)-4-cyano-3-((3,5-dimethoxyphenyl)ethynyl)-1H-pyrazole-1-yl)pyrrolidine-1-carboxylic Acid Tert-Butyl Ester A mixture of (S)-3-(5-amino-4-cyano-3-((3,5-dimethoxyphenyl)ethynyl)-1H-pyrazol-1-yl)pyrrolidine-1-carboxylic acid tert-butyl ester 7d (300 mg, 0.685 mmol), 2-bromoethyl acetate (126 mg, 0.753 mmol), cesium carbonate (447 mg, 1.37 mmol) and acetonitrile (4 mL) was heated to 90° C., stirred for 2 hours, the reaction solution was cooled to room temperature, and poured into water (50 mL), and then extracted with ethyl acetate (30 mL×3), the organic phases were combined and dried over anhydrous sodium sulfate, the desiccant was removed by filtering, and the reaction system was concentrated under reduced pressure, the residue was purified by silica gel column chromatography (dichloromethane/methanol=15/1), so as to obtain the title product (S)-3-(5-((2-acetoxyethyl)amino)-4-cyano-3-((3,5-dimethoxyphenyl)ethynyl)-1H-pyrazole-1-yl)pyrrolidine-1-carboxylic acid tert-butyl ester 29a (148 mg, yellow solid), and the yield was 41%.

MS m/z (ESI): 468[M+1-56]

Step 2

(S)-3-(4-carbamoyl-3-((3,5-dimethoxyphenyl)ethynyl)-5-((2-hydroxyethyl)amino)-1H-pyrazole-1-yl)pyrrolidine-1-carboxylic Acid Tert-Butyl Ester The mixture of (S)-3-(5-((2-acetoxyethyl)amino)-4-cyano-3-((3,5-dimethoxyphenyl)ethynyl)-1H-pyrazole-1-yl)pyrrolidine-1-carboxylic acid tert-butyl ester 29a (68 mg, 0.146 mmol), ethanol (5 mL) and dimethyl sulfoxide (1 mL) was added with a saturated sodium hydroxide solution (3 mL) and hydrogen peroxide (4 mL), stirred 30° C. for 1 hour, after the reaction is completed, the reaction solution was poured into a saturated sodium sulfite solution (30 mL), and extracted with ethyl acetate (30 mL×3), the organic phases were combined and dried over anhydrous sodium sulfate, the desiccant was removed by filtering, and the reaction system was concentrated under reduced pressure, so as to obtain the title product (S)-3-(4-carbamoyl-3-((3,5-dimethoxyphenyl)ethynyl)-5-((2-hydroxyethyl)amino)-1H-pyrazole-1-yl)pyrrolidine-1-carboxylic acid tert-butyl ester 29b (110 mg, crude, yellow oily substance), and the yield was >100%. The product was used in the next reaction without purification.

MS m/z (ESI): 444[M+1-56]

Step 3

(S)-3-((3,5-dimethoxyphenyl)ethynyl)-5-((2-hydroxyethyl)amino)-1-(pyrrolidin-3-yl)-1H-pyrazole-4-carboxamide Compound (S)-3-(4-carbamoyl-3-((3,5-dimethoxyphenyl)ethynyl)-5-((2-hydroxyethyl)amino)-1H-pyrazole-1-yl)pyrrolidine-1-carboxylic acid tert-butyl ester 29b (110 mg, 0.146 mmol, crude) was dissolved in a solution of hydrochloric acid in methanol (5 mL), heat to 40° C. and stirred for 1 hour, after the reaction was completed, and the reaction system was concentrated under reduced pressure, so as to obtain the title product (S)-3-((3,5-dimethoxyphenyl)ethynyl)-5-((2-hydroxyethyl)amino)-1-(pyrrolidin-3-yl)-1H-pyrazole-4-carboxamide 29c (160 mg, crude, white solid), and the yield was >100%. The product was used in the next reaction without purification.

MS m/z (ESI): 400[M+1]

Step 4

(S)-1-(1-acryloylpyrrolidin-3-yl)-3-((3,5-dimethoxyphenyl)ethynyl)-5-((2-hydroxyethyl)amino)-1H-pyrazole-4-carboxamide The compound (S)-3-((3,5-dimethoxyphenyl)ethynyl)-5-((2-hydroxyethyl)amino)-1-(pyrrolidin-3-yl)-1H-pyrazole-4-carboxamide 29c (160 mg, 0.146 mmol, crude) was dissolved in tetrahydrofuran (5 mL), and then added a saturated sodium bicarbonate solution (10 mL), and then added acryloyl chloride (12 mg, 0.13 mmol), stirred at room temperature for 10 minutes, After the reaction is completed, the reaction solution was poured into water (50 mL), and extracted with ethyl acetate (30 mL×3), the organic phases were combined and dried over anhydrous sodium sulfate, the desiccant was removed by filtering, and the reaction system was concentrated under reduced pressure, the residue was purified by reverse-phase high-performance preparative chromatography [acetonitrile/water (with 0.2% formic acid): 20% to 60%], so as to obtain the title product (S)-1-(1-acryloylpyrrolidin-3-yl)-3-((3,5-dimethoxyphenyl)ethynyl)-5-((2-hydroxyethyl)amino)-1H-pyrazole-4-carboxamide 29 (6 mg, white solid), and the yield was 9%.

MS m/z (ESI): 454[M+1]

$^1$H NMR (400 MHz, DMSO-$d_6$) δ 7.36 (brs, 1H), 6.76 (brs, 1H), 6.74 (s, 2H), 6.70-6.60 (m, 2H), 6.55-6.52 (m, 1H), 6.17 (d, J=16.9 Hz, 1H), 5.69 (t, J=10.9 Hz, 1H), 5.16-5.10 (m, 1H), 4.87 (s, 1H), 4.06-4.0 (m, 0.5H), 3.83-3.81 (m, 1.5H), 3.77 (s, 6H), 3.68-3.63 (m, 2H), 3.55-3.53 (m, 2H), 3.28-3.26 (m, 2H), 2.38-2.27 (m, 2H).

Example 30

(S)-1-(1-acryloylpyrrolidin-3-yl)-3-((3,5-dimethoxyphenyl)ethynyl)-5-((3-morpholinopropyl) amino)-1H-pyrazole-4-carboxamide

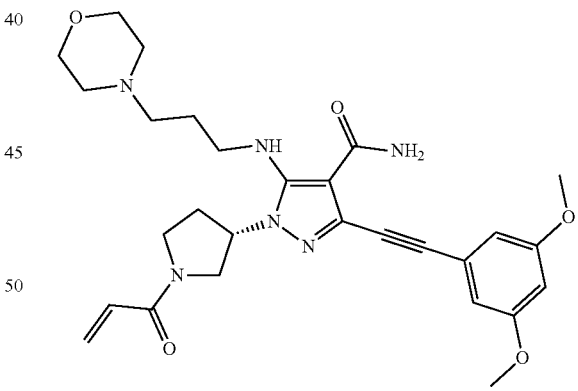

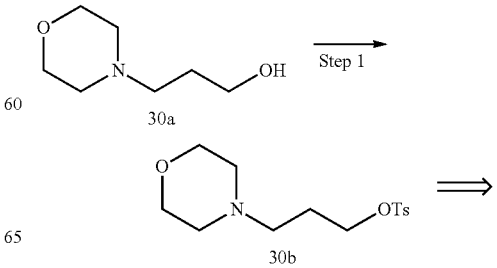

87
-continued

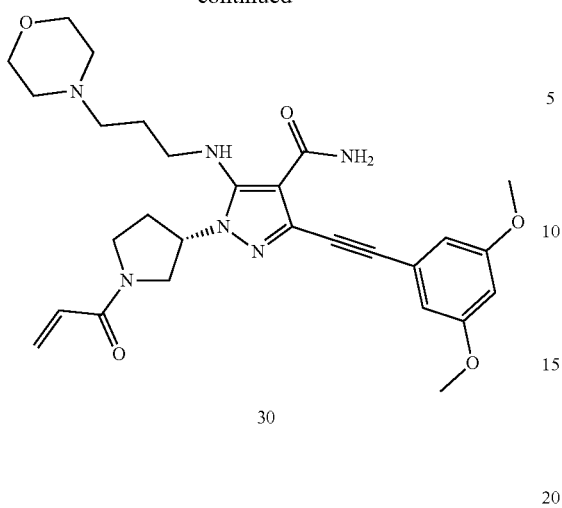

30

Step 1

3-morpholinopropyl 4-methylbenzenesulfonate

Compound 3-morpholinopropan-1-ol 30a (500 mg, 3.45 mmol) was dissolved in dichloromethane (100 ml), and then added 4-dimethylaminopyridine (42 mg, 0.34 mmol), triethylamine (1.04 g, 10.3 mmol) and p-toluenesulfonyl chloride (988 mg, 5.17 mmol), stirred at room temperature overnight, after the reaction is completed, the reaction solution was poured into water (50 mL), and then extracted with dichloromethane (50 mL×3), the organic phases were combined and dried over anhydrous sodium sulfate, the desiccant was removed by filtering, and the reaction system was concentrated under reduced pressure, the residue was purified by silica gel column chromatography (petroleum ether/ethyl acetate=2/1), so as to obtain the title product 3-morpholinopropyl 4-methylbenzenesulfonate 30b (660 mg, yellow oily substance), and the yield was 64%.

MS m/z (ESI): 300[M+1]

Example 30 was synthesized with reference to the procedure of Example 25, but in the first step, 3-morpholinopropyl 4-methylbenzenesulfonate was used to substitute 2-bromopropane.

MS m/z (ESI): 537[M+1]

$^1$H NMR (400 MHz, CDCl$_3$) δ 8.23 (brs, 1H), 7.12 (brs, 1H), 6.94 (brs, 1H), 6.69 (s, 2H), 6.52 (s, 1H), 6.49-6.40 (m, 2H), 5.92 (brs, 1H), 5.74-5.70 (m, 1H), 5.03-4.96 (m, 1H), 4.09-3.90 (m, 3H), 3.80-3.68 (m, 11H), 3.28 (brs, 2H), 2.89 (brs, 6H), 2.69-2.33 (m, 2H), 1.93 (brs, 2H).

88

Example 31

(S)-1-(1-acryloylpyrrolidin-3-yl)-3-((3,5-dimethoxyphenyl)ethynyl)-5-((2-morpholinoethyl)amino)-1H-pyrazole-4-carboxamide

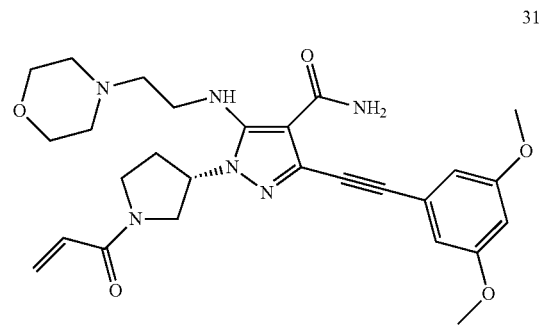 [SMILES: C=CC(=O)N1CC[C@H](n2nc(C#Cc3cc(OC)cc(OC)c3)c(C(N)=O)c2NCCN2CCOCC2)C1]

31

Example 31 was synthesized by reference to the procedure of Example 25, but in the first step, 2-bromopropane was substituted by 4-(2-chloroethyl)morpholine.

MS m/z (ESI): 523[M+1]

$^1$H NMR (400 MHz, CDCl$_3$) δ 8.14 (s, 1H), 6.95 (brs, 1H), 6.69 (s, 2H), 6.63 (brs, 1H), 6.52 (s, 1H), 6.49-6.39 (m, 2H), 6.14 (brs, 1H), 5.75-5.70 (m, 1H), 5.06-4.98 (m, 1H), 4.11-3.85 (m, 3H), 3.80-3.72 (m, 11H), 3.37-3.33 (m, 2H), 2.80-2.73 (m, 2H), 2.65 (brs, 4H), 2.45-2.32 (m, 2H).

Example 32

(S)-1-(1-acryloylpyrrolidin-3-yl)-3-((3,5-dimethoxyphenyl)ethynyl)-5-((2-(pyrrolidin-1-yl)ethyl)amino)-1H-pyrazole-4-carboxamide

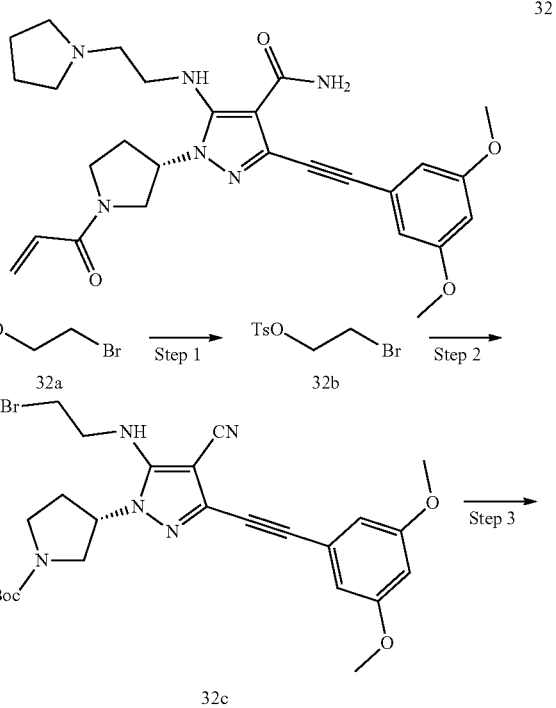

32

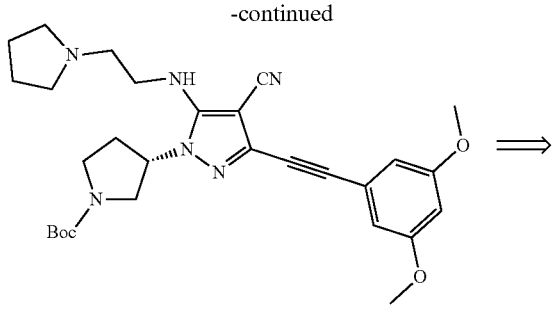

32d

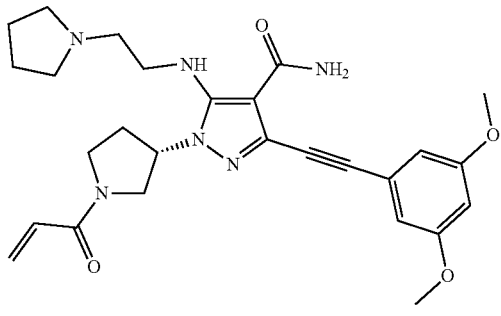

32

Step 1

2-bromoethyl 4-methylbenzenesulfonate

Compound 2-bromoethanol 32a (500 mg, 4.0 mmol), 4-dimethylaminopyridine (246 mg, 2.02 mmol) and triethylamine (1.22 g, 12.1 mmol) were dissolved in dichloromethane (50 mL), cooled down to 0° C., next added p-toluenesulfonyl chloride (1.15 g, 6.05 mmol) in portions, after the addition was finished, stirred at room temperature for overnight, after the reaction is completed, the reaction was poured into water (50 mL), and extracted with dichloromethane (50 mL×3), the organic phases were combined and dried over anhydrous sodium sulfate, the desiccant was removed by filtering, and the reaction system was concentrated under reduced pressure, the residue was purified by silica gel column chromatography (petroleum ether/ethyl acetate=10/1), so as to obtain the title product 2-bromoethyl 4-methylbenzenesulfonate 32b (600 mg, yellow oily substance), and the yield was 53%.

MS m/z (ESI): 277[M+1]

Step 2

(S)-3-(5-((2-bromoethyl)amino)-4-cyano-3-((3,5-dimethoxyphenyl)ethynyl)-1H-pyrazole-1-carboxylic Acid Tert-Butyl Ester A mixture (S)-3-(5-amino-4-cyano-3-((3,5-dimethoxyphenyl)ethynyl)-1H-pyrazol-1-yl)pyrrolidine-1-carboxylic acid tert-butyl ester 7d (400 mg, 0.92 mmol), 2-bromoethyl 4-methylbenzenesulfonate (380 mg, 1.37 mmol), cesium carbonate (600 mg, 1.84 mmol) and acetonitrile (10 mL) was heated to 70° C., stirred for 2 hours, the reaction solution was poured into water (50 mL), and extracted with ethyl acetate (50 mL×3), the organic phases were combined and dried over anhydrous sodium sulfate, the desiccant was removed by filtering, and the reaction system was concentrated under reduced pressure, the residue was purified by a quick column for purification, so as to obtain the title product (S)-3-(5-((2-bromoethyl)amino)-4-cyano-3-((3,5-dimethoxyphenyl)ethynyl)-1H-pyrazole-1-carboxylic acid tert-butyl ester 32c (240 mg, brown oily substance), and the yield was 48%.

MS m/z (ESI): 408[M+1-56-80]

Step 3

(S)-3-(4-cyano-3-((3,5-dimethoxyphenyl)ethynyl)-5-((2-(pyrrolidin-1-yl)ethyl)amino)-1H-pyrazol-1-yl) pyrrolidine-1-carboxylic Acid Tert-Butyl Ester A mixture of (S)-3-(5-((2-bromoethyl)amino)-4-cyano-3-((3,5-dimethoxyphenyl)ethynyl)-1H-pyrazole-1-carboxylic acid tert-butyl ester 32c (240 mg, 0.44 mmol), pyrrolidine (47 mg, 0.66 mmol), cesium carbonate (288 mg, 0.88 mmol) and acetonitrile (5 mL) was heated to 70° C., stirred for 1.5 hours, and reaction solution was poured into water (30 mL), and then extracted with ethyl acetate (30 mL×3), the organic phases were combined and dried over anhydrous sodium sulfate, the desiccant was removed by filtering, and the reaction system was concentrated under reduced pressure, the residue was purified by silica gel column chromatography (dichloromethane/methanol=10/1), so as to obtain the title product (S)-3-(4-cyano-3-((3,5-dimethoxyphenyl)ethynyl)-5-((2-(pyrrolidin-1-yl)ethyl)amino)-1H-pyrazol-1-yl) pyrrolidine-1-carboxylic acid tert-butyl ester 32d (200 mg, yellow oily substance), and the yield was 85%.

MS m/z (ESI): 479[M+1-56]

Example 32 was synthesized with reference to the operation steps of the second to fourth steps carried out in Example 24.

MS m/z (ESI): 507[M+1]

$^1$H NMR (400 MHz, CDCl$_3$) δ 8.38 (s, 1H), 6.99 (brs, 1H), 6.69 (s, 2H), 6.51 (s, 1H), 6.47-6.36 (m, 2H), 5.72-5.67 m, 2H), 5.16-5.08 (m, 1H), 4.12-3.86 (m, 3H), 3.80-3.62 (m, 9H), 3.33-3.29 (m, 6H), 2.62-2.34 (m, 2H), 2.07 (brs, 4H).

Example 33

(S)-1-(1-acryloylpyrrolidin-3-yl)-3-((3,5-dimethoxyphenyl)ethynyl)-5-((tetrahydro-2H-pyran-4-yl)amino)-1H-pyrazole-4-carboxamide

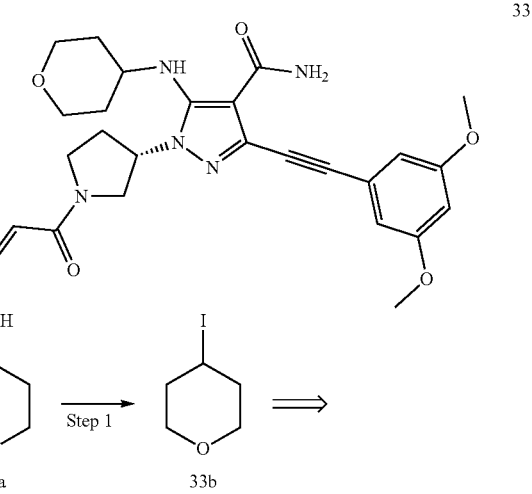

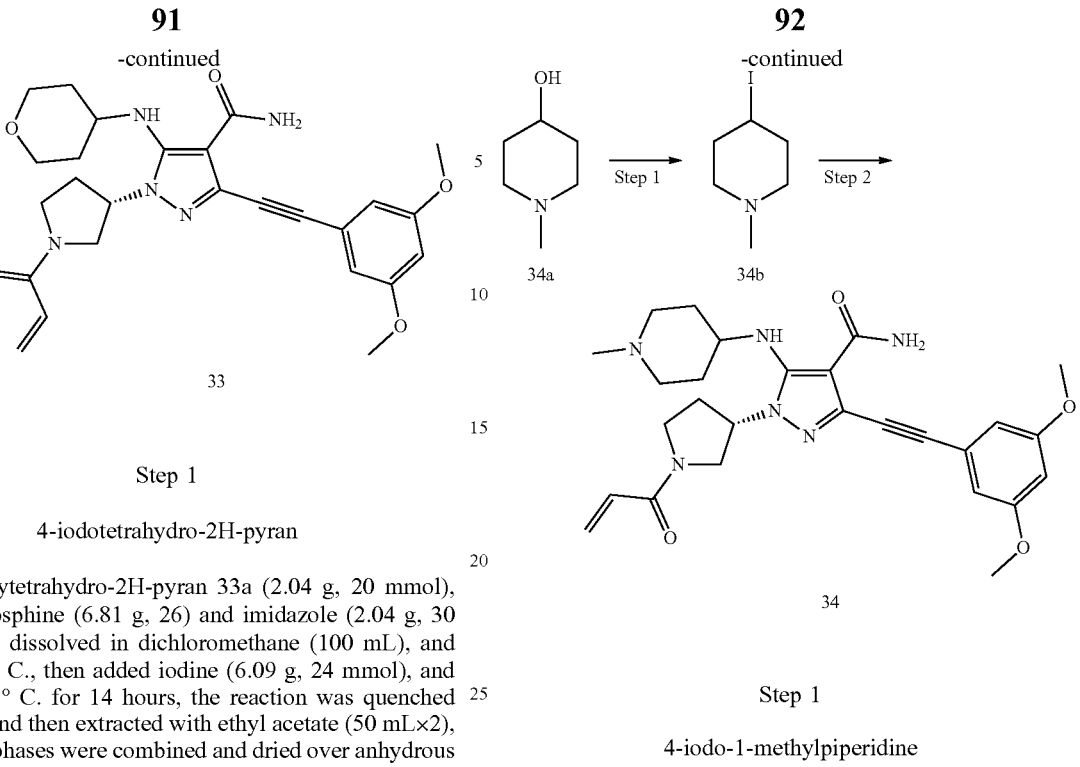

33

Step 1

4-iodotetrahydro-2H-pyran

4-Hydroxytetrahydro-2H-pyran 33a (2.04 g, 20 mmol), triphenylphosphine (6.81 g, 26) and imidazole (2.04 g, 30 mmol) were dissolved in dichloromethane (100 mL), and cooled to 0° C., then added iodine (6.09 g, 24 mmol), and stirred at 45° C. for 14 hours, the reaction was quenched with water and then extracted with ethyl acetate (50 mL×2), the organic phases were combined and dried over anhydrous sodium sulfate, the desiccant was removed by filtering, and the reaction system was concentrated under reduced pressure, the residue was purified by silica gel column chromatography (petroleum ether/ethyl acetate=1/1), so as to obtain the title product 4-iodotetrahydro-2H-pyran 33b (2.12 g, white solid), and the yield was 50%.

$^1$H NMR (400 MHz, DMSO-d$_6$) δ 4.62 (dt, J=13.9, 4.5 Hz, 1H), 3.68-3.64 (m, 2H), 3.47-3.42 (m, 2H), 2.13-1.97 (m, 4H).

Example 33 was synthesized by following the procedure of Example 24, but in the first step, 4-iodotetrahydro-2H-pyran was used to substitute ethyl iodide.

MS m/z (ESI): 494[M+H]

$^1$H NMR (400 MHz, CD$_3$OD) δ 6.74 (t, J=2.2 Hz, 2H), 6.71-6.62 (m, 1H), 6.60-6.58 (m, 1H), 6.36-6.30 (m, 1H), 5.82-5.77 (m, 1H), 5.18-5.12 (m, 1H), 4.04-3.94 (m, 6H), 3.81 (s, 6H), 3.52-3.46 (m, 3H), 2.55-2.39 (m, 2H), 1.94-1.92 (m, 2H), 1.60-1.55 (m, 2H).

Example 34

(S)-1-(1-acryloylpyrrolidin-3-yl)-3-((3,5-dimethoxyphenyl)ethynyl)-5-((1-methylpiperidin-4-yl)amino)-1H-pyrazole-4-carboxamide

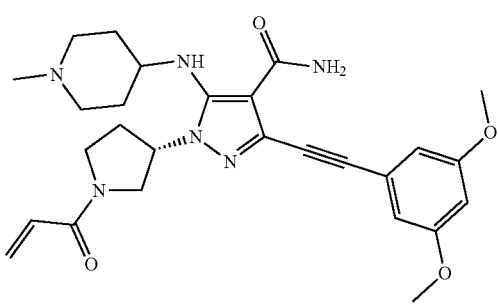

34

Step 1

4-iodo-1-methylpiperidine

4-Hydroxy-1-methylpiperidine 34a (2.3 g, 20 mmol), triphenylphosphine (6.81 g, 26 mmol), imidazole (2.04 g, 30 mmol) and dichloromethane (100 mL) were mixed and cooled down to 0° C., and then added iodine (6.09 g, 24 mmol), and stirring continued for 18 hours, after the reaction was over, it was quenched with water, and then extracted with dichloromethane (50 mL×2), the organic phases were combined and dried over anhydrous sodium sulfate, the desiccant was removed by filtering, and the reaction system was concentrated under reduced pressure, the residue was purified by silica gel column chromatography (dichloromethane/methanol=10/1), so as to obtain the title product 4-iodo-1-methylpiperidine 34b (2.25 g, white solid), and the yield was 50%.

MS m/z (ESI): 226[M+H]

Step 2

(S)-1-(1-acryloylpyrrolidin-3-yl)-3-((3,5-dimethoxyphenyl)ethynyl)-5-((1-methylpiperidin-4-yl) amino)-1H-pyrazole-4-carboxamide Compound (S)-1-(1-acryloylpyrrolidin-3-yl)-5-amino-3-((3,5-dimethoxyphenyl)ethynyl)-1H-pyrazole-4-carboxamide 7 (210 mg, 0.5 mmol), 4-iodo-1-methylpiperidine 34b (450 mg, 2 mmol), potassium carbonate (207 mg, 1.5 mmol) and acetonitrile (10 mL) were mixed and heated and stirred at 90° C. for 13 hours, the solvent was removed under reduced pressure from the reaction mixture, and then the reaction mixture was dissolved in water, and then extracted with ethyl acetate (50 mL×2), the organic phase is combined and the solvent was removed under reduced pressure, the residue was purified by reverse preparative liquid chromatography, so as to obtain the title product (S)-1-(1-acryloylpyrrolidin-3-yl)-3-((3,5-dimethoxyphenyl)ethynyl)-5-((1-methylpiperidin-4-yl) amino)-1H-pyrazole-4-carboxamide 34 (8.1 mg, white solid), and the yield was 3.2%.

MS m/z (ESI): 507[M+H]

¹H NMR (400 MHz, CD₃OD) δ 6.77 (s, 2H), 6.68-6.65 (m, 1H), 6.59 (s, 1H), 6.34-6.30 (m, 1H), 5.81-5.78 (m, 1H), 5.69-5.67 (m, 1H), 5.03-5.00 (m, 1H), 4.98-5.95 (m, 1H), 4.92-4.90 (m, 1H), 4.36 (s, 2H), 4.12-4.07 (m, 1H), 4.00-3.98 (m, 1H), 3.93-3.90 (m, 1H), 3.86-3.84 (m, 1H), 3.81 (s, 6H), 3.72-3.68 (m, 1H), 2.53-2.47 (m, 3H), 2.40-2.38 (m, 1H), 2.32 (s, 3H), 2.27-2.21 (m, 1H).

Biological Experiments

FGFR Activity Inhibition Test

The effect of the compounds of the present invention on the in vitro activity of FGFR was assessed by measuring the phosphorylation level of the substrate in a kinase reaction using the HTRF kinase assay kit (Table 1).

FGFR1 Activity Inhibition Test

The experimental method is outlined below:

The reaction buffer contains the following components: 5-fold diluted enzymatic buffer/kinase 5× (Cisbio, Cat. No. 62EZBFDD) (its main component is 50 mM HEPES, pH 7.0), 5 mM $MgCl_2$ and 1 mM DTT; a human recombinant FGFR1 catalytic domain protein (amino acid 308-731), which was purified by the company, a 0.6 ng/μL kinase solution diluted by the reaction buffer; a substrate reaction solution containing 400 nM biotinylated tyrosine kinase substrate diluted by the reaction buffer (Cisbio, Cat. No. 62TKOPEC) and 40 μM ATP; a test solution containing 0.125 ng/μL $Eu^{3+}$ labeled cage antibody (Cisbio, Cat. No. 61T66KLB) diluted by a test buffer (Cisbio, Cat. No. 62SDBRDF), and 25 nM streptavidin-labeled XL665 (Cisbio, Cat. No. 610SAXLB).

The compounds were diluted to 1 mM in DMSO, then serially diluted 4-fold with DMSO to a minimum concentration of 0.061 μM, and each concentration was further diluted 40-fold with the reaction buffer. If the $IC_{50}$ value of a compound is very low, the initial concentration of the compound can be lowered.

Added 4 μL of compound solution and 2 μL of FGFR1 kinase solution to a 384-well assay plate (Thermo, Cat. No. 264706), mixed well and incubated for 15 minutes at room temperature; then added 4 μL of the substrate reaction solution, and incubated the reaction mixture for 60 minutes at room temperature; and then the reaction was terminated by adding an equal volume of 10 μL of the test solution, and the mixture was uniformly mixed and allowed to stand at room temperature. After 60 minutes, the phosphorylated product was simultaneously recognized by the $Eu^{3+}$ labeled cage antibody (donor) and the streptavidin-labeled XL665 antibody (receptor), after laser excitation, energy resonance transfer occurs between the donor and acceptor which are close to each other, and the energy was transferred from the donor (620 nm) to the acceptor (665 nm), which could be detected by a microplate reader EnVision (Perkin Elmer). The ratio of 665/620 is positively correlated with the degree of phosphorylation of the substrate, thus the activity of FGFR1 kinase was detected.

In this experiment, the group without the enzyme was a 100% inhibition group, the group with the enzyme yet without the compound was a 0% inhibition group. The percentage of inhibition on FGFR1 activity by the compound thus was calculated using the following formula:

Percentage of inhibition=100−100*($ratio_{compound}$−$ratio_{100\% \ inhibition}$)/($ratio_{100\% \ inhibition}$−$ratio_{100\% \ inhibition}$)

The $IC_{50}$ value of the compound was calculated from the 10 concentration points using the XLfit software in Excel by the following formula:

$$Y = Bottom + (Top - Bottom)/(1 + 10\string^((\log IC_{50} - X)*slope\ factor))$$

Where Y is the percentage of inhibition, Bottom is the bottom platform value of the S-curve, Top is the top platform value of the S-curve, X is the logarithm of the concentration of the compound to be tested, and slope factor is the slope coefficient of the curve.

FGFR2 Activity Inhibition Test

The experimental method is outlined below:

The reaction buffer contains the following components: 5-fold diluted enzymatic buffer/kinase 5× (Cisbio, Cat. No. 62EZBFDD) (its main component is 50 mM HEPES, pH 7.0), 5 mM $MgCl_2$ and 1 mM DTT; a human recombinant FGFR2 catalytic domain protein (amino acid 400-821), which was purchased from Yiqiao Shenzhou Biotech Co., Ltd., a 0.45 ng/μL kinase solution diluted by the reaction buffer; a substrate reaction solution containing 800 nM biotinylated tyrosine kinase substrate diluted by the reaction buffer (Cisbio, Cat. No. 62TKOPEC) and 50 μM ATP; a test solution containing 0.125 ng/μL $Eu^{3+}$ labeled cage antibody (Cisbio, Cat. No. 61T66KLB) diluted by a test buffer (Cisbio, Cat. No. 62SDBRDF), and 50 nM streptavidin-labeled XL665 (Cisbio, Cat. No. 610SAXLB).

The compounds were diluted to 1 mM in DMSO, then serially diluted 4-fold with DMSO to a minimum concentration of 0.061 μM, and each concentration was further diluted 40-fold with the reaction buffer. If the $IC_{50}$ value of a compound is very low, the initial concentration of the compound can be lowered.

Added 4 μL of compound solution and 2 μL of FGFR2 kinase solution to a 384-well assay plate (Thermo, Cat. No. 264706), mixed well and incubated for 15 minutes at room temperature; then added 4 μL of the substrate reaction solution, and incubated the reaction mixture for 60 minutes at room temperature; and then the reaction was terminated by adding an equal volume of 10 μL of the test solution, and the mixture was uniformly mixed and allowed to stand at room temperature. After 60 minutes, the phosphorylated product was simultaneously recognized by the $Eu^{3+}$ labeled cage antibody (donor) and the streptavidin-labeled XL665 antibody (receptor), after laser excitation, energy resonance transfer occurs between the donor and acceptor which are close to each other, and the energy was transferred from the donor (620 nm) to the acceptor (665 nm), which could be detected by a microplate reader EnVision (Perkin Elmer). The ratio of 665/620 is positively correlated with the degree of phosphorylation of the substrate, thus the activity of FGFR2 kinase was detected.

In this experiment, the group without the enzyme was a 100% inhibition group, the group with the enzyme yet without the compound was a 0% inhibition group. The percentage of inhibition on FGFR2 activity by the compound thus was calculated using the following formula:

Percentage of inhibition=100−100*($ratio_{compound}$−$ratio_{100\% \ inhibition}$)/($ratio_{100\% \ inhibition}$−$ratio_{100\% \ inhibition}$)

The $IC_{50}$ value of the compound was calculated from the 10 concentration points using the XLfit software in Excel by the following formula:

$$Y = Bottom + (Top - Bottom)/(1 + 10\string^((\log IC_{50} - X)*slope\ factor))$$

Where Y is the percentage of inhibition, Bottom is the bottom platform value of the S-curve, Top is the top platform value of the S-curve, X is the logarithm of the concentration of the compound to be tested, and slope factor is the slope coefficient of the curve.

FGFR3 Activity Inhibition Test

The experimental method is outlined below:

The reaction buffer contains the following components: 5-fold diluted enzymatic buffer/kinase 5× (Cisbio, Cat. No. 62EZBFDD) (its main component is 50 mM HEPES, pH 7.0), 5 mM $MgCl_2$ and 1 mM DTT; a human recombinant FGFR3 catalytic domain protein (amino acid 399-806), which was purchased from Yiqiao Shenzhou Biotech Co., Ltd., a 0.3 ng/µL kinase solution diluted by the reaction buffer; a substrate reaction solution containing 1000 nM biotinylated tyrosine kinase substrate diluted by the reaction buffer (Cisbio, Cat. No. 62TKOPEC) and 90 µM ATP; a test solution containing 0.125 ng/µL $Eu^{3+}$ labeled cage antibody (Cisbio, Cat. No. 61T66KLB) diluted by a test buffer (Cisbio, Cat. No. 62SDBRDF), and 62.5 nM streptavidin-labeled XL665 (Cisbio, Cat. No. 610SAXLB).

The compounds were diluted to 1 mM in DMSO, then serially diluted 4-fold with DMSO to a minimum concentration of 0.061 µM, and each concentration was further diluted 40-fold with the reaction buffer. If the $IC_{50}$ value of a compound is very low, the initial concentration of the compound can be lowered.

Added 4 µL of compound solution and 2 µL of FGFR3 kinase solution to a 384-well assay plate (Thermo, Cat. No. 264706), mixed well and incubated for 15 minutes at room temperature; then added 4 µL of the substrate reaction solution, and incubated the reaction mixture for 60 minutes at room temperature; and then the reaction was terminated by adding an equal volume of 10 µL of the test solution, and the mixture was uniformly mixed and allowed to stand at room temperature. After 60 minutes, the phosphorylated product was simultaneously recognized by the $Eu^{3+}$ labeled cage antibody (donor) and the streptavidin-labeled XL665 antibody (receptor), after laser excitation, energy resonance transfer occurs between the donor and acceptor which are close to each other, and the energy was transferred from the donor (620 nm) to the acceptor (665 nm), which could be detected by a microplate reader EnVision (Perkin Elmer). The ratio of 665/620 is positively correlated with the degree of phosphorylation of the substrate, thus the activity of FGFR3 kinase was detected.

In this experiment, the group without the enzyme was a 100% inhibition group, the group with the enzyme yet without the compound was a 0% inhibition group. The percentage of inhibition on FGFR3 activity by the compound thus was calculated using the following formula:

Percentage of inhibition=100−100*($ratio_{compound}$−$ratio_{100\% \ inhibition}$)/($ratio_{100\% \ inhibition}$−$ratio_{100\% \ inhibition}$)

The $IC_{50}$ value of the compound was calculated from the 10 concentration points using the XLfit software in Excel by the following formula:

Y=Bottom+(Top−Bottom)/(1+10^((log $IC_{50}$−X)*slope factor))

Where Y is the percentage of inhibition, Bottom is the bottom platform value of the S-curve, Top is the top platform value of the S-curve, X is the logarithm of the concentration of the compound to be tested, and slope factor is the slope coefficient of the curve.

FGFR4 Activity Inhibition Test

The experimental method is outlined below:

The reaction buffer contains the following components: 5-fold diluted enzymatic buffer/kinase 5× (Cisbio, Cat. No. 62EZBFDD) (its main component is 50 mM HEPES, pH 7.0), 5 mM $MgCl_2$ and 1 mM DTT; a human recombinant FGFR4 catalytic domain protein (amino acid 460-802), which was purchased from Tsinghua University Protein Research Technology Center, a 0.5 ng/µL kinase solution diluted by the reaction buffer; a substrate reaction solution containing 500 nM biotinylated tyrosine kinase substrate diluted by the reaction buffer (Cisbio, Cat. No. 62TKOPEC) and 90 µM ATP; a test solution containing 0.125 ng/µL $Eu^{3+}$ labeled cage antibody (Cisbio, Cat. No. 61T66KLB) diluted by a test buffer (Cisbio, Cat. No. 62SDBRDF), and 31.25 nM streptavidin-labeled XL665 (Cisbio, Cat. No. 610SAXLB).

The compounds were diluted to 1 mM in DMSO, then serially diluted 4-fold with DMSO to a minimum concentration of 0.061 µM, and each concentration was further diluted 40-fold with the reaction buffer. If the $IC_{50}$ value of a compound is very low, the initial concentration of the compound can be lowered.

Added 4 µL of compound solution and 2 µL of FGFR4 kinase solution to a 384-well assay plate (Thermo, Cat. No. 264706), mixed well and incubated for 15 minutes at room temperature; then added 4 µL of the substrate reaction solution, and incubated the reaction mixture for 60 minutes at room temperature; and then the reaction was terminated by adding an equal volume of 10 µL of the test solution, and the mixture was uniformly mixed and allowed to stand at room temperature. After 60 minutes, the phosphorylated product was simultaneously recognized by the $Eu^{3+}$ labeled cage antibody (donor) and the streptavidin-labeled XL665 antibody (receptor), after laser excitation, energy resonance transfer occurs between the donor and acceptor which are close to each other, and the energy was transferred from the donor (620 nm) to the acceptor (665 nm), which could be detected by a microplate reader EnVision (Perkin Elmer). The ratio of 665/620 is positively correlated with the degree of phosphorylation of the substrate, thus the activity of FGFR4 kinase was detected.

In this experiment, the group without the enzyme was a 100% inhibition group, the group with the enzyme yet without the compound was a 0% inhibition group. The percentage of inhibition on FGFR4 activity by the compound thus was calculated using the following formula:

Percentage of inhibition=100−100*($ratio_{compound}$−$ratio_{100\% \ inhibition}$)/($ratio_{100\% \ inhibition}$−$ratio_{100\% \ inhibition}$)

The $IC_{50}$ value of the compound was calculated from the 10 concentration points using the XLfit software in Excel by the following formula:

Y=Bottom+(Top−Bottom)/(1+10^((log $IC_{50}$−X)*slope factor))

Where Y is the percentage of inhibition, Bottom is the bottom platform value of the S-curve, Top is the top platform value of the S-curve, X is the logarithm of the concentration of the compound to be tested, and slope factor is the slope coefficient of the curve.

TABLE 1

| Compound No. | IC$_{50}$ | | | |
|---|---|---|---|---|
| | FGFR1 | FGFR2 | FGFR3 | FGFR4 |
| 1 | B | B | B | B |
| 3 | C | B | B | B |
| 7 | A | A | A | A |
| 8 | C | B | B | C |
| 9 | C | B | C | C |
| 10 | B | A | A | B |
| 11 | B | B | B | B |
| 12 | C | A | A | B |
| 13 | B | A | A | B |
| 14 | A | A | A | A |
| 15 | C | B | B | B |
| 16 | B | B | A | B |
| 17 | A | A | A | A |
| 18 | B | A | B | B |
| 19 | A | A | A | A |
| 20 | A | A | A | A |
| 21 | A | A | A | A |
| 22 | A | A | A | A |
| 23 | B | A | A | B |
| 25 | B | B | B | B |
| 26 | A | A | A | A |
| 27 | B | A | B | B |
| 28 | B | B | A | B |
| 29 | B | A | A | B |
| 30 | B | A | A | B |
| 31 | B | A | A | B |
| 32 | C | B | B | C |
| 33 | B | C | C | B |
| 34 | B | A | A | B |

A < 10 nM; 10 nM ≤ B < 100 nM; 100 nM ≤ C < 1000 nM

The compounds in the examples of the present invention have a significant inhibitory effect on the activity of FGFR, preferably having an IC$_{50}$ of from 100 to 1000 nM, more preferably an IC$_{50}$ of less than 100 nM, and most preferably an IC$_{50}$ of less than 10 nM.

Determination of Inhibition on the Proliferation of Hep3B Cells

The effect of the compounds of the present invention on cell proliferation of Hep3B hepatoma cell line was assessed using a luminescent cell viability assay (Table 2).

The experimental method is outlined below:

CellTilter-Glo reagent (Promega, Cat. No. G7572) consists of CTG lyophilized powder and CTG buffer. Before use, the lyophilized powder needs to be dissolved in the buffer.

The compound was diluted with DMSO (Sigma, Cat. No. D5879) to 5 mM, then serially diluted 4 times with DMSO to a minimum concentration of 0.31 μM, and each concentration point was further diluted 50 times with a DMEM medium free of FBS (ThermoFisher, Cat. No. 11995073). If the compound IC$_{50}$ value was very low, the initial concentration of the compound could be lowered.

Hep3B cells (obtained from the Cell Resource Center of Shanghai Institutes for Biological Sciences, Chinese Academy of Sciences) were cultured in DMEM complete culture medium containing a mixture solution of 10% FBS (GBICO, Cat. No. 10099-141) and 100 U/mL Streptomycin (ThermoFisher, Cat. No. 15140122). When the cells reached 80-90% confluency in the culture container, the cells were digested with 0.25% trypsin (containing EDTA) (ThermoFisher, Cat. No. 25200056), dispersed and then plated on a white 384-well culture plate (ThermoFisher, Cat. No. 164610), each well contains about 1000 cells (27 μL DMEM complete culture medium), then the 384-well plates were incubated overnight (18 to 20 hours) in a 37° C., 5% CO$_2$ incubator.

After overnight incubation, 3 μL of DMEM diluted compound was added to each well, which was then gently centrifuged to mix well, and then the 384-well plate was placed in a 37° C., 5% CO$_2$ incubator to continue the culture, and after 72 hours, the plate was taken out and allowed to stand at room temperature for 30 minutes, next added 15 μL of CTG reagent per well, which was warmed up to room temperature, the plate was shaken gently on a shaker for 3 minutes to ensure sufficient cell lysis, allowed to stand 10 minutes to stabilize the luminescence signal, and then read the luminescence signal with EnVision (Perkin Elmer).

The luminescent signal of BLU9931 (Cancer Discovery 2015, 5, 424) group with 10 μM Blueprint was used as signal$_{100\% \ inhibition}$, and the luminescent signal of 0.2% DMSO group was used as signal$_{0\% \ inhibition}$.

The percentage of inhibition on Hep3B cell proliferation by the compound could be calculated by the following formula:

Percentage of inhibition=100−100*(signal$_{compound}$−signal$_{100\% \ inhibition}$)/(signal$_{0\% \ inhibition}$−signal$_{100\% \ inhibition}$)

The compound IC$_{50}$ value was calculated from 8 concentration points using XLfit (ID Business Solutions Ltd., UK) software by the following formula:

$Y = \text{Bottom} + (\text{Top} - \text{Bottom})/(1 + 10^{((\log IC_{50} - X) * \text{slope factor})})$ Where Y is the percentage of inhibition, Bottom is the bottom platform value of the S-curve, Top is the top platform value of the S-curve, X is the logarithm of the concentration of the compound to be tested, and slope factor is the slope coefficient of the curve.

Determination of Inhibition on the Proliferation of RT4 Cells

The effect of the compounds of the present invention on cell proliferation of the RT4 bladder cancer cell line was assessed using a luminescent cell viability assay (Table 2).

For the experimental method, please refer to the method for determining the inhibition on the proliferation of Hep3B cells. The RT4 cells were obtained from the Cell Resource Center of the Shanghai Institutes for Biological Sciences, Chinese Academy of Sciences, and the positive control was ((S)-1-(3-(4-Amino-3-((3,5-dimethoxyphenyl)ethynyl)-1H-pyrazolo[3,4-d]pyrimidin-1-yl)pyrrolidin-1-yl)prop-2-en-1-one) disclosed in the Example 1 of the Taiho patent application WO2015008844A1.

Determination of Inhibition on the Proliferation of SNU-16 Cells

The effect of the compounds of the present invention on cell proliferation of SNU-16 gastric cancer cell line was assessed using a luminescent cell viability assay (Table 2).

For the experimental method, please refer to the method for determining the inhibition on the proliferation of Hep3B cells. SNU-16 cells are HB-8064 from ATCC, the positive control was BJG398 from Novartis.

TABLE 2

| Compound No. | IC$_{50}$ | | |
|---|---|---|---|
| | Hep3B | RT4 | SNU-16 |
| 1 | B | B | B |
| 7 | A | A | A |
| 10 | B | B | A |
| 12 | C | C | N.D. |
| 17 | A | A | A |
| 18 | N.D. | B | A |

TABLE 2-continued

| Compound No. | IC$_{50}$ | | |
|---|---|---|---|
| | Hep3B | RT4 | SNU-16 |
| 19 | N.D. | N.D. | B |
| 20 | N.D. | N.D. | B |
| 21 | A | A | A |
| 22 | A | A | A |
| 23 | A | B | A |
| 26 | B | A | A |
| 28 | N.D. | A | A |
| 29 | A | A | A |
| 30 | B | A | A |
| 31 | B | A | A |
| 34 | B | A | A |

Note:
A < 10 nM; 10 nM ≤ B < 100 nM; 100 nM ≤ C < 1000 nM
N.D.: Not detected

The compounds in the examples of the present invention have significant inhibitory effects on cell proliferation of Hep3B, RT4 and SNU-16, respectively, preferably with an IC$_{50}$ of 100 to 1000 nM, and more preferably an IC$_{50}$ of less than 100 nM.

Example 35

Efficacy in the SNU-16 Xenograft Model

The study was conducted to evaluate the in-vivo anti-tumor activity of compound 21 in female BALB/c nude mice bearing FGFR2-overexpressed SNU-16 gastric cancer cell line derived xenograft tumors.

Female BALB/c nude mice of 6-8 weeks old were ordered from Beijing Vital River Laboratory Animal Technology Co., Ltd. SNU-16 tumor cells (purchased from ATCC) were cultured in RPMI-1640 medium (purchased from Gibco) supplemented with 10% FBS (purchased from Gibco) at 37° C. under 5% CO$_2$. The cells were harvested in 90% confluence and no less than 90% viability, and then counted. Compound 21 was suspended in a vehicle comprised of 0.5% methylcellulose, 0.2% Tween-80 and 5% DMSO, and the reference compound BGJ-398 was suspended in a mixture of 0.5% methylcellulose and 0.2% Tween-80. Mice were inoculated subcutaneously into the right flank with 200 uL of 8×10$^6$ SNU-16 cells resuspended in 50% Matrigel (purchased from Corning). After the tumor sizes reached 100300 mm$^3$, the animals in good health condition were randomly placed into 6 groups (6 animals per group) and orally dosed with vehicle, compound 21 at 0.3, 1, 3 and 10 mg/kg, and BGJ-398 at 10 mg/kg, twice a day (BID), respectively. Dosing was initiated on day 0 and effects on tumor growth were evaluated by measuring the percentage of tumor growth inhibition (TGI) at the end of the study. Tolerability was assessed by body weight loss, lethality, and clinical signs of adverse treatment-related side effects. Tumor volume and body weight were measured twice per week during the administration period. The percentage of TGI was determined on day 25 after treatment. The difference between the mean value of tumor volume in the treatment group and that in the vehicle group was analyzed for significance using one-way ANOVA (followed by Dennett's test) at each time point and a P<0.05 was considered to be statistically significant.

The efficacy results demonstrated that compound 21 dose-dependently reduced tumor size in the SNU-16 model. The mean tumor size of the vehicle-treated mice reached 953 mm$^3$ on day 25 after treatment. Treatment with compound 21 at dose levels of 10, 3, 1 and 0.3 mg/kg (BID for 25 days) demonstrated significant anti-tumor activities, with mean tumor size reduced to 103, 200, 261 and 240 mm$^3$, and the corresponding TGI % of 108, 95.9, 88.3 and 91.0%, respectively (P<0.0001 for all groups vs. vehicle) (FIG. 1). BGJ-398 also showed significant anti-tumor activity at 10 mg/kg in this study.

Figure 2:
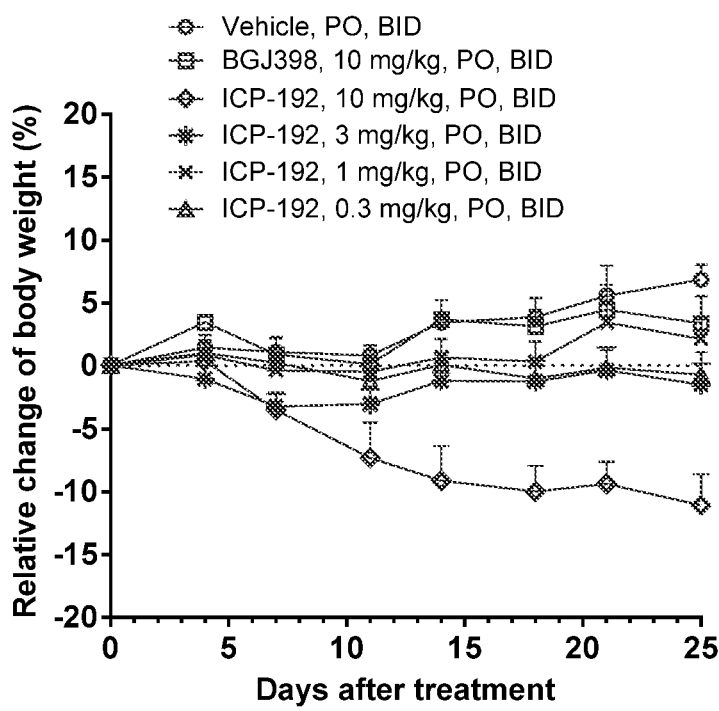
FIG. 2 shows the relative change of body weights (%) during treatment in the SNU-16 xenograft model. Relative change of body weight (RCBW) was calculated based on the following formula: RCBW %=(BWi−BW0)/BW0×100%, where BWi was the body weight on the day of dosing and BW0 was the body weight on the first day of administration. Data points represent the percentages of group mean change in BW and error bars represent standard errors of the mean (SEM).

Compound 21 at dose levels of 3, 1 and 0.3 mg/kg BID was well-tolerated by the tumor-bearing animals with no body weight loss during the study. The mice dosed with compound 21 at 10 mg/kg showed mean body weight loss of 11% but without significant decrease of locomotor activities (FIG. 2).

In summary, the results of this study demonstrated that compound 21 had marked anti-tumor activities against FGFR2 overexpressed SNU-16 human gastric cancer xenograft model and was well-tolerated by the tumor-bearing animals. The results indicated that compound 21 is a safe and efficacious anti-cancer agent.

The invention claimed is:

1. A compound of Formula III, or its stereoisomers, pharmaceutically acceptable salts thereof:

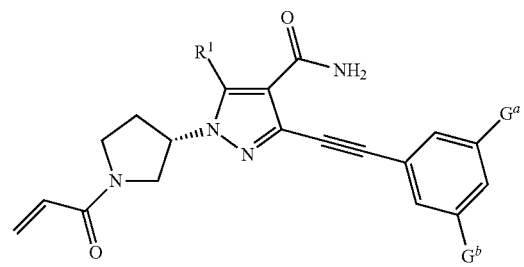

Formula III wherein,
R$^1$ is —NHR$^3$;
G$^a$ and G$^b$ are —OR$^8$, and
R$^3$ and R$^8$ are independently H or C$_{1-6}$ alkyl;
wherein each hydrogen of the compound is optionally substituted by $^2$H.

2. The compound according to claim 1, wherein R$^3$ and R$^8$ are methyl.

3. A pharmaceutical composition comprising the compound according to claim 1 and a pharmaceutically acceptable carrier and an excipient.

4. A method of treating a FGFR-associated disease, comprising administering to a patient in need thereof a therapeutically effective amount of the compound according to claim 1.

5. The method according to claim 4, wherein said FGFR-associated disease is liver cancer, gastric cancer, non-small cell lung cancer, bladder cancer, esophageal cancer, melanoma, rhabdomyosarcoma, renal cell carcinoma, multiple myeloma, breast cancer, ovarian cancer, endometrial cancer, cervical cancer, colon cancer, bladder cancer, pancreatic cancer, lung cancer, breast cancer, or prostate cancer.

6. The method according to claim 5, wherein said FGFR-associated disease is liver cancer, gastric cancer, non-small cell lung cancer, or bladder cancer.

* * * * *